US006228643B1

(12) United States Patent
Greenland et al.

(10) Patent No.: US 6,228,643 B1
(45) Date of Patent: May 8, 2001

(54) PROMOTER

(75) Inventors: Andrew James Greenland, Maidenhead; Didier Rene Philippe Thomas, Bracknell; Ian Jepson, Maidenhead, all of (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 08/821,994

(22) Filed: Mar. 22, 1997

(30) Foreign Application Priority Data

Mar. 22, 1996 (GB) .................................................. 9606062

(51) Int. Cl.$^7$ .............................. C12N 5/14; C12N 15/82; A01H 5/00
(52) U.S. Cl. ....................... 435/419; 435/320.1; 435/468; 536/23.2; 536/23.6; 536/24.1; 800/278; 800/285; 800/286; 800/287; 800/288; 800/295; 800/298; 800/303
(58) Field of Search .................................. 536/23.6, 24.1, 536/23.2; 435/320.1, 419, 468; 800/278, 285, 286, 287, 288, 295, 298, 303

(56) References Cited

FOREIGN PATENT DOCUMENTS

| 90/08827 | 8/1990 | (WO) . |
| 91/08299 | 6/1991 | (WO) . |
| 94/03619 | 2/1994 | (WO) . |
| 96/04393 | 2/1996 | (WO) . |
| 96/37609 | 11/1996 | (WO) . |
| 97/06268 | 2/1997 | (WO) . |
| 97/06269 | 2/1997 | (WO) . |
| 97/11189 | 3/1997 | (WO) . |
| 97/13864 | 4/1997 | (WO) . |

OTHER PUBLICATIONS

Ascenzi, P., et al., Biochimica et Biophysica Acta, The pH dependence of pre–steady–state and steady–state kinetics for the papain–catalyzed hydrolysis of N–α–carbobenzoxyglycine ρ–nitrophenyl, vol. 912, 1987, pp. 203–210.

Becker, C., et al., Plant Molecular Biology, "PCR cloning and expression analysis of cDNAs encoding cysteine proteinases from germinating seeds of Vicia sativa L.," vol. 26, 1994, pp. 1207–1212.

Bevan, M., Nucleic Acids Research, "Binary Agrobacterium vectors for plant transformation," vol. 12, No. 22, 1984, pp. 8711–8721.

Boylan, M., et al., Planta, "Purification of an endopeptidase involved with storage–protein degradation in Phaseolus vulgaris L. cotyledons," vol. 170, 1987, pp. 343–352.

Bradford, M., Analytical Biochemistry, "A Rapid and Sensitive Method for the Quantitation of Microgram Quantities of Protein Utilizing the Principle of Protein–Dye Binding," vol. 72, 1976, pp. 248–254.

Cammue, B., et al., The Journal of Biological Chemistry, "Isolation and Characterization of a Novel Class of Plant Antimicrobial Peptides from Mirabilis jalapa L. Seeds," vol. 267, No. 4, Issue of Feb. 5, 1992, pp. 2228–2233.

Cervantes, E., et al., Molecular Biology, "Ethylene regulates the expression of a cysteine proteinase gene during germination of chickpea (Cicer arietinum L.)," vol. 25, 1994, pp. 207–215.

Cercos, M., et al., Plant Physiol., "Promoter Analysis of a GA–Induced Cysteine Endoprotease Gene in Barley Aleurone Cells," vol. 108 (2 Suppl), 1995, p. 79.

Cohen, L., et al., Gene, "Cloning and sequencing of papain–encoding cDNA," vol. 48, 1986, pp. 219–227.

Comai, L., et al., Proc. Natl. Acad. Sci. USA, "Transcriptional activities in dry seed nuclei indicate the timing of the transition from embryogeny to germination," vol. 87, Apr. 1990, pp. 2671–2674.

deBarros, E., et al., Plant Science, "Cloning of a cDNA encoding a putative cysteine protease from germinating maize seeds," vol. 99, 1994, pp. 189–197.

Dietrich, R., et al., The Plant Cell, "Spatial Patterns of Gene Expression in Brassica napus Seedlings: Identification of a Cortex–Specific Gene and Localization of mRNAs Encoding Isocitrate Lyase and a Polypeptide Homologous to Proteinases," vol. 1, Jan. 1989, pp. 73–80.

Edwards, K., et al., Nucleic Acids Research, "A simple and rapid method for the preparation of plant genomic DNA for PCR analysis," vol. 19, No. 6, 1991, p. 1349.

Goetting–Minesky, P., et al., Proc. Natl. Acad. Sci. USA, "Differential gene expression in an actinorhizal symbiosis: Evidence for nodule–specific cysteine proteinase," vol. 91, Oct. 1994, pp. 9891–9895.

Goetting–Minesky, M., et al., American Journal of Botany, "Evidence for a nodule–specific cysteine proteinase in an actinorhizal symbiosis," vol. 81 (6 Suppl.), 1994, p. 66.

Graham, I., et al., The Plant Journal, "Analysis of the cucumber malate synthase gene promoter by transient expression and gel retardation assays," vol. 6(6), 1994, pp. 893–902.

Grossberger, D., Nucleic Acids Research, "Minipreps of DNA from bacteriophage lambda," vol. 15, No. 16, 1987, p. 6737.

Guerrero, F., et al., Plant Molecular Biology, "Turgor–responsive gene transcription and RNA levels increase rapidly when pea shoots are wilted. Sequence and expression of three inducible genes," vol. 15, 1990, pp. 11–26.

(List continued on next page.)

Primary Examiner—Mary E. Mosher
(74) Attorney, Agent, or Firm—Liza D. Hohenschutz

(57) ABSTRACT

A promoter comprising the DNA sequence of an oil seed rape cysteine protease gene promoter of class 1, 2 or 6 is described. The promoter may be used in an expression system for at least the tissue or tissues of a germinating seedling or developing grain or plant (e.g. in the root, cotyledons, leaves and stem). In a preferred embodiment, the expression system comprises a disrupter gene fused to a promoter according to the present invention.

68 Claims, 89 Drawing Sheets

OTHER PUBLICATIONS

Hara–Nishimura, I., et al., The Plant Cell, "Molecular Characterization of a Vacuolar Processing Enzyme Related to a Putative Cysteine Proteinase of *Schistosoma mansoni*," vol. 5, Nov. 1993, pp. 1651–1659.

Hara–Nishimura, I., et al., J. Plant Physiol., "Vacuolar Processing Enzyme Responsible for Maturation of Seed Proteins," vol. 145, 1995, pp. 632–640.

Holsters, M., et al., Molec. Gen. Genet., "Transfection and Transformation of *Agrobacterium tumefaciens*," vol. 163, 1978, pp. 181–187.

Jefferson, R., et al., Biochemical Society Transactions, "The use of the *Escherichia coli* β–glucuronidase gene as a gene fusion marker for studies of gene expression in higher plants," vol. 15, 1987, pp. 17–18.

Jepson, I., et al., Plant Molecular Biology Reporter, "A Rapid Procedure for the Construction of PCR cDNA Libraries from Small Amounts of Plant Tissue," vol. 9(2), 1991, pp. 131–138.

Jiang, B., et al., Plant Physiol., "Association of a 33–Kilodalton Cysteine Proteinase Found in Corn Callus with the Inhibition of Fall Armyworm Larval Growth," vol. 108, 1995, pp. 1631–1640.

Jones, M., et al., Plant Molecular Biology, "Ethylene–regulated expression of a carnation cysteine proteinase during flower petal senescence," vol. 28, 1995, pp. 505–515.

Karrer, K., et al., Proc. Natl. Acad. Sci. USA, "Two distinct gene subfamilies within the family of cysteine protease genes," vol. 90, Apr.1993, pp. 3063–3067.

Kianian, S., et al., Genome, "Genetic analysis of major multigene families in *Brassica oleracea* and related species," vol. 35, 1992, pp. 516–527.

Koehler, S., et al., The Plant Cell, "Hormonal Regulation, Processing, and Secretion of Cysteine Proteinases in Barley Aleurone Layers," vol. 2, Aug. 1990, pp. 769–783.

Kóródi, I., et al., Biochemistry, "Disulfide Bond Formation between the Active–Site Thiol and One of the Several Free Thiol Groups of Chymopapain," vol. 25, No. 22, 1986, pp. 6895–6900.

Lidgett, A., et al., Plant Molecular Biology, "Isolation and expression pattern of a cDNA encoding a cathepsin B–like protease from *Nicotiana rustica*," vol. 29, 1995, pp. 379–384.

Lin, E., et al., Plant Moleclar Biology, "Fruit developmental regulation of the kiwi–fruit actinidin promoter is conserved in transgenic petunia plants," vol. 23, 1993, pp. 489–499.

Linthorst, H., Plant Physiol., "Nucleotide Sequence of a cDNA Clone Encoding Tomato (*Lycopersicon esculentum*) Cysteine Proteinase," vol. 101, 1993, pp. 705–706.

Linthorst, H., et al., Plant Molecular Biology, "Circadian expression and induction by wounding of tobacco genes for cysteine proteinase," vol. 21, 1993, pp. 685–694.

Mallinson, D., et al., Microbiology, "Identification and molecular cloning of four cysteine proteinase genes from the pathogenic protozoon *Trichomonas vaginalis*," vol. 140, 1994, pp. 2725–2735.

Mikkelsen, T., et al., Nature, "The risk of crop transgene spread," vol. 380, Mar. 7, 1996, p. 31.

Marttila, S., et al., Cell Biology International, "Expression of the 30 kD Cysteine Endoprotease B in Germinating Barley Seeds," vol. 17, No. 2, 1993, pp. 205–212.

Marttila, S., et al., Physiologia Plantarum, "Differential localization of two acid proteinases in germinating barley (*Hordeum vulgare*) seed," vol. 93, 1995, pp. 317–327.

McKee, R., et al., Biochem. J., "Molecular cloning of two cysteinse proteinases from paw–paw (*Carica papaya*)," vol. 237, 1986, pp. 105–110.

Minami, A., et al., Plant Cell Physiol., "Transient and Specific Expression of a Cysteine Endopeptidase Associated with Autolysis during Differentiation of Zinnia Mesophyll Cells into Tracheary Elements," vol. 36(8), 1995, pp. 1599–1606.

Mino, M., et al., Japan. J. Breed., "Hybrid Vigor in Relation to Lipid and Protein Metabolism in Germinating Maize Kernels," vol. 38, 1988, pp. 428–436.

Nong, V., et al., Biochimica et Biophysica Acta, "cDNA cloning for a putative cysteine proteinase from developing seeds of soybean," vol. 1261, 1995, pp. 435–438.

Okayama, H., et al., Methods in Enzymology, "High Efficiency Cloning of Full–Length cDNA; Construction and Screening of cDNA Expression Libraries for Mammalian Cells," vol. 154, 1987, pp. 3–28.

Pautot, V., et al., Gene, "Expression of a mouse metallothionein gene in transgenic plant tissues," vol. 77, 1989, pp. 133–140.

Pladys, D., et al., Plant Physiol., "Proteolysis during Development and Senescence of Effective and Plant Gene–Controlled Ineffective Alfalfa Nodules," vol. 103, 1993, pp. 379–384.

Praekelt, U., et al., Plant Molecular Biology, "Molecular analysis of actinidin, the cysteine proteinase of *Actinidia chinensis*," vol. 10, 1988, pp. 193–202.

Revell, D., et al., Gene, Nucleotide sequence and expression in *Eschericia coli* of cDNAs encoding papaya proteinase omega from *Carica papaya*, vol. 127, 1993, pp. 221–225.

Sanger, F., et al. Proc. Natl. Acad. Sci. USA, "DNA sequencing with chain–terminating inhibitors," vol. 74, No. 12, 1977, pp. 5463–5467.

Schaffer, M., et al., Plant Physiol., "Analysis of mRNAs that Accumulate in Response to Low Temperature Identifies a Thiol Protease Gene in Tomato," vol. 87, 1988, pp. 431–436.

Shimada, T., et al., Plant Cell Physiol., "Vacuolar Processing Enzyme of Soybean That Converts Proproteins to the Corresponding Mature Forms," vol. 35(4), 1994, pp. 713–178.

Shintani, A., et al., Plant Physiol., "Nucleotide Sequence of cDNA for a Putative Cysteine Protease from Rice Seeds," vol. 107, 1995, p. 1025.

Shutov, A., et al., Phytochemistry, "Degradation of Storage Proteins in Germinating Seeds," vol. 26, No. 6, 1987, pp. 1557–1566.

Smart, C., et al., Physiologia Plantarum, "The timing of maize leaf senescence and characterization of senescence–related cDNAs," vol. 93, 1995, pp. 673–682.

Takeda, O., et al., J. Biochem., "Isolation and Analysis of cDNA Encoding a Precursor of *Canavalia ensiformis* Asparaginyl Endopeptidase (Legumain)," vol. 116, 1994, pp. 541–546.

Taylor, M., et al., Protein Engineering, "Recombinant pro–regions from papain and papaya proteinase IV are selective high affinity inhibitors of the mature papaya enzymes," vol. 8, No. 1, 1995, pp. 59–62.

Terras, F., et al., FEBS Letters, "A new family of basic cysteine–rich plant antifungal proteins from Brassicaceae species," vol. 316, No. 3, Feb. 1993, pp. 233–240.

Thomas, M., et al., Biochem. J., "Structure of chymopapain M the late–eluted chymopapain deduced by comparative modelling techniques and active–centre characteristics determined by pH–dependent kinetics of catalysis and reactions with time–dependent inhibitors: the Cys–25/His–159 ion–pair is insufficient for catalytic competence in both chymopapain M and papain," vol. 300, 1994, pp. 805–820.

Valpuesta, V., et al., Plant Molecular Biology, "Up–regulation of a cysteine protease accompanies the ethylene–insensitive senescence of daylily (Hemerocallis) flowers," vol. 28, 1995, pp. 575–582.

Vernet, T., et al., The Journal of Biological Chemistry, "The ionization state of a Conserved Amino Acid Motif Within the Pro Region Participates in the Regulation of Intramolecular Processing," vol. 270, No. 18, Issue of May 5, 1995, pp. 10838–10846.

Watanabe, H., et al., The Journal of Biological Chemistry, "Molecular Cloning and Gibberellin–induced Expression of Multiple Cysteine Proteinases of Rice Seeds (Oryzains)," vol. 266, No. 25, Issue of Sep. 5, 1991, pp. 16897–16902.

Wiederanders, B., et al., The Journal of Biological Chemistry, "Phylogenetic Conservation of Cysteine Proteinases," vol. 267, No. 19, Jul. 5, 1992, pp. 13708–13713.

Yamauchi, D., et al., Plant Cell Physiol., "Cysteine Endopeptidase from *Vigna mungo*: Gene Structure and Expression," vol. 33, No. 6, 1992, pp. 789–797.

Snowden et al (Nucleic Acids Research 18:6684, 1990).*

Paul et al (Plant Physiology 108:261–268, 1995).*

Graham, I.A., et al., Plant Molecular Biology, "Development regulation of expression of the malate synthase gene in transgenic plants," vol. 15, 1990, pp. 539–549.

* cited by examiner

FIG. 3A-1

Solution Parameters:

- Nucleic Alphabet = Identity
- Output line length = 80
- Compress = Off
- Histogram = Off
- Randomization = Off AMINO-Res-length = 2
    DELetion-weight = 10.00
    LEngth-factor = 0
    Matching-weight = 10.00
    NUCLEIC-Res-length = 4
    SPread-factor = 90

Clustered order of selected sequences:
                                with 8.403

| | | | | |
|---|---|---|---|---|
| 165/288 | 1. | OSR8.401COD | 57% homol. | (1-317) |
| | 4. | OSR8.406COD | | (1-361) |
| | 5. | OSR8.403COD | | (1-468) |
| | 15. | OSR8.404COD | | (1-501) |
| | 16. | OSR8.402COD | | (1-501) |
| 127/474 | 13. | OSR8.389COD | 90% homol. | (1-504) |
| | 12. | OSR8.387COD | | (1-504) |

```
OSR8.401CO  120  GAATagAAagTTGTgACaAATTGATaGcTACGctgGTGTaaaatCaaAtGACGAgAaaGCC
OSR8.406CO  117  GAATTCAAGAGTTGTGTAACTATTGATGGTTACGAAGATGTTCCTACTGAAGATGAAACGGCC
OSR8.403CO  120  GAATTCAAGAGTTGTGTAACTATTCGATGGATACGAAGATGTTCCTAGTAAAGATGAAACCGCG
OSR8.404CO  120  aAATTCgAGAGTTGTgACTATCGATGGATACGAAGATGTTCCTAGTAAAGATGAAACCGCG
OSR8.402CO  120  GAATTCAAGAGTTGTAACTATTGATGGATACGAAGATGTTCCTAGTAAAGATGAAACCGCG
OSR8.389CO  120  GAATTCAAGAGTTGTAACTATTGATGGTTACGAAGATGTTCCTACTGAAGATGAAACGGCg
OSR8.387CO  120  GAATTCAAGAGTTGTAACTATTGATGGTTACGAAGATGTTCCTACTGAAGATGAAnnbnnn consensus        gAATtcaAgaGTTGTaACTAtTGATgG-TACGaaGaTgTtcctactaAaGAtGAaaccgcc
```

```
OSR8.403CO    422  CCGGTAAGTGTGGGATTnCnATAGAAGCCTCGTATCCGGTTAAGTAC  SHORT CLONE
OSR8.404CO    422  CCGGTAAGTGTGGGATTGCGATAGAAGCCTCGTATCCGGTTAAGTACACAGCCCAAACCCGGT
OSR8.402CO    422  CCGGTAAGTGTGGGATTGCGATAGAAGCCTCGTATCCGGTTAAGTACACAGCCCAAACCCGGT
OSR8.389CO    425  CCNGCAAGTGTGnAATTnCNGTTnAAnnCTCGTACnCGGTTAAGTACAGTCCAAACCCGGT
OSR8.387CO    425  nCNGCAAGTnTnGAATTgCNGTTgAAgcCTCGTACCCGGTTAAGTACAGTCCAAACCCGnT
consensus          ccggtaagtgtgggattgcnatagaagcctcgtatccggttaagtacag-ccaaacccggt OSR8  01CO    318
OSR8.406CO    362
OSR8.403CO    469
OSR8.404CO    483  TCGTggGACCAGCAGTGTT
OSR8.402CO    483  TCGTnnGACCAGCAGTGTT
OSR8.389CO    486  TCGTGGAACCAGCAGTGTT  TgAAgTT
OSR8.387CO    486  TCGTGGAACCAGCAGTGTT
consensus          tcgtgg-accagcagtgtt Alignment score = 19760.00
```

FIG. 3B-1

```
DELetion-weight    = 1.00
LEngth-factor      = 0
Matching-weight    = 5.00
NUCLEIC-Res-length = 4
SPread-factor      = 90
```

Clustered order of selected sequences:

```
14.  OSR8.389NCOD  ⎤ 75% homol.  (1-240)
17.  OSR8.387NCOD  ⎦ with 8.402  (1-246)
 7.  OSR8.402NCOD       8.404    (1-242)
 6.  OSR8.404NCOD       8.403    (1-242)
```

Region Alignment: (listed in Clustered order)

```
OSR8.389NC   1 TGAAGTTTTAAAATAAAACTCA                           ATAAATCA CTTGGGAGTTTTATAAACTAAGATT
                   511                8.389                           526              535
OSR8.387NC   1 TGAAGTTTTAAAATAAAACTCA                           ATAAATCA CTTGGGAGTTTTATAAACTAAGATT
                   508                          8.387

OSR8.402NC   1 TGAAG     GTAACAAAAAGAATCTCATGCAGTAATCAAATTGGGATTGTTATAA  GTTAAAT
                                                                      8.702
OSR8.404NC   1 TGAAG     GTAACAAAAAG ATCTCATGCAGTAATCAAATTGGGATTGTTATAA GTTAAAT
               STOP                                                        552
consensus      TGAAGttgT---AAAA---aA-CTCAtgca-TAATCAa-TTGGGA-T-TtATAAc---A-
```

FIG. 3B-2

```
OSR8.389NC  57  TAATCTCATATTATTGTTTGTATGTATAGTAT------ATCAAAAAAGAAGTATTTGATCCACC
OSR8.387NC  57  TAATCTCATATTATTGTTTGTATGTATAGTAT------ATCAAAAAAGAAGTATTTGATCCACC
                                                         |582|
                                                         8.387R|TTCTTCCATAAACTAGGTGG
OSR8.402NC  59  TAATCTTGTATTATTGTTTGTATGTATAGTAT------ATCAAAAAAGAAGTATTTGATCCACC
OSR8.404NC  59  TAATCTTGTATTATTGTTTGTATGTATAGTATGGTATTTCGAAAAAAA                TTGATTCACC
                                                                                  @TGATTCACC
consensus       TAATCT---TATTATTGTTTGTATGTATAGTATt---AAAAAAGaaggtattTGAT-CACC OSR8.389NC  116 ATACGGATTTAAATCTGTATGGATCCTTATGTCGATC---AATATCATTTCGTTAAAGAAAGA
OSR8.387NC  116 ATACGGATTTAAATCTGTATGGATCCTTATGTCGATC---AATATCATTTCGTTAAAGAAAGA
                |606|
                TATGC
OSR8.402NC  112 ATAGGGATTTAAATCTGTATAAATCTCTATGTTGGTC   AATATCATTTCATTCAAAGAATAT
OSR8.404NC  112 ATAGGGATTTAAATCTGTATAAATCTCTAgGTTGGTC@AATATCATTTCATTCAAAGAATAT
consensus       ATA-GGATTTAAATCTGTAT--ATC---TAtGT-G-TCaAATATCATTTC-TT-AAAGAA---
```

FIG. 3B-3

```
OSR8.389NC  176  TTAATTTGG TTG TTTATGTATTAAGAGAAG TATAAT AAAA TGATATATTTCTC TTAA
OSR8.387NC  176  TTAATTTGG TTG TTTATGTATTAAGAGAAG TATAAT AAAA TGATATATTTCTC TTAA
OSR8.402NC  172  TTGCTTTGGCTTGATTATGTATTAAGAGAAATATAAAATGATATATTTCTC    AgCA
OSR8.404NC  173  TTGCTTTG CTTGATTATGTATTAAGAGAAATATAAAA TGgTATATTTCTC    AaCA
                                                          poly A signal
consensus        TT---TTTGgcTTG-TTATGTATTAAGAGAA-TATAATaAAAaTGaTATATTTCTCttAaca OSR8.389NC  233  AAAAAAAA
OSR8.387NC  235  tCAAAAAAAAA
OSR8.402NC  231  GCAAAAAAAAA
OSR8.404NC  231  GCAAAAAAAAA
                 TTTTTTTT                    MPRACE 1B
consensus        gcAAAAAAAaa
```

FIG. 4-1

```
OSR8.401COD from 1 to 317: (CLASS 1)
         10         20         30         40         50         60         70
nnnnncaatn gggnntgat ggacnnnnnt tttcaatttg tcattaaaaa ccatgggatt gacacagaga
         80         90        100        110        120        130        140
aagattatcc ttatcaagaa cgtgatggca cctgtaagaa agataagttg aatagaaagg ttgtgacaat
        150        160        170        180        190        200        210
tgatagctac gctggtgtaa aatcaaatga cgagaaaagcg ttactagaag ctgtagncgc tcagccagtt
        220        230        240        250        260        270        280
agtgttggta tctgtgggag cgagagagcg tttcagttat actctaaggg aatattctct ggcccatgtt
        290        300        310
caacatcatt ggaccacgca gtgctcatcg taggata
```

GEL: pri 40

Range to print (<CR>=ALL):
OSR8-402 from 1 to 743: (CLASS 2)

```
         10         20         30         40         50         60         70
gggtgcaacg ggngactgat ggactatgct tttcaattca tcatgaaaaa cggcggtttg aacaccgagc
```

FIG. 4-2

```
       80         90        100        110        120        130        140
aagattatcc ttaccgtggt tccaatggaa aatgcaattc tttactgaag aattcaagag ttgtaactat 150        160        170        180        190        200        210
tgatggatac gaagatgttc ctagtaaaga tgaaaccncn ttgaagagag cagtttcata ccagcctgtg 220        230        240        250        260        270        280
agtgttncta ttgatncctgg tggaannnct ttccaacatt accaatctgg aatcttcact ggaaagtgtg 290        300        310        320        330        340        350
gtacgaatat ggatcacgct gtggtggcgg ttggttatgg gtcagagaac ggcgttgact attggattgt 360        370        380        390        400        410        420
acgtaactct tggggtacac tttggggaga ggatggttac attaggatgg agagaaaacgt ggcgtctaaa 430        440        450        460        470        480        490
tccggtaagt gtgggattgc gatagaagcc tcgtatccgg ttaagtacag cccaaacccg gttcgtnnga 500        510        520        530        540        550        560
ccagcagtgt ttgaaggtaa caaaaaagaat ctcatgcagt aatcaaattg ggattgttat aagttaaatt 570        580        590        600        610        620        630
aatcttgtat tattgttttgt atgtatgttt tttcgaaaaa aattgattca ccataggggat ttaatctgta 640        650        660        670        680        690        700
taaatctcta tgttggtcaa tatcattttca ttcaaagaat atttgctttg gcttgattat gtattaagag 710        720        730        740
aaatataata aaaatgatat atttctcagc agcaaaaaaa aaa
```

FIG. 4-3

```
CYS8-389 from 1 to 744: (CLASS 6)

10         20         30         40         50         60         70
gggtgcaacg gggggttgat ggactatgct tttcaattca tcatgaaaaa cggcggtttg aacaccgagc 80         90        100        110        120        130        140
aagattatcc ttaccgtggt tccaatggaa aatgcaattc tttactgaag aattcaagag ttgtaactat 150        160        170        180        190        200        210
tgatggttac gaagatgttc ctactgaaga tgaaacgggcg ttgaagagag cagtttcata ccagcccgtg 220        230        240        250        260        270        280
agtgttgcca ttgaagctgg tggaagagtt ttccaacatt accaatcggg gatcttcact gggaagtgtg 290        300        310        320        330        340        350
ggacaaatct agatcatgca gtggtggctg ttggttatgg ttcagagaac ggtattgact attggattgt
```

FIG. 4-4

```
       360        370        380        390        400        410        420
aaggaactcg tggggtacac gttggggaga ggatggttac attagaatgg agagaaactt ggcaaggtcc 430        440        450        460        470        480        490
aagtccngca agtgtggaat tncngttnaa nnctcgtacn cggttaagta cagtccaaac ccggttcgtg 500        510        520        530        540        550        560
gaaccagcag tgtttgaagt tttttttaaaa taaaactcaa taatcacttg ggagttttat aactaagatt 570        580        590        600        610        620        630
taatctcata ttattgtttg tatgtatagt atatcaaaaa agaaggtatt tgatccacca tacgattta 640        650        660        670        680        690        700
atctgtatgg atccttatgt cgatcaatat catttcgttt aaagaaagat taatttggtt gtttatgtat 710        720        730        740
taagagaagt ataataaaat gatatatttc tcttaaaaaa aaaa
```

FIG. 7-1

```
CYS4_BRANA    123  scwafstaaaveginkivtgelvslseqelvdcdksynqpcngglmdyaFQFIMKNGGI
OSR8.403CO      1  ------------------------------------------------------------
OSR8.404CO      1  ------------------------------------------------------------
OSR8.402CO      1  ------------------------------------------------------------
OSR8.389CO      1  ----------------------------------XXXXXXXXXFQFIMKNGGI
         ┐93% homol.
OSR8.387CO      1  ----------------------------------XXNXXLMDYXFQFIMKNGGI
         ┘       │ WITH 8.103
OSR8.406CO      1  ----------------------------------GCNGXLMDYAFQFIMKNGGI
         ┐62% homol.
                   ----------------------------------GCNGGLMDYAFQFIMKNGGI
                   ----------------------------------GCNGGLMDYAFQFIMKNGGI
                   ----------------------------------XXXXXXXXXFQFIMKNGGI
OSR8.401CO      1  ----------------------------------XXnXgXmdXXFQFvjKNhGi consensus          scwafstaaaveginkivtgelvslseqelvdcdksynq--n--lmdy-FQFimKNGGI
```

FIG. 7-2

```
CYS4_BRANA  184  EKDYPY ——— HGTNGKCNSLLKNSRVVTIDGYEDVPSKDETALKRAVSYQPVSVAIDAGGRA
OSR8.403CO   23  EKDYPY ——— HGTNGKCNSLLKNSRVVTIDGYEDVPSKDETALKRAVSYQPVSVAIDAGGRA
OSR8.404CO   23  EKDYPY ——— HGTNGKCNSLLKNSRVVTIDGYEDVPSKDETALKRAVSYQPVSVAIDAGGRA
OSR8.402CO   23  EKDYPY ——— HGTNGKCNSLLKNSRVVTIDGYEDVPSKDETxLKRAVSYQPVSVAIDAGGRA
OSR8.389CO   23  EQDYPY RGSNGKCNSLLKNSRVVTIDGYEDVPSKDETALKRAVSYQPVSVxIDxGGxx
OSR8.387CO   23  EQDYPY RGSNGKCNSLLKNSRVVTIDGYEDVPTEDETALKRAVSYQPVSValeaGGTv
OSR8.406CO   23  EQDYPY RGSNGKCNSLLKNSRVVTIDGYEDVPTEDExxxxxxxxxxxxxxxxxxeaggRv
OSR8.401CO   23  EQDYPY RGSNGKCNSLL NSRVVTIDGYEDVPTEDEtALkrAVsYQPVSaleaggRa
                 EkDYPY gerdgtckkdxL NExVVTIDSMagVksnDEkAIleAVxaQPVSvgICgseRa consensus        E-DYPYqrgsngkcnsllkNsrvVTIDgYedVpskDEtalkravsyqpvsvaidaggra
```

FIG. 7-3

```
CYS4_BRANA  244  HYQSGIFTGKCGTNMDHAVVAVGYGSENGVDYWIVRNSWGTRWGEDGYIRMERN VASK
OSR8.403CO   83  HYQSGIFTGKCGTNMDHAVVAVGYGSENGVDYWIVRNSWGTRWGEDGYIRMERN ----
OSR8.404CO   83  HYQSGIFTGKCGTNMDHAVVAVGYGSENGVDYWIVRNSWGTRWGEDGYIRMERN VASK
OSR8.402CO   83  HYQSGIFTGKCGT(T)MDHAVVAVGYGSENGVDYWIVRNSWGTRWGEDGYIRMERN VASK
OSR8.389CO   83  HYQSGIFTGKCGTNMDHAVVAVGYGSENGVDYWIVRNSWGTRWGEDGYIRMERN VxSK
OSR8.387CO   83  HYQSGIFTGKCGTN(L)DHAVVAVGYGSENGVDYWIVRNSWG(T)WGEDGYIRMERN VaSK
OSR8.406CO   82  xYQxGIFTGKCGTNIDHAVVAVGYGSENGIDYW(I)VRNSWGTRWGEDGYIRMERNLARSK
OSR8.401CO   83  hYQSGIFTGKCGTNIDHAVVAVGYGSENGIDYWIVRNSWGTRWGEDGYIRMERNLARSK
                 (I)Y(G)(K)GIF(S)G(p)C(G)(T)(s)(I)DHAV(L)(I)V(G) SHORT CLONE
                                                VRNSW consensus    hYqsGIFtGkCgTn-DHAVvaVGygsengvdywivrnswgtrwgedgyirmernlvask
```

FIG. 7-4

```
                                              328
CYS4_BRANA   304  KCGIaIEASYPVKYspnpvrgtssv
                  |||||||||||||
OSR8.403CO   143  KCGIxIEASYPVKY SHORT CLONE
                  ||||||||||||||
OSR8.404CO   143  KCGIAIEASYPVKYSPNPVRgTSSV
                  |||||||||||||||||||||||||
OSR8.402CO   143  KCGIAIEASYPVKYSPNPVRxTSSV
                  |||||  ||||||||||||||||||
OSR8.389CO   144  KCGIxVxxSYxVKYSPNPVRGTSSV
                  |||||||||||||||||||||||||
OSR8.387CO   144  KxxIaVeaSYpVKYSPNPxRGTSSV

OSR8.406CO   121

OSR8.401CO   106 consensus         kcgiaieasypvkyspnpvrgtssv
                                          168
                                           ↑
Alignment score = 3484.00                 STOP
```

FIG. 9-2

```
CYS4_BRANA    7   WSLEHGKSNSNSNGIINQQDERFNIFKDNLRFIDLHN@NNKNATYKLGLTIFAnLTNDEYR
CYS2UP6_1    57   ------------------WSLEHGKSNSNSNGIINQQDERFNIFKDNLRFIDLHNdNNKNATYKLGLTIFADLTNDEYR
CYS2UP7_1    62   ------------------WSLEHGKSNSNSNGIINQQDERFNIFKDNLRFIDLHN@NNKNATYKLGLTIFADLTNDEYR
CYS2UP8_2    58   ------------------WSLEHGKSNSNSNGIINQQDERFNIFKDNLRFIDLHN@NNKNATYKLGLTIFADLTNDEYR
consensus         WSLEHGKSNSNSNGIINQQDERFNIFKDNLRFIDLHNeNNKNATYKLGLTIFAdLTNDEYR CYS4_BRANA   68   SLYLGARTEPVRriTKAkNVMKYSAAVNvdEVPvTVDWR@KGAVNAIKDQGTCGSCWAFS
CYS2UP6_1   118   SLYLGARTEPVRxxTKAxNVMKYSAAVNXVEVPETVDWRKKGAVNAIKDQGTCGSCWAFS
CYS2UP7_1   123   SLYLGARTEPVRxxTKAxNVMKYSAAVNXVEVPETVDWR@KGAVNAIKDQGTCGSCWAFS
CYS2UP8_2   119   SLYLGARTEPVRxxTKAxNVMKYSAAVNXVEVPETVDWR@KGAVNAIK@QG@CGSCWAFS
consensus         SLYLGARTEPVRxxTKAxNVMKYSAAVNxvEVPeTVDWR-KGAVNAIkdQGtCGSCWAFS CYS4_BRANA  129   TAAAVEGINKIVTGELVSLSEQELVDCDKSYNQGCNGGLMDYAFQFImknggIntekdypY
CYS2UP6_1   179   TAAAVEGINKIVTGELVSLSEQELVDCDKSYNQGCNGGLMDYAFQFI
CYS2UP7_1   184   TAAAVEGINKIVTGELVSLSEQELVDCDKSYNQGCNGGLMDYAFQFI
CYS2UP8_2   180   TAAAVEGINKIVTGEL@SLSEQELVDCDKSYNQGCNGGxMDYAFQF
consensus         TAAAVEGINKIVTGELvSLSEQELVDCDKSYNQGCNGGLMDYAFQFimknggIntekdypY
```

FIG. 10-1

CYS2+6 specif cDNA. Seq 04/08/95

Sequencing results

```
AMINO-Res-length    = 2
DELetion-weight     = 1.00
LEngth-factor       = 0
Matching-weight     = 5.00
NUCLEIC-Res-length  = 4
SPread-factor       = 90
```

Clustered order of selected sequences:

```
 9. COT44          (1-1102)
10. CYS2UP6        (1-675)
11. CYS2UP7        (1-691)
12. CYS2UP8        (1-679)
 3. CYS6UP3NCOD    (1-322)
 1. CYS6UP5NCOD    (1-307)
 4. CYS6UP2NCOD    (1-288)
 2. CYS6UP4NCOD    (1-255)
```

FIG. 10-2

Region Alignment: (listed in Clustered order)

```
                                                                                           START
C   COT44         1                                        CAAACATACAATATGGCTTCCTCACCAAAACTCCTCTTT
L                                                          ||||||||||||||||||||||||||||||||||||||||
A   CYS2UP6       1                                        CAAACATACAATATGGCTTCCTCACCAAAACTCCTCTTT
S                                                          ||||||||||||||||||||||||||||||||||||||||
S   CYS2UP7       1      agaaaaccaacAAAACATACAATATGGCTTCGTCAgGAAACTCCTCTTT
2                        |||||||||||||||||||||||||||||||||||||||||||||||||

C   CYS2UP8       1             AAAACATACAATATGGCTTCGTCnnnGAAACTCCTCTTT
L                                ||||||||||||||||||||||||||||||||||||||||
A                                    CYS 6 AUP oligo
S   CYS6UP3NCO    1         TAGAAAAnCCAACAAAACATACAATATGGCTTCGTCAgGAAACTCCTCTTT
S                            ||||||||||||||||||||||||||||||||||||||||||||||||||
2   CYS6UP5NCO    1        TAGAAAACCAACAAAACATACAATATGGCTTCGTCAnGGAAACTCCTCTTT
                             ||||||||||||||||||||||||||||||||||||||||||||||||||
    CYS6UP2NCO    1   aaacTAGAAACATACAATATGGCTTCCTCAaCaAAACTCaTtTTCTTT
                       ||||||||||||||||||||||||||||||||||||||||||||||||
                           gaAcAACCAA    gcCAAACATACAATATGGCTTCCTCAaCaAAACTCaTtTTCTTT
    CYS6UP4NCO     1                   CYS 6 AUP oligo
    (CLASS 6)
    consensus         aaactagaaaaccaacaaaacatacaatatggcttcgtca-cgaaactcctctctt
```

FIG. 10-3

```
COT44      1  ACTTCTCTTATACGTCTCTTCGTTAGCCTCCGGTTATGAGTCCATCATCAGTGACAAC
CYS2UP6   42  ACTTCTCTTATACGTCTCTTCGTTAGCCTCCGGTTATGAGTCCATCATCAGTGACAAC
CYS2UP7   57  ACTTCTCTTGTACGTCTCTTCGTTAGCCTCCGGTGATGAGTCCATCATCAGTGACAAC
CYS2UP8   46  ACTTCTCTTGTACGTCTCTTCATTTCATTAGCCTCCCaGTGATGAGTCCATCATCAACGACAAC
CYS6UP3NCO 23 ACTTCTCTTGTACGTCTCTTCATTTCATTAGCCTCCCnGTGATGAGTCCATCATCAACGACAAC
CYS6UP5NCO 58 ACTTCTCTTGTACGTCTCTTCATTTCATTAGCCTCCAGTGATGAGTCCATCATCAACGACAAC
CYS6UP2NCO 62 ACTTCTCTTGTACGTCTCgTCTTTCATTAGCCTCCgGTGATGAGTCCATCATCAACGACAAC
CYS6UP4NCO 54 ACTTCTCCTaTACGTCCgTTCTTTCATTAGCCTCCggGTGATGAGTCCACtaCCAttaACAAC
consensus     actcctcttgtacgtcttcatttcattagcctcc-gtgatgagtccatcatcaacgacaac
```

```
COT44      77 AGACGAAAGATTCAATAaTTTCAAAGACAACCTAAGATTCATCGATTCTACACAACGAGAAC
CYS2UP6   225 AGACGAAAGATTCAATATTTTCAAAGACAACCTAAGATTCATCGATTCTACACAACGACAAC
CYS2UP7   240 AGACGAAAGATTCAATATTTTCAAAGACAACCTAAGATTCATCGATTCTACACAACGAGAAC
CYS2UP8   229 AGATGAAAGATTCAATATTTTCAAAGACAACCTAAGATTCATCGATTCTACACAACGAGAAC
CYS6UP3NCO 206 AGATGAAAGATTCAATATTTTCAAAGACAACCTAAGATTCATCGATTCTACACAACGAGAAC
CYS6UP5NCO 241 AGATGAAAGATTCAATATTTTCAAAGACAACNACCTAAGATNCANCGATTCTACACAACGAGAAC
CYS6UP2NCO 245 AGATGAAAGATTCAATATTTTCAAAGACNACCTAAGATNCANCG
CYS6UP4NCO 231 AGACGAAAagTTTCAATATTTTCAAA consensus      AGA-GAAAgaTTCAATATTTTCAAAgacaacctaagattcatcgatctacacaacgagaac
```

```
         10         20         30         40         50         60
CTTGTTTGG TTTCCCTGTA AGAAAAGAAA TGTCACCATC ATCGTCTTCT TCCTTTGTTT  60
CTCTCACTTT CTTCTCCCTT CTTCTAGTTT CTTCTCTGAG CTTCTCATCA TCATCTTCCG 120
ATGACATCTC CGAGCTGTTC GACGCTTGGT GCCAGAGACA CGGCAAAACG TACGCTTCGG 180
AGGAAGAGAG ACAACACAGG ATTCGAATCT TTAAAGACAA TCACGACTTC GTCACACGAC 240
ACAACAACAT CGCTAACTCT ACTTACTCTC TCTCACTCAA TGCCTTCGCG GATCTGACTC 300
ACCACGAGTT CAAGGCCTCT CGTCTTGGAG GATTCTCTGC TTCTTCAGCT CCTTTGCTGA 360
TGGCTAAGGG ACAGAGTGTT GAGAACGTTC GGGGAAAGGT TCCAGATTCT GTTGATTGGA 420
GGAAGAAAGG AGCTGTTACT AATGTCAAAG ATCAAGGAAG CTGCGGAGCG TGTTGGTCTT 480
TCTCGGCGAC TGGAGCTATG GAAGGAATCA ACCAGATTGT AACAGGAGAT CTCATCAGCC 540
TCTCTGAGCA AGAACTCATT GATTGTGATA AGTCATACAA CGATGGATGC AATGGTGGTC 600
TCATGGACTA CGCTTTTCAA TTTGTCATTA AAAACCATGG GATTGACACA GAGAAAGATT 660
ATCCTTATCA AGAACGTGAT GGCACCTGTM AGAAAGATAA GTTGAATAGA AAGGTTGTGA 720
CAATTGATAG CTACGCTGGT GTAAAATCAA ATGACGAGAA AGCGTTACTA GAAGCTGTAG 780
```

FIG. 12-2

```
CGGCTCAGCC AGTTAGTGTT GGTATCTGTG GGAGCGAGAG AGCCGTTTCAG TTATACTCTA 840
AGGGAATATT CTCTGGCCCA TGTTCAACAT CATTGGACCA CGCAGTGCTC ATCGTAGGAT 900
ACGGTTCAAA GAACGGTGTT GATTACTGGA TCGTGAAGAA CTCTTGGGGA AAGAGTTGGG 960
GAATGGATGG GTTTATCCAC ATGCAGCGTA ACACCGGCAA CGCAGAAGGA GTATGCGGAA 1020
TCAACATGCT GGCTTCATAT CCCATCAAGA CACATCCAAA CCCTCCTCCA CCGTCCCCTC 1080
CCGGCCCCAC GAAATGCAAC CTTTTCACCT ATGTTCAGC TGATGAGACT TGTTGCTGTG 1140
CGAGAAACTT GTTGGTTTG TGTTTCTCGT GGAAATGCTG CGAGCTAGAG TCTGCTGTGT 1200
GTTGCAAGGA TGGTCGTCAT TGTTGTCCGC GTGATTACCC CGTCTGTGAT ACCACCAGAA 1260
GTCTTTGCCT TAAGAAAACT GGCAATTTCA CAGAGATCAA GCCCTTCTGG AAGAAGAATG 1320
CGTCCAATAA ACTTGGCAAG TTCGAGGAAT GGGTTATGTA AGAGGAAGTT TTCAAACTCT 1380
TTCACACGGT AAGCCTCTTT GGATTCGTTT ATCTATAAGC TGAGAGATGA TTACTTTATA 1440
GCTGTTGTTG TGATATGTAT TATTAGTCTC TTATTTGGAT GTATACAAAC TTTGAATCA 1500
ATAAAAGGTT ACTTGCAGGA CACAATAAAA AAAAAAAAAA AAAAAAAAAA AAAAAAAAAA 1560
AAAAAAAAAA AAAAAAA 1577
```

FIG. 13-1

```
            10         20         30         40         50         60
            |          |          |          |          |          |
AAAGCTCTT CTTGTTTCGG TTTCCCTGTA AGGAAAAGAA ATGTCACCAT CATCGTCTTC   60
TTCCTTTGTC TCTATCACTT TCTTCTCCCT TCTTCTAGTT TCTTCTCTGA GCTTCCCATC  120
ATCATCTTCC GATGACATCT CCGAGCTGTT CGACGCTTGG TGCCAGAGAC ACGGCAAAAC  180
GTACGCTTCG GAAGAAGAGA GACAACACAG GATTGAAATC TTTAGAGACA ATCACGACTT  240
CGTCACACGA CACAACGGCA TCGCTAACTC TACTTACTCT CTCTCACTCA ATGCCTTCGC  300
GGATCTGACT CACCACGAGT TCAAGGCCTC TCGTCTTGGA CTCTCTGCTT CTTCAGCTCC  360
GTTGCTGGTG GCTAAGGGAG AAAGTGTTGA GAACGTTGGG GGCAAAGTTC CAGATTCTGT  420
TGATTGGAGG AAGAAAGGAG CTGTTACTAA TGTCAAAGAT CAAGGAAGCT GCGGAGCGTG  480
TTGGTCTTTC TCGGCGACTG GAGCAATGGA AGGAATCAAC CAGATTGTAA CAGGAGATCT  540
CATCAGCCTC TCTGAGCAGG AACTAATTGA TCCTACAACG ATGGATGCAA  600
TGGTGGTCTC ATGGACTACG CTTTTCAATT TGTCATTAAA AACCATGGAA TCGACACAGA  660
GAAAGATTAT CCTTATCAAG AACGTGATGG CACCTGTAAA AAAGATAAGT TGAAAAGAAA  720
GGTTGTGACA ATTGATAGCT ATGCTGGCGT AAAATCAAAC GACGAGAAAG CGTTACTGGA  780
```

FIG. 13-2

```
AGCTGTAGCG GCTCAGCCAG TTAGTGTTGG CATCTGTGGC AGCGAGAGAG CGTTTCAGCT 840
ATACTCTAAG GGAATATTCT CTGGCCCATG TTCAACATCA TTGGACCACG CAGTGCTCAT 900
CGTAGGATAC GGTTCACAGA ACGGTGTTGA TTACTGGATC GTGAAGAACT CTTGGGAAA 960
GAGTTGGGGT ATGGATGGGT TTATGCACAT GCAGCGTAAC ACCGGCAACT CGGAAGGAGT 1020
ATGTGGAATC AATATGCTCG CTTCGTATCC CATCAAGACA CATCCAAACC CTCCTCCACC 1080
GTCCCCTTCC GGCCCCACGA AATGCAACCT TTTCACCTAT TGTGCAGCTG ATGAGACTTG 1140
TTGCTGTGCG AGAAACTTGT TTGGTTTGTG TTTCTCGTGG AAATGCCGCG AGCTAGAGTC 1200
TGCTGTGTGT TGTAAGGATG GTCGTCATTG TTGTCCTCGT GATTACCCCG TCTGTGATAC 1260
AACCAGAAGT CTTTGCCTAA AGAAAACTGG CAATTTCACA GAGATCAAAC CCTTCTGGAA 1320
GAAGAATGCG TCCAATAAAC TTGGCAAGTT CGAGGAATGG GTTATGTAAG AGAAGTTTTT 1380
TAAACTCTTC CACACGGAAG CCTCTTTGGA TTCGTTATGT ATAAGCTGAG AGATGATTAT 1440
TTTATAGCTG TTGTTGTGAT ATGTATTATT AGTATCTCAT TTGGATGTAT ACAAACTTTT 1500
GAATCAATAA AGGGTATCTG CAGGACACAT TAAATAAAAA AAAAAAAAAA AAA 1553
```

FIG. 14-1

```
         10         20         30         40         50         60
         |          |          |          |          |          |
CAACTATCAA AACTAGAAAA CCAACAAAAC AAACATACAA TATGGCTTCG TCAGCGAAAC  60
TCCTCTCTT ACTTCTCTTG TACGTCTTCA TTTCATTAGC CTCCAGTGAT GAGTCCATCA  120
TCAACGACAA CCATCTCATT CTTCCATCTG ACCGCTCGTG GAGAACCGAT GAAGAAGTGA  180
TGTCCATCTA CTTAAAATGG TCCTTGGAGC ACGGGAAAAG TAACAGCAAC AGCAACGGTA  240
TTATCAACCA ACAAGATGAA AGATTCAATA TTTTCAAAGA CAACCTAAGA TTCATCGATC  300
TACACAACGA GAACAACAAG AACGCTACTT ACAAGCTTGG TCTAACCATA TTCGCTGATC  360
TCACTAACGA TGAGTACCGG AGTTTATACC TCGGGGCAAG AACCGAGCCT GTCCGCCGCA  420
TCACTAAGGC CAAGAACGTT AACATGAAAT ACTCAGCCGC AGTAAACGAC GTGGAGGTTC  480
CGGAGACGGT TGACTGGAGA CAGAAAGGAG CCGTTAATGC CATTAAAAAC CAAGGATCTT  540
GCGGAAGTTG TTGGGCGTTT TCAACAGCTG CAGCAGTAGA AGGCATAAAC AAGATCGTAA  600
CAGGAGAGCT CATATCTCTG TCCGAACAAG AACTTGTCGA CTGCGACAAA TCATACAACC  660
```

FIG. 14-2

```
AAGGCTGTAA CGGCGGTCTA ATGGATTATG CTTTTCAATT CATCATGAAA AACGGCGGAT 720
TAAACACCGA GCAAGACTAT CCTTACCACG GAACCAATGG CAAATGCAAC TCTTTACTTA 780
AAAATTCGAG AGTTGTGACT ATCGATGGAT ACGAAGATGT TCCTAGTAAA GATGAAACCG 840
CGTTGAAGAG AGCAGTTTCG TACCAGCCTG TGAGTGTTGC TATTGATGCT GGTGGAAGAG 900
CTTTCCAACA TTACCAATCT GGAATCTTCA CTGGAAAGTG TGGTACGACT ATGGATCACG 960
CTGTTGTGGC GGTTGGTTAT GGATCAGAGA ACGGTGTTGA CTATTGGATT GTACGTAACT 1020
CTTGGGGTAC AAGCTGGGGA GAGGATGGTT ACATTAGGAT GGAGAGAAAC GTGGCGTCCA 1080
AATCCGGTAA GTGTGGGATT GCGATTGAAG CCTCGTATCC GGTTAAGTAC AGCCCAAACC 1140
CGGTTCGTGG AACCAGCAGT GTTGAAGTT ATCTCATGCA GTAATCAAAT 1200
TGGGATTGTT ATAAGTTAAA TTAATCTTGT ATTATTGTTT GTATGTATAG TATTTCGAAA 1260
AAAATTGATT CACCATAGGG ATTTAATCTG TATAAATCTC TATGTTGGTC AATATCATTT 1320
CATTCAAAGA ATATTTGCTT TGGCTTGATT ATGTATTAAG AGAAATATAA TAAAAAAAAA 1380
AAAAAAAAAA 1390
```

FIG. 15-1

```
          10         20         30         40         50         60
          |          |          |          |          |          |
CAACTATCAA AACTAGAAAA CCAACAAAAC AAACATACAA TATGGCTTCC TCACCAAAAC   60
TCCTCTCTTT ACTTCTCTTA TACGTCTTCG TTTCGTTAGC CTCCGGTTAT GAGTCCATCA  120
TCAGTGACAA CCATCTCAGT CTTCCATCTG ACCGTTCGTG GAGAACCGAT GAAGAAGTGA  180
TATCCATCTA CTTAAGATGG TCCTTGGAGC ACGGGAAAAG TAACAGCAAC AGCAACGGTA  240
TTATCAACCA ACAAGACGAA AGATTCAATA TTTTCAAAGA CAACCTAAGA TTCATCGATC  300
TACACAACGA GAACAACAAG AACGCTACTT ACAAGCTTGG TCTAACCATA TTCGCTGATC  360
TCACTAACGA TGAGTACCGG AGTTTATACC TCGGGGCAAG AACCGAGCCT GTCCGCCGCA  420
TCACTAAGGC CAAGAACGTT AACATGAAAT ACTCAGCCGC AGTAAACGAC GTGGAGGTTC  480
CGGAGACGGT TGACTGGAGA AAGAAAGGAG CCGTTAATGC CATTAAAGAC CAAGGAACTT  540
GCGGGAAGTTG TTGGGCGTTT TCAACAGCTG CAGCAGTAGA AGGTATAAAC AAGATCGTAA  600
CAGGAGAACT CGTATCTTTG TCCGAACAAG AACTTGTCGA CTGCGACAAA TCGTACAACC  660
AAGGCTGTAA CGGCGGTCTA ATGGATTATG CTTTTCAATT CATAATGAAA AACGGGGGAT  720
```

FIG. 15-2

```
TAAACACCGA GAAAGACTAT CCTTACCACG GAACCAATGG CAAATGCAAC TCTTTACTTA 780
AGAATTCAAG AGTTGTAACT ATCGATGGAT ACGAAGATGT TCCTAGTAAA GATGAAACCG 840
CGTTGAAGAG AGCAGTTTCA TACCAGCCTG TGAGTGTTGC TATTGATGCT GGTGGAAGAG 900
CTTCCAACA TTACCAATCT GGAATCTTCA CTGGAAAGTG TGGTACGAAT ATGGATCACG 960
CTGTGGTGGC GGTTGGTTAT GGGTCAGAGA ACGGCGTTGA CTATTGGATT GTACGTAACT 1020
CTTGGGGTAC ACGTTGGGGA GAGGATGGTT ACATTAGGAT GGAGAGAAAC GTGGCGTCTA 1080
AATCCGGTAA GTGTGGGATT GCGATAGAAG CCTCGTATCC GGTTAAGTAC AGCCCAAACC 1140
CGGTTCGTGG AACCAGCAGT GTTTGAAGTT AACAAAAAGA ATCTCATGCA GTAATCAAAT 1200
TGGGATTGTT ATAAGTTAAA TTAATCTTGT ATTATTGTTT GTATGTATAG TATTTCGGAA 1260
AAAAAAATGA TTCACCATAG GGATTTAATC TGTATAAATC TCTAGGTTGG TCAAATATCA 1320
TTTCATTCAA AGAATATTTG McTTTGACTT GATTATGTAT AAGAGAAAT ATAATAAAAT 1380
GGTATATTTC TCAACAGCAT TGGTTTCGCT GAAAAAAAAA AAAAAAAAA AAAA 1434
```

FIG. 16-1

```
AGAAACCAA CAAAACAAAC ATACAATATG GCTTCGTCAG CGAAACTCCT CTCTTTACTT    60
CTCTTGTACG TCTTCATTTC ATTAGCCTCC AGTGATGAGT CCATCATCAA CGACAACCAT   120
CTCATTCTTC CATCTGACCG CTCGTGGAGA ACCGATGAAG AAGTGATGTC CATCTACTTA   180
AAATGGTCCT TGGAGCACGG GAAAAGTAAC AGCAACAGCA ACGGTATTAT CAACCAACAA   240
GATGAAAGAT TCAATATTTT CAAAGACAAC CTAAGATTCA TCGATCTACA CAACGAGAAC   300
AACAAGAACG CTACTTACAA GCTTGGTCTA ACCATATTCG CTGATCTCAC TAACGATGAG   360
TACCGGGAGTT TATACCTCGG GGCAAGAACC GAGCCTGTCC GCCGCATCAC TAAGGCCAAG   420
AACGTTAACA TGAAATACTC AGCCGCAGTA AACGACGTGG AGGTTCCGGA GACGGTTGAC   480
TGGAGACAGA AAGGAGCCGT TAATGCCATT AAAAACCAAG GATCTTGCGG AAGTTGTTGG   540
GCGTTTTCAA CAGCTGCAGC AGTAGAAGGC ATAAACAAGA TCGTAACAGG AGAGCTCATA   600
TCTCTGTCCG AACAAGAACT TGTCGACTGC GACAAATCAT ACAACCAAGG CTGTAACGGC   660
GGTCTAATGG ATTATGCTTT TCAATTCATC ATGAAAAACG GCGGATTAAA CACCGAGCAA   720
```

FIG. 16-2

```
GACTATCCTT ACCACGGAAC CAATGGCAAA TGCAACTCTT TACTTAAAAA TTCGAGAGTT  780
GTGACTATCG ATGGATACGA AGATGTTCCT AGTAAAGATG AAACCGCGTT GAAGAGAGCA  840
GTTTCGTACC AGCCTGTGAG TGTTGCTATT GATGCTGGTG GAAGAGCTTT CCAACATTAC  900
CAATCTGGAA TCTTCACTGG AAAGTGTGGT ACGACTATGG ATCACGCTGT TGTGGCGGGTT  960
GGTTATGGAT CAGAGAACGG TGTTGACTAT TGGATTGTAC GTAACTCTTG GGGTACAAGC 1020
TGGGAGAGG ATGGTTACAT TAGGATGGAG AGAAACGTGG CGTCCAAATC CGGTAAGTGT 1080
GGGATTGCGA TTGAAGCCTC GTATCCGGTT AAGTACAGCC CAAACCCGGT TCGTGGAACC 1140
AGCAGTGTTT GAAGTTAACA AAAAGAATCT CATGCAGTAA TCAAATTGGG ATTGTTATAA 1200
GTTAAATTAA TCTTGTATTA TTGTTTGTAT GTATAGTATT TCGAAAAAAA TTGATTCACC 1260
ATAGGGATTT AATCTGTATA AATCTCTATG TTGGTCAATA TCATTTCATT CAAAGAATAT 1320
TTGCTTTGGC TTGATTATGT ATTAAGAGAA ATATAATAAA AATGATATAT TTCTCAAAAA 1380
AAAAAAAAAA AAAAAAAAAA AAAAAAAAAA AAAAAAAAAA AAAAAAAAAA AAAAAAAAAA 1440
A 1441
```

FIG. 17-1

```
          10         20         30         40         50         60
CAGAACTAGA ACAACCAAGC CAAACATACA ATATGGCTTC CTCAACAAAA CTCATTTCTT   60
TACTTCTCCT ATACGTCGTC GTTTCATTAG CCTCCGGTGA TGAGTCCACT ACCATTAACA  120
ACCATCTCAA TCTTCCATCG GACGGCTCAT GGAGAACCGA TGAAGAAGTG AGGTCCATCT  180
ACTTACAGTG GTGTGCGGAG CACGGGAAAA CTAGCAACAA CAACGGTATC GTCAACCAAC  240
AAGACGAAAA GTTCAATATT TTCAAAGACA ACCTAAGGTT CATTGATCTA CACAATGAGA  300
ACAACAAGAA CGCTACTTAC AAGCTTGGTC TCACCATATT CTCTGATCTC ACTAACGATG  360
AGTACCGGAG GTTATACCTC GGGGCAAGAA CCGAGTCTGT CCGCCGCATC ACTAAGGCCA  420
AGAACGTTAA CATGAAATAC TCGGCCGCAG TAAACGACGT GGAGGTTCCG GAGACGGTTG  480
ATTGGAGACG GAAAGGAGCC GTTAATGCCA TTAAAAACCA AGGAACTTGC GGAAGTTGTT  540
GGGCGTTTTC GACAGCTGCA GCAGTAGAAG GTATAAACAA GATCGTAACA GGAGAACTCA  600
TATCTCTGTC CGAACAAGAA CTTGTCGACT GCGACAGATC CTACAACCAA GGCTGCAACG  660
GTGGTTTAAT GGACTATGCT TTTCAATTCA TCATGAAAAA CGGCGGGTTTG AACACCGAGC  720
```

FIG. 17-2

```
AAGATTATCC TTACCGTGGT TCCAATGGAA AATGCAATTC TTTACTGAAG AATTCAAGAG   780
TTGTAACTAT TGATGGTTAC GAAGATGTTC CTACTGAAGA TGAAACGGGCG TTGAAGAGAG   840
CAGTTTCATA CCAGCCCGTG AGTGTTGCCA TTGAAGCTGG TGGAAGAGTT TTCCAACATT   900
ACCAATCGGG GATCTTCACT GGAAAGTGTG GGACAAATCT AGATCATGCA GTGGTGGCTG   960
TTGGTTATGG TTCAGAGAAC GGTATTGACT ATTGGATTGT AAGGAACTCG TGGGGTACAC  1020
GTTGGGGAGA GGATGGTTAC ATTAGGATGG AGAGAAACTT GGCAAGGTCC AAGTCCGGCA  1080
AGTGTGGAAT TGCGGGTTGAA GCCTCGTACC CGGTTAAGTA CAGTCCAAAC CCGGTTCGTG  1140
GAACCAGCAG TGTTTGAAGT TTTTAAAATA AAACTCAATT GGGAGTTTTA TAACTAAGAT  1200
TTAATCTCAT ATTATTGTTT GTATGTATAG TATATCAAAA AAGAAGGTAT TCATTTCGTT  1260
ATACGGATTT AGTCTGTATA AATCCTTATG TCGATCAATA TGATATAATAAA CAAAGAAAGA  1320
TTGATTTGGT TGTTTATGTA TTAAGAGAAG TATAATAAAA AAAAAAAAAA CTCTTAAAAA  1380
AAAAAAAAAA AAAAAAAAAA AAAAAAAAAA AAAAAAAAAA AAAAAAAAAA AAAAAAAAAA  1440
AAAAAAAAAA AAAAAAAAAA AAAA 1474
```

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | | | | 330 | | | | | | 340 | | | | | | 350 | | | | | | 360 | | | |
| 299 | Y | W | I | V | K | N | S | W | G | K | S | W | G | F | I | H | M | Q | R | N | T | G | N | A | E | - | G | V | C | G | I | N | M | L | A | S | Y | CDCYS12.P |
| 298 | Y | W | I | V | K | N | S | W | G | K | S | W | G | F | M | H | M | Q | R | N | T | G | N | E | - | G | V | C | G | I | H | M | L | A | S | Y | CDCYS14.P |
| 321 | Y | W | I | V | R | N | S | W | G | T | S | W | G | Y | I | R | M | E | R | N | V | A | - | S | K | S | G | K | C | G | I | A | I | E | A | S | Y | CDCYS22.P |
| 321 | Y | W | I | V | R | N | S | W | G | T | S | W | G | Y | I | R | M | E | R | N | V | A | - | S | K | S | G | K | C | G | I | A | I | E | A | S | Y | CDCYS24.P |
| 321 | Y | W | I | V | R | N | S | W | G | T | R | W | G | Y | I | R | M | E | R | N | V | A | - | S | K | S | G | K | C | G | I | A | A | E | A | S | Y | CDCYS25.P |
| 320 | Y | W | I | V | R | N | S | W | G | T | R | W | G | Y | I | R | M | E | R | N | L | A | R | - | S | K | S | G | K | C | G | I | A | V | E | A | S | Y | CDCYS66.P |
| 275 | Y | W | I | V | R | N | S | W | G | T | R | W | G | Y | I | H | M | E | R | N | V | A | - | S | K | S | G | K | C | G | I | A | I | E | A | S | Y | COT44.PRO |
| | Y | W | I | V | R | N | S | W | G | T | S | W | G | Y | I | R | M | E | R | N | V | A | - | S | K | S | G | K | C | G | I | A | I | E | A | S | Y | Majority |

| | | | | | | | | | | | | | | | | | | | | | | | |
|---|---|---|---|---|---|---|---|---|---|---|---|---|---|---|---|---|---|---|---|---|---|---|---|
| | | | 370 | | | | | | 380 | | | | | | 390 | | | | | | 400 | | |
| 338 | P | V | K | Y | S | P | N | P | P | V | R | G | T | S | S | P | G | P | T | K | C | N | L | F | T | Y | C | S | A | D | E | T | C | C | A | R | N | L | F | G | L | CDCYS12.P |
| 337 | P | I | K | T | H | P | N | P | P | P | V | R | G | T | S | S | P | G | P | T | K | C | N | L | F | T | Y | C | A | A | D | E | T | C | C | A | R | N | L | F | G | L | CDCYS14.P |
| 360 | P | V | K | Y | S | P | N | P | P | P | V | R | G | T | S | S | P | S | | | | | | | | | | | | | | | | | | | | | | | | | CDCYS22.P |
| 360 | P | V | K | Y | S | P | N | P | P | P | V | R | G | T | S | S | P | S | | | | | | | | | | | | | | | | | | | | | | | | | CDCYS24.P |
| 360 | P | V | K | Y | S | P | N | P | P | P | V | R | G | T | S | S | | | | | | | | | | | | | | | | | | | | | | | | | | | CDCYS25.P |
| 360 | P | V | K | Y | S | P | N | P | P | P | V | R | G | T | S | S | | | | | | | | | | | | | | | | | | | | | | | | | | | CDCYS66.P |
| 314 | P | V | K | Y | S | P | N | P | P | P | V | R | G | T | S | S | | | | | | | | | | | | | | | | | | | | | | | | | | | COT44.PRO |
| | P | V | K | Y | S | P | N | P | P | P | V | R | G | T | S | S | | | | | | | | | | | | | | | | | | | | | | | | | | | Majority |

FIG. 18-6

|  |  | 410 |  |  |  | 420 |  |  |  | 430 |  |  |  | 440 |  |  |
|---|---|---|---|---|---|---|---|---|---|---|---|---|---|---|---|---|---|
| 378 | C F S W K C C E L E S A V C C K D G R H C C P R D Y P V C D T T R S L C L K K T | CDCYS12.P |
| 377 | C F S W K C C R E L E S A V C C K D G R H C C P R D Y P V C D T T R S L C L K K T | CDCYS14.P |
| 374 | - - - - - - - - - - - - - - - - - - - - - - - - - - - - - - - - - - - - - | CDCYS22.P |
| 374 | - - - - - - - - - - - - - - - - - - - - - - - - - - - - - - - - - - - - - | CDCYS24.P |
| 374 | - - - - - - - - - - - - - - - - - - - - - - - - - - - - - - - - - - - - - | CDCYS25.P |
| 374 | - - - - - - - - - - - - - - - - - - - - - - - - - - - - - - - - - - - - - | CDCYS66.P |
| 328 | - - - - - - - - - - - - - - - - - - - - - - - - - - - - - - - - - - - - - | COT44.PRO |

Majority

|  | V |
|---|---|

|  | 450 |  |  |  | 460 |  |  |
|---|---|---|---|---|---|---|---|
| 418 | G N F T E I K P F W K K N A S N K L G K F E E W V M . | CDCYS12.P |
| 417 | G N F T E I K P F W K K N A S N K L G K F E E W V M . | CDCYS14.P |
| 374 | - - - - - - - - - - - - - - - - - - - - V | CDCYS22.P |
| 374 | - - - - - - - - - - - - - - - - - - - - V | CDCYS24.P |
| 374 | - - - - - - - - - - - - - - - - - - - - V | CDCYS25.P |
| 374 | - - - - - - - - - - - - - - - - - - - - V | CDCYS66.P |
| 328 | - - - - - - - - - - - - - - - - - - - - - V | COT44.PRO |

Decoration 'Decoration #1': Box residues that match the Consensus exactly.

FIG. 19-1

```
Contig 2:
Contig Length:             1644 bases
Average Length/Sequence:    449 bases
Total Sequence Length:     9448 bases
Top Strand:                  11 sequences
Bottom Strand:               10 sequences
Total:                       21 sequences
```

```
         10         20         30         40         50         60
BamHI
GATCTACTTC GGCTAAAAATT ACAGTCTCAA CAACTACACA AGTAGCTCAG AGAATCAGCA    60
GAAACAGTTT GCTACCCAGA AGAACCCTAA TTCAACAGGG GAGATAAAAA AAAAGTAAAA   120
AGAGTACACT GAGAGAATAA GGATGATCAC CTCGAGTTTT CTGATGAAGA AGGGAACCA    180
AAGTGAAGCA TTTGATGATT GTCTTCTTCG ATTGATGAGC TTCTTCACAT CTAAAAAAGT   240
ATACTTTTTT CTCTCTCGAT GATTGATGAT CAGATAGAAG AAGAAAAAGA TAAACCTTAG   300
ATTTTTTTT GTTGTTCACT CTTCACTTGG TCTTCTACTT CTTCTTCTTC CACCTTTGTT   360
TGTCTCTACC GTTTGAATC AAGCGAGATT ATGAAAGGAC AACTCATCAT TATCACCATT   420
GATATCTTTA ATCCTTTATT TATATATTTA TTTACCCATT TAATAGTTTT TTATGCTTAG   480
```

FIG. 19-2

```
TTATGTATTT AGAGAAATTA CTTTATACTG TTTAGCCAGG AATACATATA TCAGTTAAAC 540
AATAGTGACC TGTTAATTAC TAAAATTTAA TAAAGTAGAG ATGTCACCGA ATATTGTGAC 600
ATTAATAAGA AGCAGTTTTC AAACCTTTTT AGCCTACCTA ATATAACCTG ATATTCAAAC 660
TTTTGATCTA CGACCTTATT TCAACTCTAG TAGTTGTAGA TACTTACAAA ATAAAATGTC 720
ATCGATTTCA AGTAAACTAA ACATGCATTT ACATGGGACA TATTCTCTAA TGTTATTATA 780
CCTTCTGATA AAACAACAAT AAATGTTCTT AGAATTGGAA AAATACTATT TTTTCTAAAG 840
AGAAAAAGGC ACGTTCGTAT TTGCTGATTA TTATATACAG TAGTAGTAAA AGTAGCCTT 900
TACTTGTCGA CAGTTAGGTA AAGACTGAAC GCCACGCCAC ACTATCTTCT CTTTTCAAC 960
AGTGTGAAGA TGTGTTTGTT TCTTTGTCAC TCGTTCTATT CTATCATCAT CATCTTAGGT 1020
CACTAGCCAC ACTTATGTTT TTTCTAAAGT ATACACTGGA AAGATTGGTA AATGTATTTG 1080
ATAATATATA CTACTACTCT GATGTAGTAA TTCTAAAACT AAAGCATATT TCTTGGTTAC 1140
TTACTAGGTA CTACTACTCT CTGGTCTCCG CGTGATCTTA TATTTATTAT ACTAATTGAA 1200
ATTAAAAAGC ATATACTAAA AAGGGTTAAT GCCATAAAGT CGTAAGTAGG TCCAACAAGG 1260
AGTGGTCTTA TTAACCTAAA AAAGGTTGAA AGTAGCTTTC TTTTTGCTTA CAAAAGTATA 1320
TGCTATGTTT ACATTTAACA ATGAATTTAT TGTTGACCAA AAAAACAAAC AATGATTTAT 1380
TTAGCTAAGA GTAGCATTTG AATTTTGATT GTAATGGGCC TAGCCTGTCT GGCCCAATCA 1440
TTCATAACCG GGTCTAATCA TTAATAAAAA GCCCTTCAGC ATTCAACGCT AAACGCTTAT 1500
TACAAACGCT AGCCGCGCGT TTTGTAAACG TTGTTGCATC CTTACTGGCT AAAGTCTCCT 1560
TATTACTAGG ACAAACTATC TAATCCACGA CGACGACCAA ACAAAAGCTC TTCTTGTTTT 1620
GGTTTCCCTG TAAGAAAAGA A[ATG] 1644
                        START
```

FIG. 20A-1

```
Contig 5:
Contig Length:              3997 bases
Average Length/Sequence:     452 bases
Total Sequence Length:     21697 bases
Top Strand:                   28 sequences
Bottom Strand:                20 sequences
Total:                        48 sequences
```

```
HindIII     10         20         30         40         50         60
AAGCTTGATG GGGTTGTGAT GTTTGCGGAT GATAGTAACA TGCATAGTAT GGAGTTTTTC  60
GATGAGATTC AGAACGTGAA GTGGTTCGGT GCTGTTCCG  TTGGGATATT AGCCGCATTCG 120
GGGAATGCGG AAGAGATGGT TATGTCGATG GATAAGAGAA GAGAGATGGA GGAAGAAGAG 180
AGCTCTTCGT TATCTTCGTT ACCAGTACAA GGTCCTGCGT GTAACGCGAC CGATAAGCTG 240
```

FIG. 20A-2

```
ATCGGTTGGC ATGTTTTCAA TACGTTGCCA TACGCGGGGA AGAGTGCGGT TTACATAGAC    300
GATGTAGCTG CGGTTTTGCC GCAGAAGCTG GAGTGGTGTG GGTTTGTATT GAACTCGAGG    360
ATTCTTTGGG ATGAGGCTGA GAGTAAGCCG GAGTGGGTTA AGGAGTTTGG GTTGTTGAAC    420
GAGAACGAAG gCGTGGAGAG TCCTTTGTCT CTGTTGAATG ATCCTTCGAT GGTTGAGCCT    480
CTTGGAAGCT GTGGAAGACA GGTTCTGCTT TGGTGGCTTC GTGTCGAAGC ACGCGCTGAT    540
AGCAAGTTCC CTCCCGGGTA TATGCCTTCT TTTGCTCTCA AGATGTTAAC TAATTAGCTC    600
AATGTTCAAA CTAGGAGTTA GTTAGTGATG TTTGGTTCTG TTTTTGTTAT ATGAGTGCAG    660
ATGGGTGATT TAGAAATCAC AGTGGCGGCT AAACGAACGC CATGGCCAGA                720
TGTTCCACCT GATCCTCCGT CTAAAAAGAA AGATCAAATG TCATTATCCC AAGGCAACAA    780
CAACGTGGTG GAGCCACCTA AGCACCAGCA GCAGCAGCAA CAACAGCAAC GTTCTAGCAA    840
AGTGCGGAAA CCGAAACGCA GAAGTAAGCA AAATAAACAC GAAGCTAAAC CAACTGATAC    900
GACAACACAA GTTTCTTCTT CCACTAAACA TCATCAAGAA AGAAACTGAG GAAGAAGAAA    960
GATCATTTCT ACTATTTTAT TATCATTCAT TTGTTTGCCA AAGTTTTATA GAGAATGTC   1020
AAGAGATCAT CTTATTCTCC TCCAGATACC GCGAATAGTA AGAATCAACG GTGAGGAAGC   1080
AAGAACAAAG GCTTAGATTT TATGATGATG GAGCCCCCAC AGCAAAAGGG TATACGGGTT   1140
TTTAGGGGAA TTGATGATCA TTCGTTTATT TTCGATATAT CTTTCTTTTG GTCTTTATAA   1200
```

FIG. 20A-3

```
GAACTTATCT GTATTAGTAA CAAAGAATTA TTTGTTTCAT TGTTCTTGAA GTTGCAAAAA 1260
AAGGCTTAGA AACAAAAACT TTGGGTTGTA TAGTTTCTTT TGTAAGCATA TTTCTCAATC 1320
CATTTCTGTT TTATCCCCCA ATTAATCCAC ACTATGGACC TAAAAGTTCA AAGCCTCAAT 1380
TTACTCCTGC GAGTTCGTTT CACAGAAATT AATTACACTT TTTTATTATT CTTCATAAGG 1440
AAACAATACA TATGTATTTA TATGTATTT TCTAAAGAAA TATTGGAGAT GAAGACATTG 1500
GAAAAGATAC CTTCGTAAAA AAGAATTGTG AAGAAAGTAA ATACAAAACA GAATCATTCT 1560
TTTGTGAAAG TTGAGACAAA GACTGAAAAC AGATTCATAA CTGAAATAAT GGAGGATTGG 1620
GCGGTTTTGT CAGAACATCA CATGTCTTCT TTAACCACTT TTCCCTCACT CTATTAGATT 1680
TTTTCTTAG TACACTGCGG TCATAGCCTA TAGGTATGTA CTTTGACCAC TATAAACAGG 1740
ATTGAGTTAG GGTTTCTTCT AATTATGGGA TTTTATTACG TTTTCAACCT CTATTTCTT 1800
CGGATTAGGT TTATTTAGAT GTTTTTTGCT TCATTTTCT AACTATTTAG TTTTAGAGAG 1860
GAAACACAAG ATGTTAAACC CATTAGTGAA CCAAAATTTA AGCAGGTGAC TAGAGTAAAC 1920
CAAACATATC TAATAGTATG GAATTTTGTC TTTACTACTT AATATGAGGT AATCAATCCG 1980
GATAGAAGTG AAATTAACGA AAAATATCCT ATTTACTTATAA AATCAAATTT 2040
ATATTATGCG ATTTTTAACA TTCTTTGGAA CAGTATTAGT TCAGTTGCTT AAACGAAAAC 2100
```

FIG. 20B-1

```
            2110        2120        2130        2140        2150        2160
              |           |           |           |           |           |
CAAACAGTCG GTGGAACTCC CATGCTTCGT AGCTTAGCTG CCCATACWAA ACGATATCAA 2160
AACCAAACCG AATTATAAAA CAGAAACGGT CACCTTTAGT TGTACCATGT CAGAAACACG 2220
AGCGAGGCAC TTGTGTTTCT TAAACCTTAT CAAAAGCCAC CACTCCGGAT TGAAACTTGG 2280
TTAAAGACAA CTCTTTGCCT CCCATTTCCT CCAATCACCT TTTTTCTTG TTGTTAAAAT 2340
GTCTTCATAA AGTATGCTCG TATGAGAAAG GATCAAATGC AACGGTCAGG ATGGGCACC 2400
GCCTCGTGAC AAGAGGATCT GCCGTGAAAC TGGAACATCA TGTCCACCCA TTCATTCTAG 2460
ATTCTTCTAT ATGAATCTTC AACTTTAATA TATCTATTAA ATATACATGC AGAGCTCTGT 2520
ACGTATATTT ATTATTATA TCATCAACTA TAAAAAAAAA GACCACGCAT AATAGAAACT 2580
ATATTCAGAC TACAGTTTTG AATCATAAATG TAAATATATA GAGGAATAAT ATTCCTCATA 2640
TTTTGATAAA ATAGATTATT TTCCACTCAC CAGAAAGACA GAACCATATT TTCTAGTGGT 2700
CGATATATAG AATGTAAATA AATTTAGATA ACTAAAAAGCT ATCATTCTAT ATATGTATCT 2760
TTAAACAAAA AATTTAGATA GGTTTTCCCA TACGTACGTA CCTTATGAAA CTTTTTCGAG 2820
GTAGTTGCAA CTCTTCTATT CATTGTTTTT CCTTCGTCCC ATATATATAG ATTATTGGAA 2880
```

FIG. 20B-2

```
ATTGATGTAA CGTAGATTCA GAAATTCACA TCACAGACAT CTATACCTAT TTATACGGCT 2940
CTCAAACCAT AATTGTCACA ATGCATGTCT GTGGATTTAA CTTTACAACT TACTAAATAC 3000
TCCAATTAGA TTCGACGTAA AGAAATTAAT CACACGAAAA AGATGCAGCT ATTTCGTTAA 3060
AAGTTGATCC TCAAGTGACA TCATGCTGCT TCGAAATGCT GAAAAGATTT AATGATCTTC 3120
ATGTTCCCAT GTGTTCGGAA TTGAACGACT CTGATGATAT GTGGTCGGTA GCCAAAAAAA 3180
ACGCGGTTCA AAGCGAATTG TTTGTTTTGC TATATACTAT TGACGTTATA AAGTCAAAAA 3240
TAAACCGCTT ACAAGATGGT TCTGACCGCT TCAAAAATAA ACGCTCTGTG TATATATATT 3300
ATCGTCTACT GTATGCAGGA TATATGGTAG CTATTTACGT CAAATATGAG TAGATCAGCG 3360
TTGATCAAAC ATAAACGTAA ATCTCTCGTG AGTCGATAGA TGTTGATGTA AACAACAAAC 3420
CACGGAAAAT AAATAACTGC AAAAAATATA AAAGAATGG TGTTATTATT TAACCCAAAA 3480
ATTGTATTAT CATACTTACA CGAAGAAAAT TACGTACATC TACGAGATAA TTCCATGAGA 3540
AAAGAATAGT AAACTCTTTG AATTACAGAC GAATGGTTTG AACCCCGTAG ATCTTTGAGT 3600
TTGAATTGTA TTTAAGAGCA TGATACTACG ATGTTGTATT CTTTTTTAGA TCAGTGAATC 3660
GTAGTTTTTT CCTATTTACC ATCCGATTGT CCGAATAAAA TAATAATTAT CTCCAAAATT 3720
AATAAATTTA GATTTCTAAA ATCAAACATA AATATCTAGT AATTAAAAGT GAAGATATTA 3780
TATATTTAGT AAACAGTTGT CCATATTTCG GCAAAAAAAA TCCATTTGAA ACGTCCACTA 3840
TCTTGCATGC CCATTATTAC TTTTTATTAT AATACCAACT TGAAATATTA AAATACCTAA 3900
ACTTTGGTTA TAAATAGTTT CACATTCTTG TCCCACCAAA AATCAAGCCA TACCAACTAT 3960
CAAAACTAGA AAACCAACAA AACAAACATA CAAT ATG 3997
                                    START
```

FIG. 21-1

```
Contig 2:
Contig Length:              2000 bases
Average Length/Sequence:     413 bases
Total Sequence Length:      9920 bases
Top Strand:                   14 sequences
Bottom Strand:                10 sequences
Total:                        24 sequences
```

```
       BamHI    10         20         30         40         50         60
       ----     |          |          |          |          |          |
       GGATCCCACA CATAACTGTA ATGTTTCAAT ACTCACGTGT AACTTTGATC ATCGAAACCT  60
       ATTTAGTAAA ATCCGCATTC TGGCCCAATA AAACTTATAA GTGGGCTAAA TCTCTTTTGT 120
       ATGTATCTAG GATTTTTATA GTACTATGTC TCCACCGATA AACCGAAGCG TTACCCTTTT 180
       AGCTTATCAA AAAAAATTCT GAAACTTTTC ATTTTCACCT CTCTATATCT CCAACGATCA 240
```

FIG. 21-2

```
GTTATGGTAC CGTTTCACCT CTGAAACGAT CCGTCTCAGT ATATATAATT CCTCAAACAA 300
ACCTTGAAAC CCATATCTCT TATTAAATTA CTCCTAAATT GAATTGTCGC GGCTTTTAGC 360
CAACCTTCGA AGATGTCAGC CTCCAGTGTT GTTGTTGCTT AATCGGTCGT TGTCCCCGCC 420
ACCTTTCTTC GCCTAGAACA TAGTACCCAG GAAAAGGTAT TGACAATTTG ACTTTCTATG 480
GAATACTATG TACCATATTT GTTTAATCAA TATTCAAGCT ATCAGTTTTA ATACTTCAAG 540
CGTATGTTTC TCTGGGCAGA ATTCTGAGAT CCACGGTTCT ATCCCAGTTC TTGTGAATCA 600
CTACCATCCA TCGCTACGAT AGGGGGTCGA TTGTGAAAGT TGATTGATCG CTTTGAAGTT 660
GTCCGATTAA CTAATATGAT GTAAACTCTG TTCTGATGAG CTATAACGGA AAGTTATTTG 720
GTTGCTATGA CTAACAGAGG CTGCAAGGCT TGGTACGTCT CAGGCGGAGC TGAAGGACGG 780
TACAACTAGA GCGCCTATTG TCTGGTTTTT GTCGTGCCAA CGTGCTATGA AACTTAAGCC 840
TTCCTTGGAG AATCCAGATC ACTTCGAAAC GTCGGCTGTC ATTTTCAACA GGTACCACCA 900
TGATGTAAAT TTTTTATGT TTGTGGTGTG GTTCGGCTCA AGATTTACG TTTTGCTGAT 960
GAAATAATGA TTTTGTGGAT GCATGACAAT TAGATTTACG AGTCTACAAA CTGTTCATTG 1020
TACATTGGCA GAGAAAAAAT GGCTATGTAT GGTTCAGTTG TAACACCGGT GTGGTGCAAT 1080
GAGGATGGAC ATGGTAACCA AAGGTGTGCA TAATGTTATT GATTCCCTCA GCGATGATTC 1140
CCCTAACATG GATGTGATCG GAATCTCTGG TGAGTTTCTT TTGTATGTTA TTGGTTTGAT 1200
```

FIG. 21-3

```
TTTAAAACAA TGTCTTTTAG CATAGTATCA TCTTGAGACT TAAAAACTTG AAATTTATTG 1260
GTCAGATAAC TTATTCTCCG ACATTAATAA ACCTGCTGCG GTGAACTGCA TCGAGGGACA 1320
TGGCAGTAAT TAGAAGAGAG ATAGGGAATA AGGTGTTGAA AACGAGTGTG TCTGGCTTGG 1380
TGGAGCTCAA TATACTCAAG AACCTCACCG TCTATGTTGT TGCAGGCTCT CTAGGTCGAT 1440
TCAAATCTCA TGCCAGCAAC ATAGTGTTTG ATGTATTCAT AGCTACTTGC CAAGATCCAG 1500
CCCAAAACAT GGAGAGCTCT CAAATTGATG GAAGCCATTA ATAGCAATCA CCGTACCTTC 1560
ACTATCTCCA CCATCACTGA AGATACCATC ATAGAGAACT ATGGAAAAAT CGTCTAATTA 1620
TACTTGGGTA TATATTATAG ATCAGCAAAC CGTATTTATT GTTATCTTGA TAGTTGATAT 1680
AGTATATAAG TAACTAAATT TTCTGAAATT ATTAGAAAAT ACATAAAATAT CTCCCTGCCT 1740
ATTATCACAC AACGTTCTTA CGTGGGGAAT GAAGATATTT AAGGTGTAAA ATTAATTTCA 1800
TTCATATTTC CGGCAATATC CATTGAACC GTCCACCATC TTGCATGCCC ATTACTGCAT 1860
TTTATTATAA TAGAAAAGTA TACCAACTTG AAATATTAAA ACTCCAAGAA TTTGGTTATA 1920
AATAGCTCCT CTCAGCCTCC AACGAAATCA AGCCATATCA ACTATCAGAA CTAGAACAAC 1980
CAAGCCAAAC ATACAAT ATG 2000
                 START
```

PROMOTER

The present invention relates to promoters and to a construct comprising the same. The present invention also relates to a method for the containment of plant germplasm.

In particular, the present invention relates to the use of a promoter for the expression of a gene of interest (GOI) in a specific tissue or tissues of a plant.

More particularly, the present invention relates to promoters for cysteine proteases. The present invention also relates to the application of these cysteine protease promoters to express a GOI in a specific tissue or tissues of a plant.

Promoters control the spatial and temporal expression of genes by modulating their level of transcription. Early approaches to genetically engineered crop plants utilised strong constitutive promoters to drive the expression of foreign genes. As strategies in plant biotechnology have become more sophisticated, there are requirements for specific promoters to target transgene expression to a particular tissue or to a particular developmental stage.

Cysteine proteases are members of a large multigene family in plants (Praekelt et al., 1988; Goetting-Minesky and Mullin, 1994), animals (Wiederanders et al., 1992) and protozoa (Mallinson et al, 1994). Cysteine proteases are synthesised as an inactive precursor (Praekelt et al., 1988). The pre-pro-enzyme is targeted to the secretory pathway (Marttila et al., 1995) and post-transcriptionally processed in the vacuoles by proteolytic cleavage of the propeptide fragment to produce the active enzyme (Hara-Nishimura et al., 1993 and 1994).

Plant cysteine proteases participate in different metabolic events of physiological importance. During seed germination and plant senescence they are involved in protein degradation (Jones et al., 1995; Valpuesta et al., 1995; Smart et al., 1995) and play a key role in protein storage mobilisation during germination (Boylan and Sussex, 1987). During seed development, cysteine proteases catalyse the post-translational processing of protein precursors into their mature form (Hara-Nishimura et al, 1995). In addition, some are subjected to hormonal regulation either by giberellic acid (Koehler and Ho, 1990; Watanabe et al., 1991) or ethylene (Cervantes et al., 1994; Jones et al., 1995). Others are induced in response to stress like wounding (Linthorst et al., 1993; Lidgett et al., 1995), dehydration (Guerrero et al., 1990), cold (Schaffer and Fischer, 1988) or are implicated in plant-microbe interactions (Goetting-Minesky and Mullin, 1994).

Germination specific cysteine proteases have been characterised for barley (Marttila et al., 1995), rice (Watanabe et al., 1991), maize (Debarros and Larkins, 1994), chick-pea (Cervantes et al., 1994), vetch (Becker et al, 1994) and a cysteine protease has been described for oil seed rape (Comai and Harada, 1989). However, the published data for oil seed rape is contradictory. Furthermore, this species is difficult to study due to its amphi-diploid nature. Rather than using more conventional and laborious techniques like subtractive or differential screening of cDNA libraries or differential display techniques, potentially generating clones of unknown identity, cysteine proteinases (cysteine proteases) in oil seed rape were studied which are expressed in germinating seeds. Promoters from genes which are uniquely expressed following seed germination were isolated and characterised.

Thus, according to a first aspect of the present invention, there is provided an oil seed rape cysteine protease gene promoter of class 1, 2 or 6.

According to a second aspect of the present invention, there is provided a promoter comprising at least part of a sequence as shown in FIG. 19 (SEQ ID NO:71), FIG. 20 (SEQ ID NO:72) or FIG. 21 (SEQ ID NO:73), or at least part of a sequence that has substantial homology therewith, or a variant thereof.

According to a third aspect of the present invention, there is provided a promoter having the characteristic motifs or features of promoters of the present invention.

According to a fourth aspect of the present invention, there is provided a recombinant DNA construct comprising the promoter as defined above operably linked to a gene which codes for a protein of interest.

According to a fifth aspect of the present invention, there is provided a recombinant DNA construct functional in a plant comprising a disrupter gene encoding a product capable of disrupting cell function, and a promoter as defined above, the disrupter gene being functionally linked to and controlled by an externally regulatable gene control region which includes a promoter which is inducible by the external application of a chemical inducer.

According to a sixth aspect of the present invention, there is provided DNA comprising at least part of the sequence shown in FIG. 12 (SEQ ID NO:59), FIG. 13, (SEQ ID NO:60), FIG. 14 (SEQ ID NO:62), FIG. 16 (SEQ ID NO:64), or FIG. 17 (SEQ ID NO:65), or at least part of a sequence that has substantial homology therewith or a variant thereof, and which codes for a cysteine protease.

According to a seventh aspect of the present invention, there is provided a recombinant DNA construct functional in a plant comprising the DNA as defined above operably linked to a promoter.

According to an eighth aspect of the present invention, there is provided an expression system for the tissue or tissues of a plant material, the expression system comprising a gene of interest fused to a gene promoter as defined above wherein the expression system is capable of being expressed in the tissue or tissues of the plant material.

According to a ninth aspect of the present invention, there is provided an expression system comprising a construct as defined above.

According to a tenth aspect of the present invention, there is provided a recombinant plant genome comprising a promoter as defined above, DNA as defined above, a recombinant DNA construct as defined above or an expression system as defined above.

According to an eleventh aspect of the present invention, there is provided a plant, plant seed or plant cell having a recombinant plant genome as defined above.

According to a twelfth aspect of the present invention, there is provided protected germplasm comprising a recombinant DNA construct as defined above.

According to a thirteenth aspect of the present invention, there is provided a plant or seed which is capable of growing to maturity comprising a recombinant DNA construct as defined above.

According to a fourteenth aspect of the present invention, there is provided the use of a gene promoter as defined above to induce expression of a gene of interest when fused to the gene promoter in the tissue or tissues of a plant material.

Preferably, the inducible promoter of the recombinant DNA construct is functionally linked to and controls a repressor protein and the disrupter gene promoter includes an operator sequence which is recognised by the repressor protein, so that in the presence of the inducer the repressor protein is produced which interacts with the operator sequence thereby disabling the second promoter and inhibiting expression of the disrupter gene.

Preferably, the disrupter gene is a nucleotide sequence, which is in sense orientation to an endogenous plant gene which is essential to plant development or a gene conferring a desired characteristic on the plant, or comprises a partial sense sequence of the endogenous plant gene.

Preferably, the disrupter gene is a nucleotide sequence which is in antisense orientation to an endogenous plant gene which is essential to plant development or a gene conferring a desired characteristic on the plant.

Preferably, the endogenous plant gene is essential to seed germination or early seedling development.

Preferably, the externally regulatable gene control region is a chemically inducible gene promoter sequence from the glutathione S-transferase system (which is the subject of our International Patent Application No. PCT/GB96/02116), the Alc system (which is the subject of our International Patent Application Nos. PCT/GB96/01883 and PCT/GB96/01846) or the ecdysone system (which is the subject of our International Patent Application No. PCT/GB96/01195).

Preferably, the repressor protein gene encodes a bacterial repressor such as the lac repressor or a repressor used by 434, P22 or lambda-bacteriophages.

Preferably, the disrupter gene or disrupter promoter contains a "pseudo-operator".

Preferably, the disrupter gene is a cytotoxic gene.

Preferably, the disrupter gene encodes a recombinase or a transposase adapted to excise a nucleotide sequence flanked by recombinase recognition sequences.

Preferably, the recombinant DNA construct is capable of being expressed in the tissue or tissues of a germinating seedling or a developing grain or a plant when the construct is integrated, preferably stably integrated, within the grain's or seedling's or plant's genomic DNA.

Preferably, the expression system is for at least the tissue of a germinating seedling or developing grain or plant (eg in the root, cotyledons, leaves and stem).

Preferably, the expression system is integrated, preferably stably integrated, within a germinating seedling's genomic DNA or a developing grain's genomic DNA or a plant's genomic DNA.

Preferably, the gene promoter is used to induce expression of a gene of interest when fused to the gene promoter in at least the tissue or tissues of a germinating seedling or a developing grain or a plant (eg in the root, cotyledons, leaves and stem).

According to a preferred embodiment of the present invention, the promoter comprises a DNA sequence corresponding to that of the promoter region of the clone pKS12p6 (SEQ ID NO: 71), as shown in FIG. 19.

According to another preferred embodiment of the present invention, the promoter comprises a DNA sequence corresponding to that of the promoter region of the clone pKS25p7 (SEQ ID NO: 72), as shown in FIG. 20.

According to a further preferred embodiment of the present invention, the promoter comprises a DNA sequence corresponding to that of the promoter region of the clone pKS66p1 (SEQ ID NO: 73), as shown in FIG. 21.

An even more preferred embodiment of the present invention is a seedling, grain or plant comprising a construct comprising a disrupter gene fused to a cysteine protease promoter, wherein the construct is integrated, preferably stably integrated within the seedling's, grain's or plant's genomic DNA, wherein the promoter comprises at least part of a sequence shown in FIGS. 19, 20 or 21, or at least part of a sequence that has substantial homology therewith, or a variant thereof and wherein the disrupter gene is a gene which encodes barnase ribonuclease.

An even more preferred embodiment of the present invention is a seedling, grain or plant comprising a construct comprising a disrupter gene fused to a cysteine protease promoter, wherein the construct is integrated, preferably stably integrated within the seedling's, grain's or plant's genomic DNA, wherein the promoter comprises at least part of a sequence shown in FIGS. 19, 20 or 21, or at least part of a sequence that has substantial homology therewith, or a variant thereof and wherein the disrupter gene is a gene which encodes a recombinase adapted to excise a nucleotide sequence flanked by recombinase recognition sequences.

Thus, according to a highly preferred embodiment of the present invention, there is provided a recombinant DNA construct for insertion into the genome of a plant to impart control of plant development thereto, comprises, in sequence:

(a) an inducible gene promoter sequence responsive to the presence or absence of an exogenous chemical inducer;

(b) either a gene encoding a repressor protein under control of the said inducible gene promoter sequence or a gene encoding an inhibitor of the product of the disrupter gene specified at (e) below;

(c) an operator sequence responsive to the said repressor protein;

(d) a gene promoter sequence of the present invention; and, (e) a gene encoding a protein disrupter of a plant characteristic essential to the growth of the plant, whereby the presence or absence of the exogenous chemical inducer enables either growth to maturity or causes growth to slow down or stop at an appropriate stage.

The inducible promoter used in the present invention may promote expression of the repressor protein in response to stimulation by an exogenous chemical inducer whereby in the absence of the chemical inducer no repressor protein is expressed to interact with the operator thus permitting expression of the disrupter protein gene and in the presence of the chemical inducer repressor protein is expressed thereby preventing expression of the gene encoding the inhibitor of plant development permitting unimpeded plant growth.

The term "plant material" includes a developing caryopsis, a germinating caryopsis or grain, or a seedling, a plantlet or a plant, or tissues or cells thereof, such as the cells of a developing caryopsis or the tissues of a germinating seedling or developing grain or plant (e.g. in the root, leaves and stem).

The term "gene of interest" or "GOI" with reference to the present invention means any gene of interest. A GOI can be any gene that is either foreign or natural to the plant in question, except for the wild type functional gene when in its natural environment.

Typical examples of a GOI includes genes encoding for proteins and enzymes that disrupt cell function. For example, the gene may be a cytotoxic gene. Alternatively the gene may encode a recombinase, transposase, or a related enzyme with similar properties, adapted to inhibit an endogenous plant gene which is essential to plant development or a gene conferring a desired characteristic on the plant.

A recombinase is an enzyme that recognises a specific excision sequence or set of specific excision sequences and effects the removal of, or otherwise alters, DNA between specific excision sequences. Recombinase systems such as the Cre-lox, the FLP, SRI and SSV1-encoded integrase systems may be used in the present invention.

Other examples of a GOI include defensive or protective genes, such as genes giving herbicide, fungal or insect resistance. Such genes may be expressed during germination of seedlings at which time the seedlings are particularly vulnerable. Preferably, the gene encodes a protein which confers resistance to biotic and environmental stresses on a plant.

Also included are endogenous genes such as genes encoding β-tubulin and adenine nucleotide translocator (ANT).

The term "disrupter gene" is a gene which, when expressed or repressed specifically at a suitable stage of plant development, will lead to the failure of a plant to reach maturity and to set seed. The origin of the disrupter genes can be from a variety of naturally occurring sources e.g. human cells, bacterial cells, yeast cells, plant cells, fungal cells, or they can be totally synthetic genes which may be composed of DNA sequences, some of which may be found in nature, some of which are not normally found in nature or a mixture of both. The disrupter genes will preferably be targeted to an essential biochemical function, such as DNA and RNA metabolism, protein synthesis, and other metabolic pathways.

In a preferred embodiment, the disrupter gene is a gene which encodes barnase ribonuclease, β-tubulin or adenine nucleotide translocator (ANT).

The term "variant thereof" with reference to the present invention means any substitution of, variation of, modification of, replacement of, deletion of or the addition of one or more nucleic acid(s) from or to the promoter sequence providing the resultant sequence is capable of expressing a GOI. The term also includes sequences that can substantially hybridise to the promoter sequence. The term also includes DNA which hybridises to the DNA of the present invention and which codes for at least part of a cysteine protease promoter. Preferably, such hybridisation occurs at, or between, low and high stringency conditions. In general terms, low stringency conditions can be defined as 3×SSC at about ambient temperature to about 65° C., and high stringency conditions as 0.1×SSC at about 65° C. SSC is the name of a buffer of 0.15M NaCl, 0.015M trisodium citrate. 3×SSC is three time as strong as SSC and so on.

The term "substantial homology" covers homology with respect to at least the essential nucleic acids/nucleic acid residues of the promoter sequence providing the homologous sequence acts as a promoter e.g. a cysteine protease promoter which is capable of expressing a GOI. Typically, homology is shown when 60% or more of the nucleotides are common with the promoter sequence of the present invention, more typically 65%, preferably 70%, more preferably 75%, even more preferably 80% or 85% and, especially preferred, are 90%, 95%, 98% or 99% or more homology.

The term "construct"—which is synonymous with terms such as "cassette". "hybrid" and "conjugate"—includes a GOI directly or indirectly attached to the promoter of the present invention, such as to form a cassette. An example of an indirect attachment is the provision of a suitable spacer group such as an intron sequence, intermediate the promoter and the GOI. The same is true for the term "fused" in relation to the present invention which includes direct or indirect attachment.

The term "expression system" means that the system defined above can be expressed in an appropriate organism, tissue, cell or medium. In this regard, the expression system of the present invention may comprise additional components that ensure to increase the expression of the GOI by use of the gene promoter.

The DNA of the present invention may be genomic DNA which is in an isolated form and is, preferably, operably linked to a sequence with which it is not naturally associated, or the DNA may be synthetic DNA or cDNA.

Young seedlings at germination represent a vulnerable stage of plant development. Strategies to improve crop production may include expression of genes during this stage to enhance the seedling's resistance to biotic and environmental stresses such as resistance to cold, salt, heavy metals, fungal attack. Protecting seedlings by expressing proteins which provide at least some measure of resistance/tolerance against such stresses, for example anti-fungal proteins (Cammue et al., 1992; Terras et al., 1993) under the control of a germination specific promoter will limit the expression to a precise phase of development, when the proteins will be most effective. Such development specific expression has further advantages such as avoiding expression of these genes in plant material entering the food chain.

The promoters of the present invention may also be advantageously used in plant germplasm containment systems.

Agriculture uses many crop plants for the production of food for human consumption, for commercial processes yielding products for human consumption, for animal feedstuff production, for the development of industrial products and other purposes. The process involves the planting by the farner of seed which usually has been purchased from a seed producer. The product produced by the crop, be it the whole plant, the seed or fruit of the plant, is harvested and is then used for the various food applications mentioned above.

The supplied hybrid or inbred seed may incorporate novel genetic information introduced by transformation of the crop giving novel agronomic features such as tolerance to herbicides, insect pests, and fungal diseases, improved yield and/or quality of the harvested product, and novel mechanisms for the control of plant fertility. Such improvements which are made possible through biotechnological research, improve the quality of the plant breeding and improve the agronomic performance of the seed supplied to the farmer.

A problem addressed by the present invention is the containment of crop plants within the area of cultivation. Seeds of cultivated crop plants may be conveyed outside the defined growing area by a number of routes (by birds or small mammals or simply by being dropped during post-harvest transport of a seed crop) where they assume the status of weeds, or they may remain as volunteers in a subsequent crop in later years. It would clearly be appropriate, if it were possible, that cultivated crops be confined to the growing area and prevented from persisting in the wild. It will be appreciated that the problems of crop non-confinement mentioned above become more acute where transgenic crops are involved.

In the same way, pollen can travel long distances through wind and/or insect transportation (dispersion) and remain viable for a long period. Since interspecific crossing between crop plants and their non cultivated related species is possible, a second concern is the escape of pollen from transgenic crops e.g. herbicide resistant crops, to their related weeds species (Mikkelsen et al., 1996). Ways to reduce viability of such hybrids would limit the risk of transgene escape to non-crop species thus avoiding the spreading of plants with enhanced invasiveness or weediness.

It will be appreciated that the use of the seedling promoters of the present invention restricts expression of the disrupter protein gene to a suitable stage of plant development, and also means that it is not necessary to continue to apply an inducer chemical to the plant throughout its lifetime in order to maintain its viability. This has both economic and ecological benefits.

The invention also provides a genetically transformed plant and parts thereof, such as cells protoplasts and seeds, having incorporated, preferably stably incorporated, into the genome the construct of the present invention.

Thus, the invention provides a plant which can be reversibly inhibited at an appropriate developmental stage in which said plant contains, preferably stably incorporated in its genome, the recombinant DNA construct defined above.

Expression of a protein encoded by a gene is controlled by the interaction of certain regulatory proteins, known as DNA-binding proteins, with a region located upstream of the gene. Within the promoter region, there are located several operator regions which contain a specific oligonucleotide sequence to which these DNA-binding proteins specifically bind. These proteins can lead either to activation or repression of gene expression. Thus, they control the regulated expression of genes.

These DNA-binding proteins, which may in fact be either repressors or activators of gene expression, are herein referred to for the sake of simplicity as "repressors".

The present invention makes use of the well-characterised interaction between bacterial operators with their repressors to control the expression of the disrupter gene function. Bacterial repressors, particularly the lac repressor, or repressors used by 434, P22 and lambda bacteriophages can be used to control the expression in plant cells very effectively.

A second operator/repressor system is the subject of our published International Patent Application No. WO90/08827 which is incorporated herein by reference.

A third approach for the down-regulation of the disrupter genes which can be considered is the use of either "antisense", "sense" or "partial sense" technology.

A DNA construct according to the invention may be an "antisense" construct generating "antisense" RNA or a "partial-sense" construct (encoding at least part of the functional gene product) generating "sense" RNA.

"Antisense RNA" is an RNA sequence which is complementary to a sequence of bases in the corresponding mRNA: complementary in the sense that each base (or the majority of bases) in the antisense sequence (read in the 3' to 5' sense) is capable of pairing with the corresponding base (G with C, A with U) in the niRNA sequence read in the 5' to 3' sense. Such antisense RNA may be produced in the cell by transformation with an appropriate DNA construct arranged to generate a transcript with at least part of its sequence complementary to at least part of the coding strand of the relevant gene (or of a DNA sequence showing substantial homology therewith).

"Sense RNA" is an RNA sequence which is substantially homologous to at least part of the corresponding mRNA sequence. Such sense RNA, or partial sense RNA, may be produced in the cell by transformation with an appropriate DNA construct arranged in the normal orientation so as to generate a transcript with a sequence identical to at least part of the coding strand of the relevant gene (or of a DNA sequence showing substantial homology therewith). Suitable sense, or partial sense constructs may be used to inhibit gene expression (as described in International Patent Publication WO91/08299).

Antisense RNA constructs which may be used to down-regulate disrupter genes include those encoding adenine nucleotide translocator.

Other approaches which are, or become, available may also be used.

Further details on such crop containment systems can be found in our published International Patent Application No. WO94/03619 which is incorporated herein by reference.

The promoter of the present invention, then, when linked to an exogenous or foreign gene and introduced into a plant by transformation, provides a means for the regulation of expression of that foreign gene. The method employed for transformation of the plant cells is not especially germane to this invention and any method suitable for the target plant may be employed. Transgenic plants are obtained by regeneration from the transformed cells. Numerous transformation procedures are known from the literature such as agroinfection using *Agrobacterium tumefaciens* or its Ti plasmid, electroporation, microinjection or plants cells and protoplasts, microprojectile transformation, to mention but a few. Reference may be made to the literature for fuill details of the known methods.

Neither is the plant species into which the promoter sequence is inserted particularly germane to the invention. Dicotyledonous and monocotyledonous plants can be transformed. This invention may be applied to any plant for which transformation techniques are, or become, available. The present invention can therefore be used to control gene expression in a variety of genetically modified plants, including field crops such as canola, sunflower, tobacco, sugarbeet, and cotton; cereals such as wheat, barley, rice, maize, and sorghum; fruit such as tomatoes, mangoes, peaches, apples, pears, strawberries, bananas and melons; and vegetables such as carrot, lettuce, cabbage and onion. The promoter is also suitable for use in a variety of tissues, including roots, leaves, stems and reproductive tissues.

Thus, nucleic acid sequences which code for novel cysteine proteases have been isolated and characterised. The DNA comprising at least part of the sequence shown in any one of FIGS. 12 to 17 codes for a cysteine protease and corresponds to the coding region of the sequence. The present invention also includes DNA which shows homology to the sequences of the present invention. The present invention also includes DNA which hybridises to the DNA of the present invention and which codes for at least part of a cysteine protease. Such homology and hybridisation is discussed above in relation to the promoter sequences.

The present invention further includes DNA which is degenerate as a result of the genetic code to the DNA of the present invention and which codes for a cysteine protease.

Also provided by the present invention is a cysteine protease, which is substantially free from other proteins with which it is ordinarily associated, and which is coded for by cysteine protease gene DNA of the present invention.

The present invention will now be described by way of non-limiting example only, and with references to the accompanying drawings, in which:

Figure 3A-2:
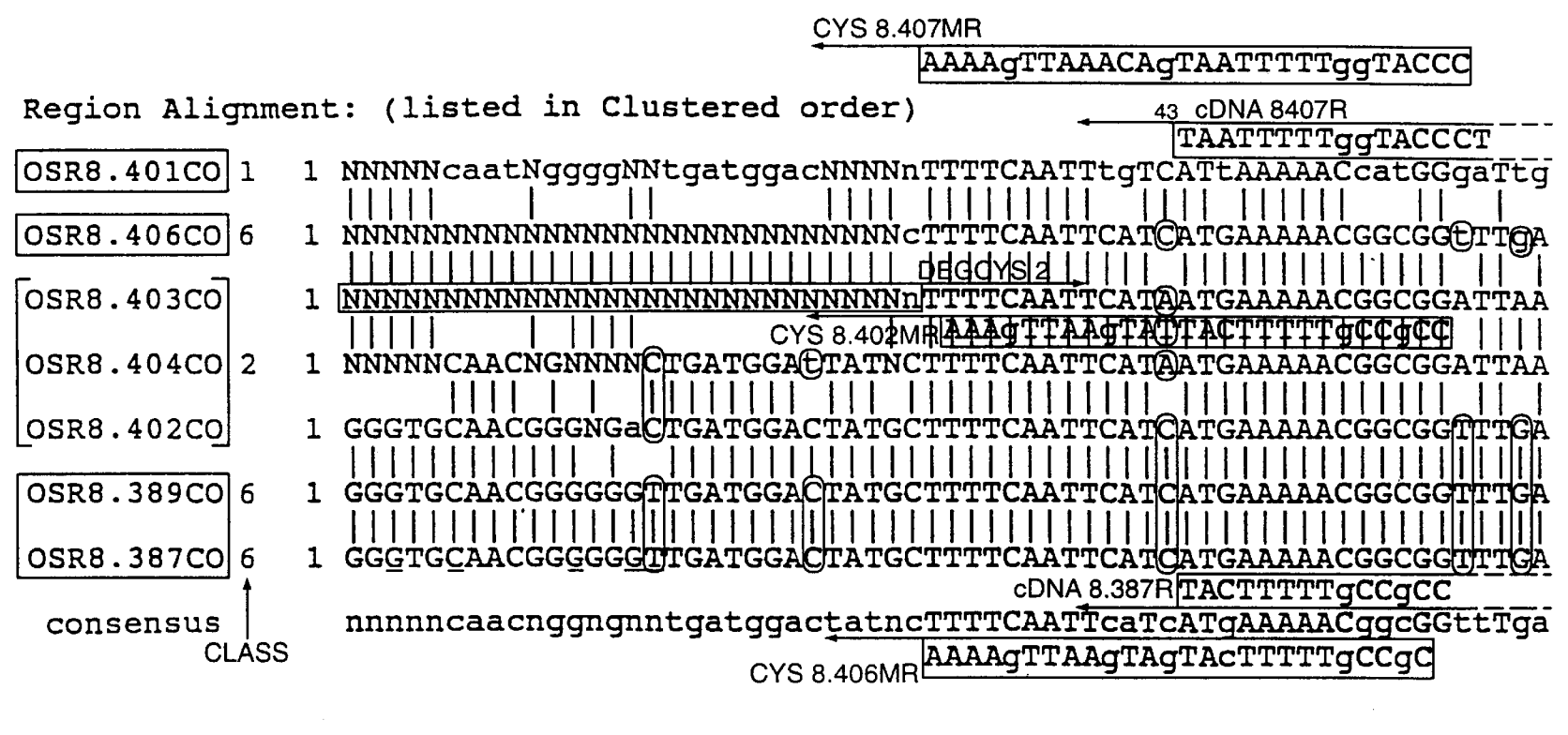
Figure 3A-3:
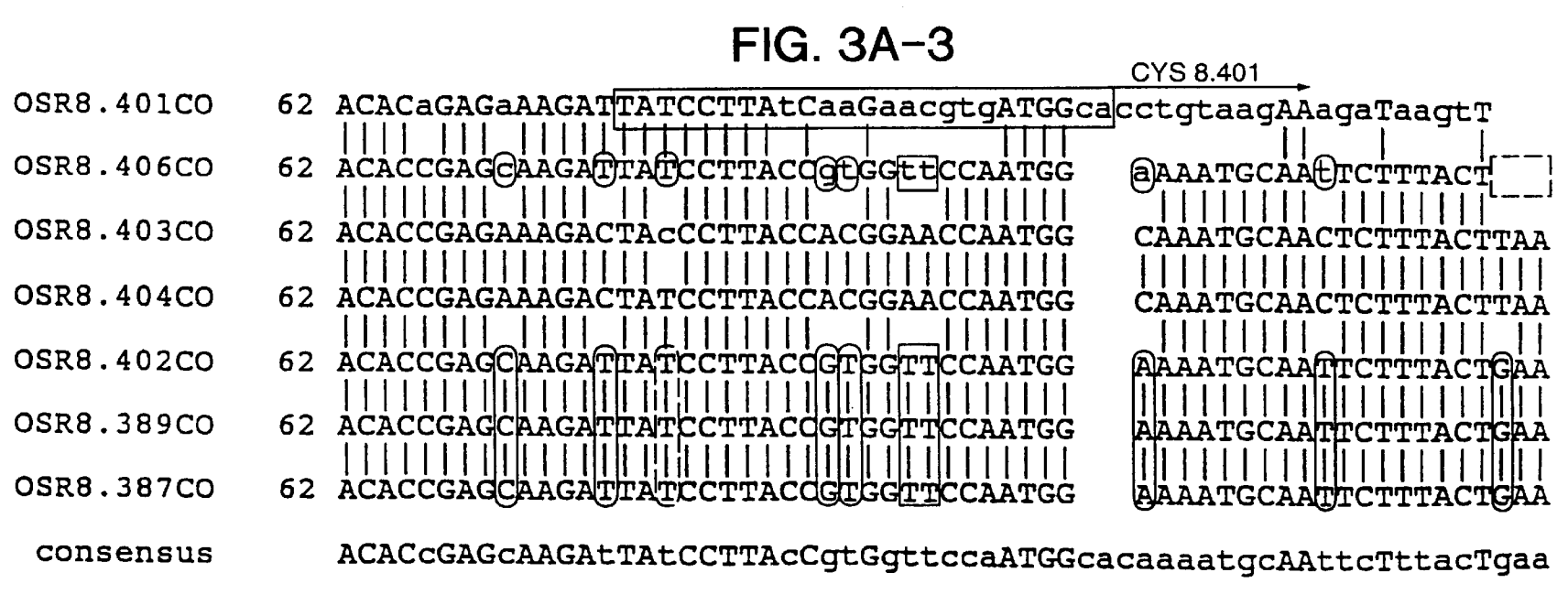
Figure 3A-6:
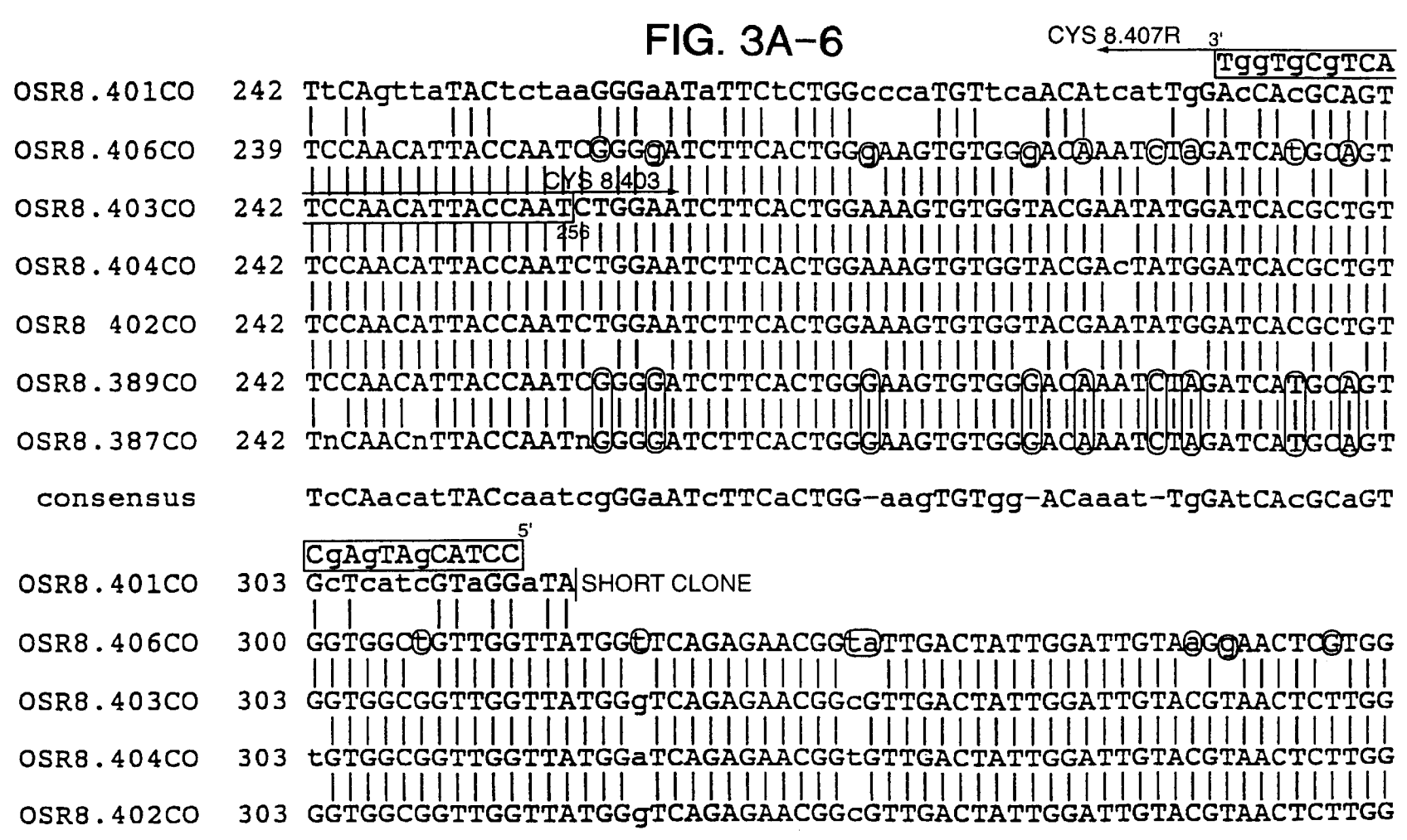
Figure 3A-7:
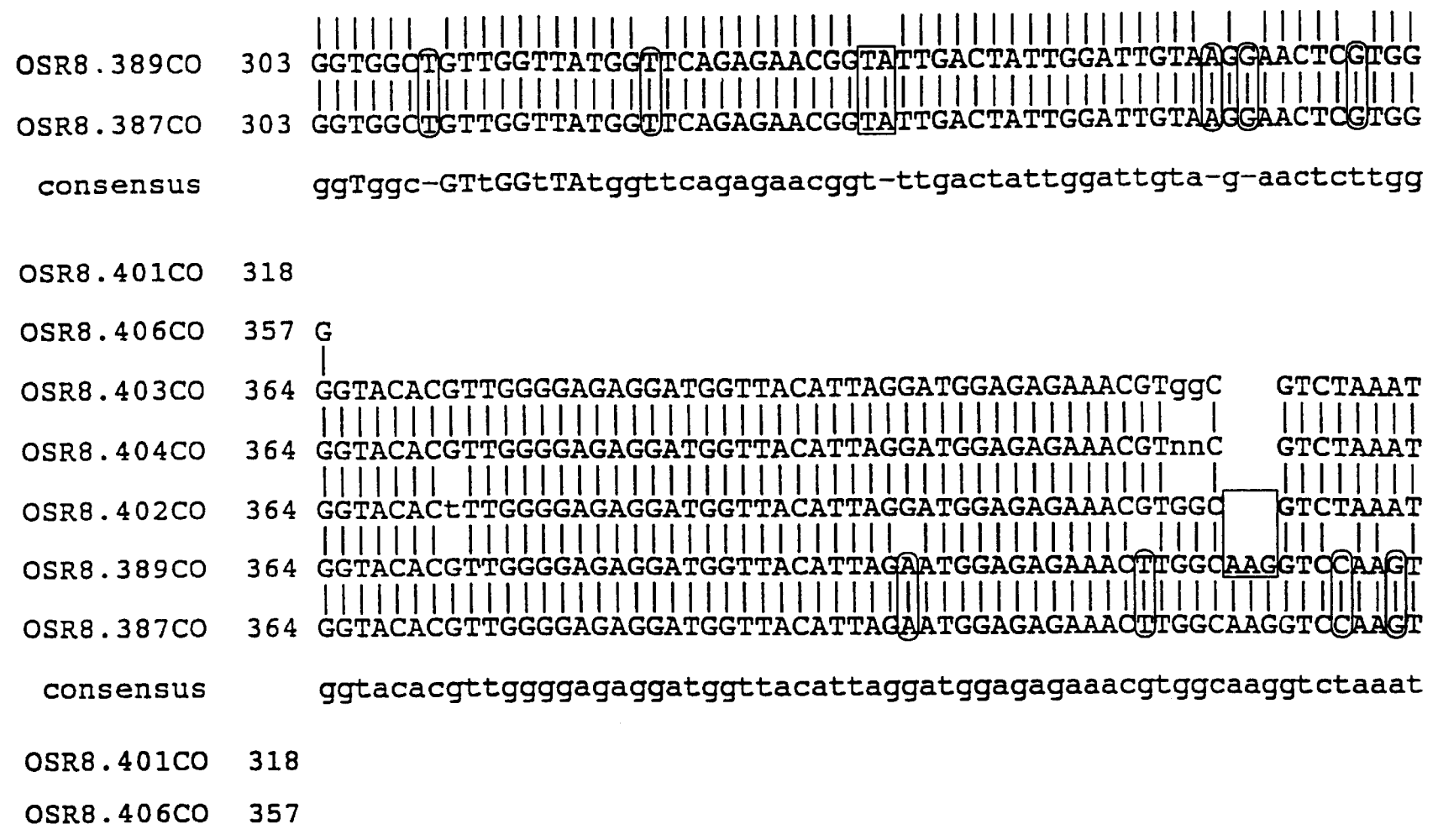

FIGS. 3A-1–3A-8 show the alignment of the coding regions of the preliminary nucleic acid sequences of RT-PCR clones OSR8.401 (SEQ ID NO: 39), OSR8.406 (SEQ ID NO: 35), OSR8.403 (SEQ ID NO: 36), OSR8.404 (SEQ ID NO: 37), OSR8.402 (SEQ ID NO: 38), OSR.839 (SEQ ID NO: 39) and OSR8.387 (SEQ ID NO: 40). The consensus sequence is SEQ ID NO: 75.

FIGS. 3B-1, 3B-2 and 3B-3 show the alignment of the non-coding regions of the preliminary nucleic acid sequences of RT-PCR clones OSR8.389 (SEQ ID NO: 39), OSR8.387 (SEQ ID NO: 40), OSR8.402 (SEQ ID NO: 38) and OSR8.404 (SEQ ID NO: 37). The consensus sequence is SEQ ID NO: 76.

FIGS. 4-1–4-4 show the preliminary nucleic acid sequence of clones OSR8.401 (SEQ ID NO: 34), OSR8.402 (SEQ ID NO: 38) and OSR8.389 (SEQ ID NO: 39);

FIG. 5 shows the results of a northern blot of the class 2 clone, OSR8.402 (SEQ ID NO: 38), comparing expression in the seed and during germination, using a random primed whole RT-PCR fragment as probe. In this Figure, L=leaf, C=cotyledons, S=seeds and B=buds;

Figure 1:
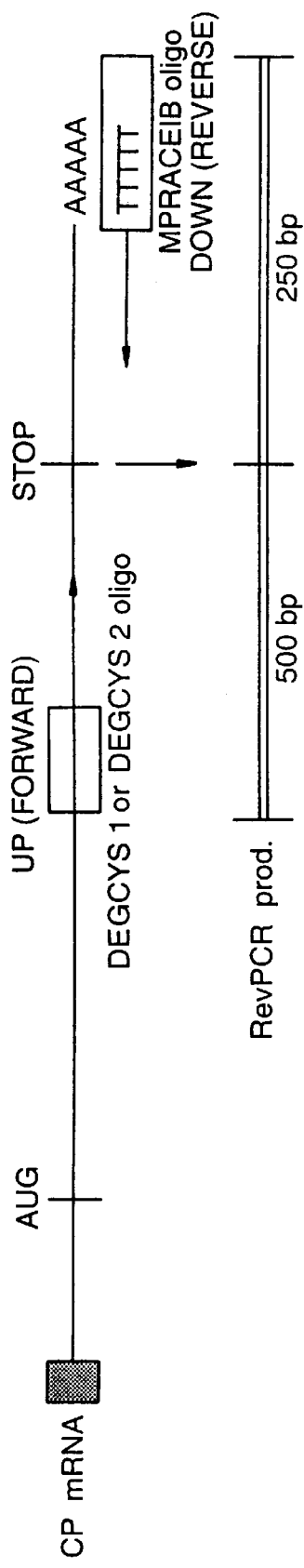
FIG. 1 shows a schematic outline of the identification of cysteine protease isoforms using a reverse transcribed PCR library.
Figure 1:
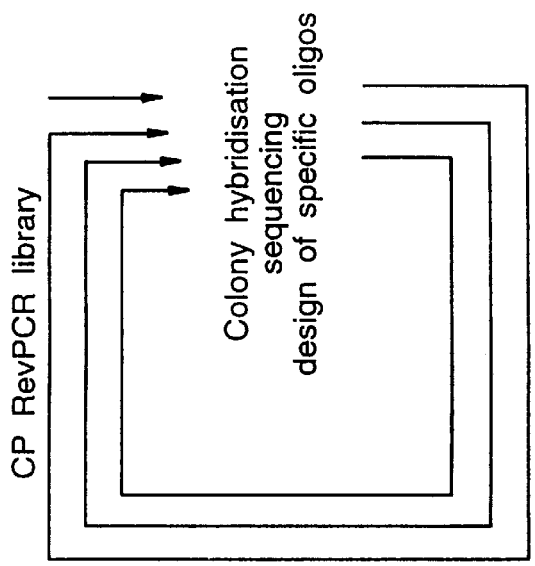
Figure 6:
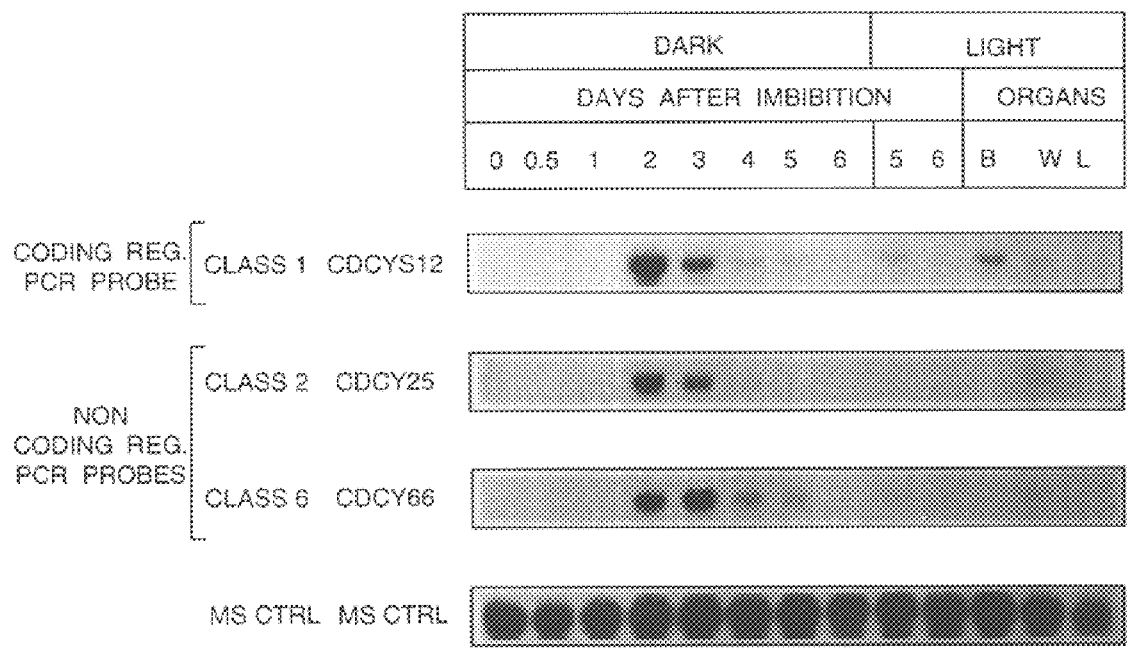
Figures 1, 11:
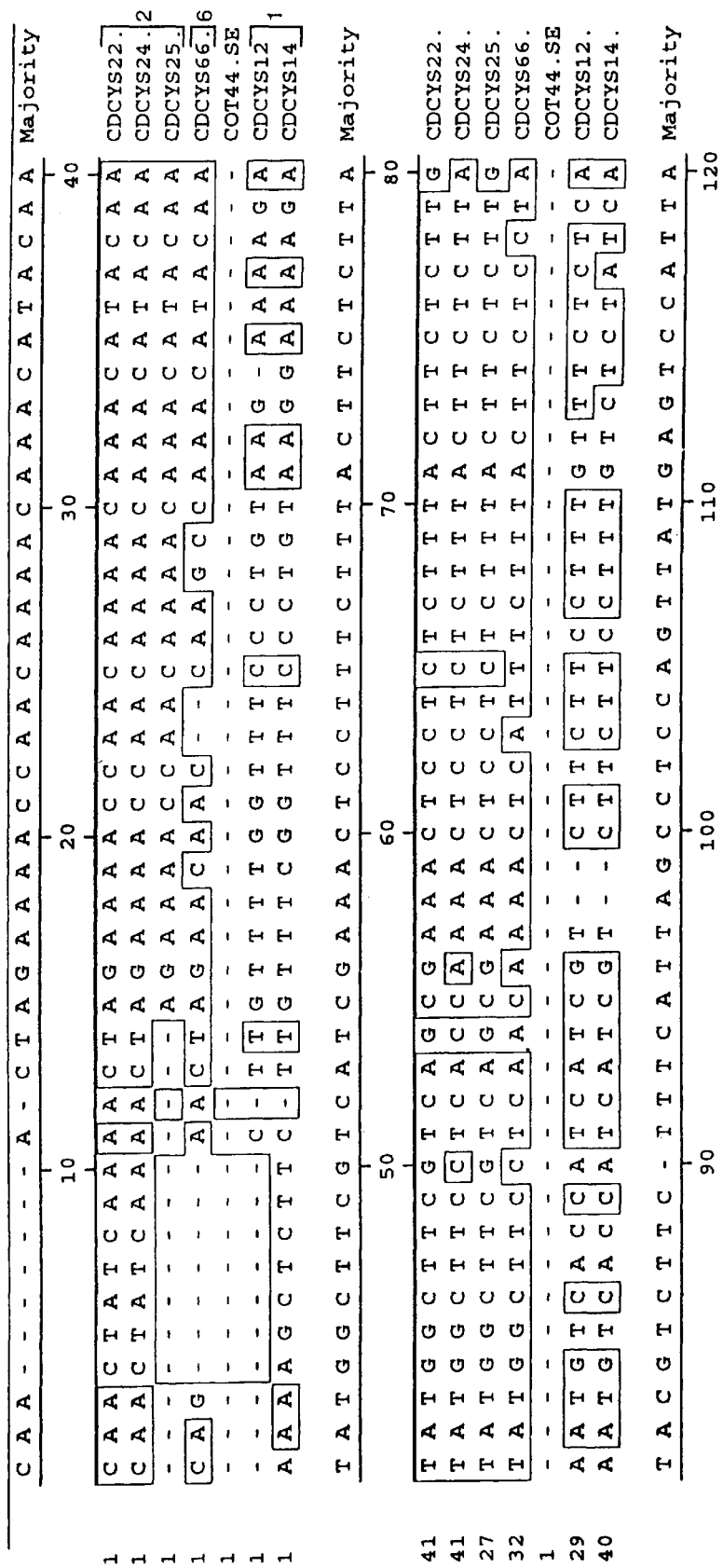
Figures 5, 11:
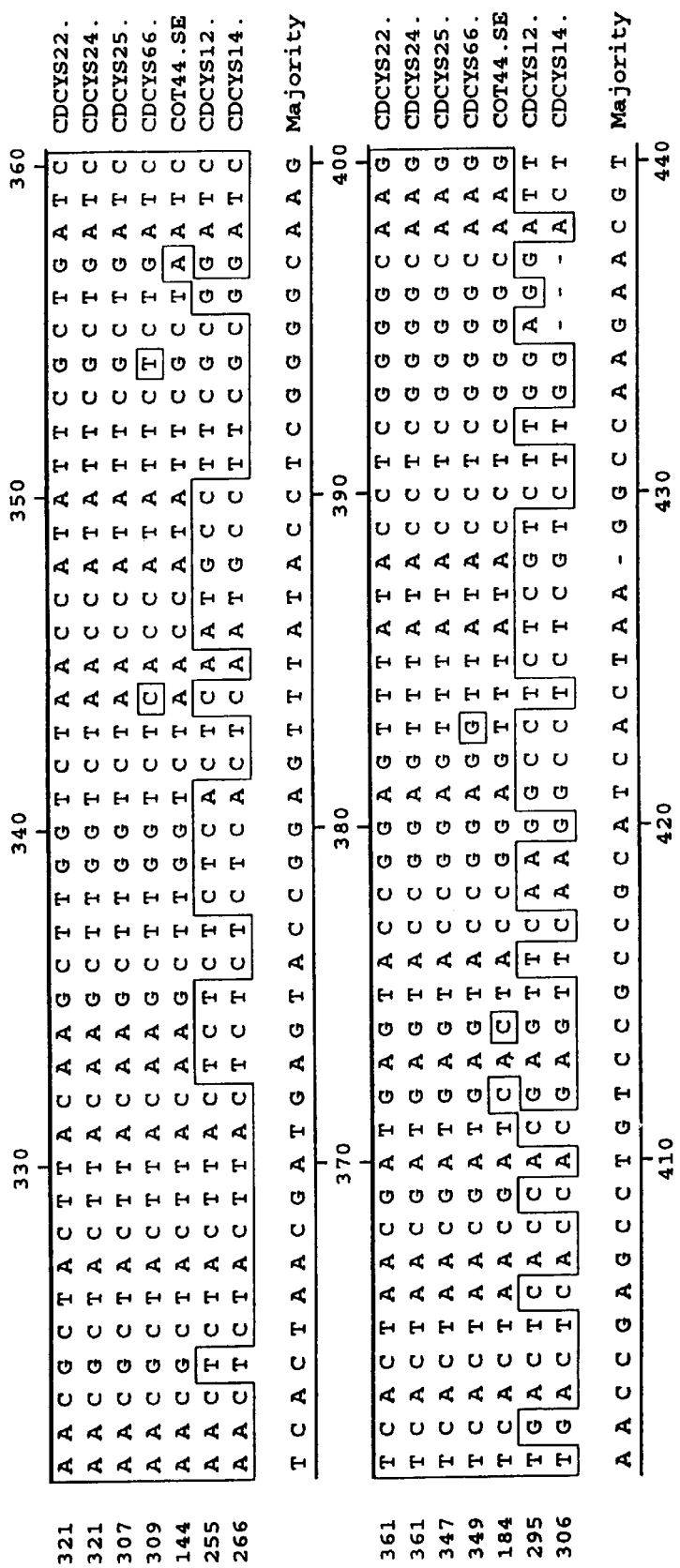
Figures 6, 11:
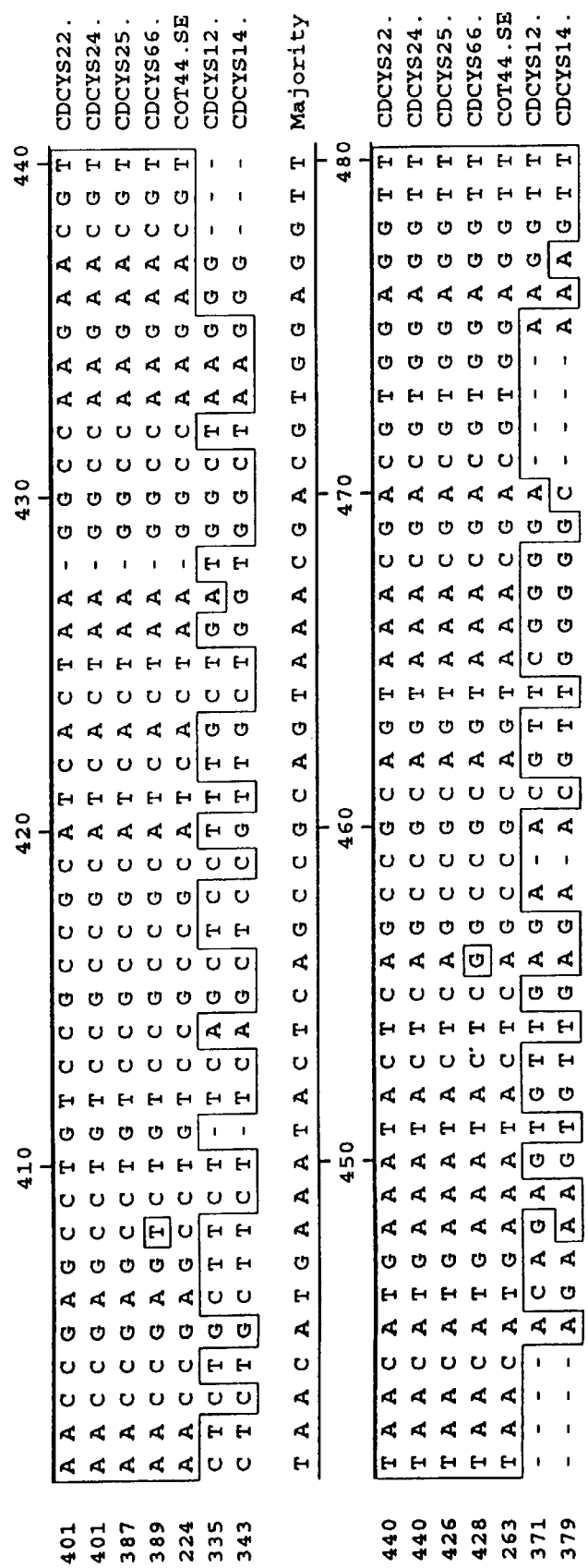
Figures 7, 11:
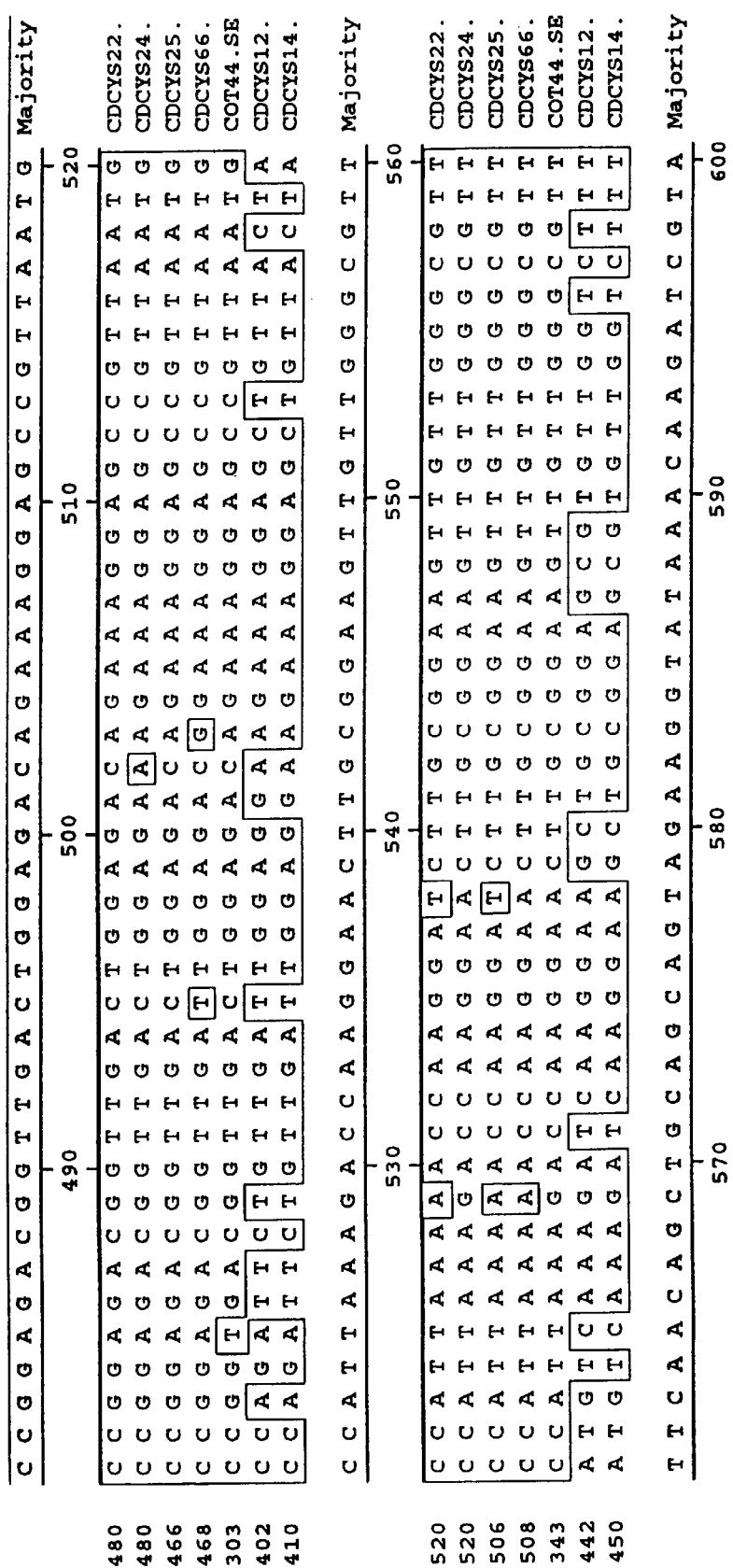

FIG. 6 shows the results of northern blots of the class 1 clone, CDCYS12 (SEQ ID NO: 59) (using the coding region of the clone as a probe, labelled by PCR), the class 2 clone, CDCYS25 (SEQ ID NO: 63) (using the noncoding region of the clone as a probe, labelled by PCR) and the class 6 clone, CDCYS66 (SEQ ID NO: 64) (using the non-coding region of the clone as a probe, labelled by PCR) comparing expression in a range of developmental stages. In this Figure, B=bud, W=whole plant and L =leaf;

FIGS. 7-1–7-4 show the alignment of the deduced amino acid sequences of clones OSR8.403 (SEQ ID NO: 36), OSR8.404 (SEQ ID NO: 37), OSR.402 (SEQ ID NO: 38), OSR.389 (SEQ ID NO: 39), OSR8.387 (SEQ ID NO: 40), OSR8.406 (SEQ ID NO: 35) and OSR8.401 (SEQ ID NO: 34) with the published sequence of COT44 (designated CYS4.BRANA) (SEQ ID NO: 77). The consensus sequence is SEQ ID NO: 78.

Figure 2:
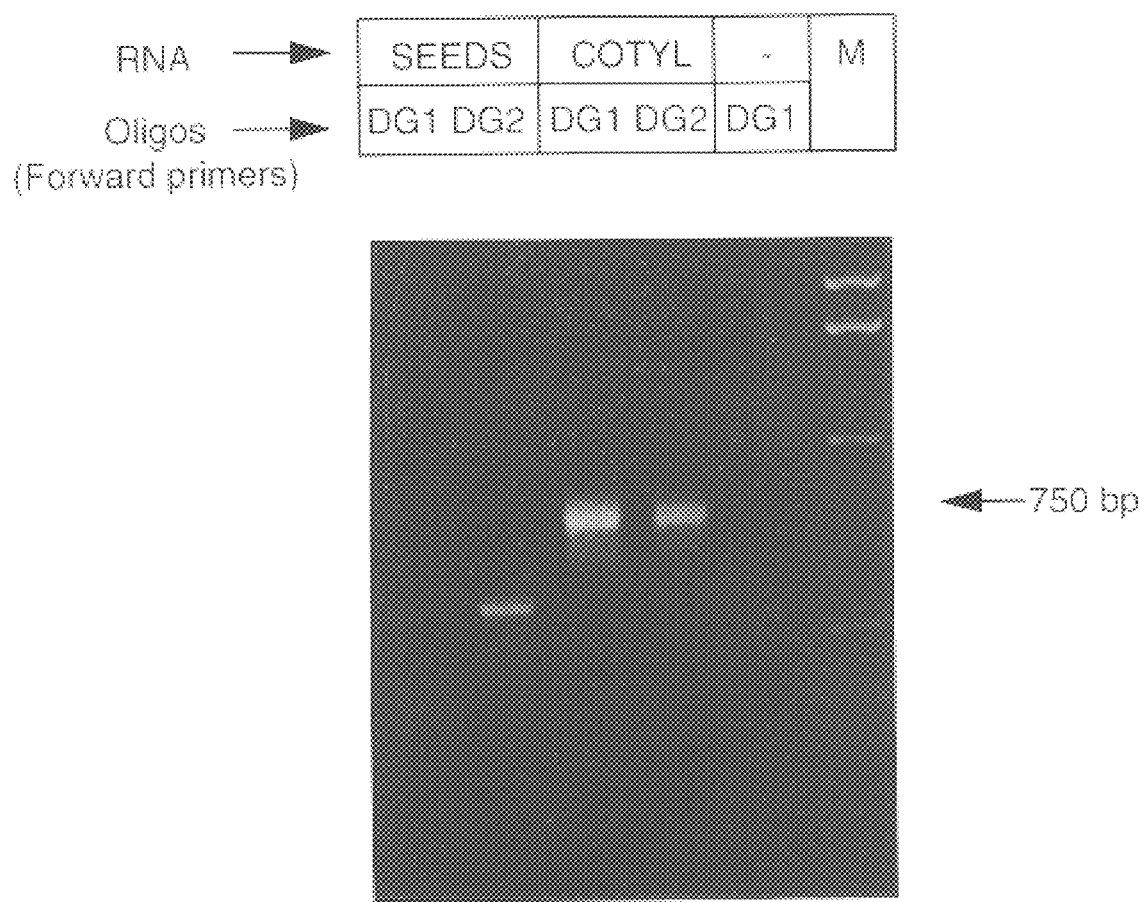
FIG. 2 shows the analysis of RT-PCR products by agrose gel electrophoresis and in which DG1=DEGCYS1 (SEQ ID NO: 2) and DG2=DEGCYS2 (SEQ ID NO: 3) oligos.
Figure 8:
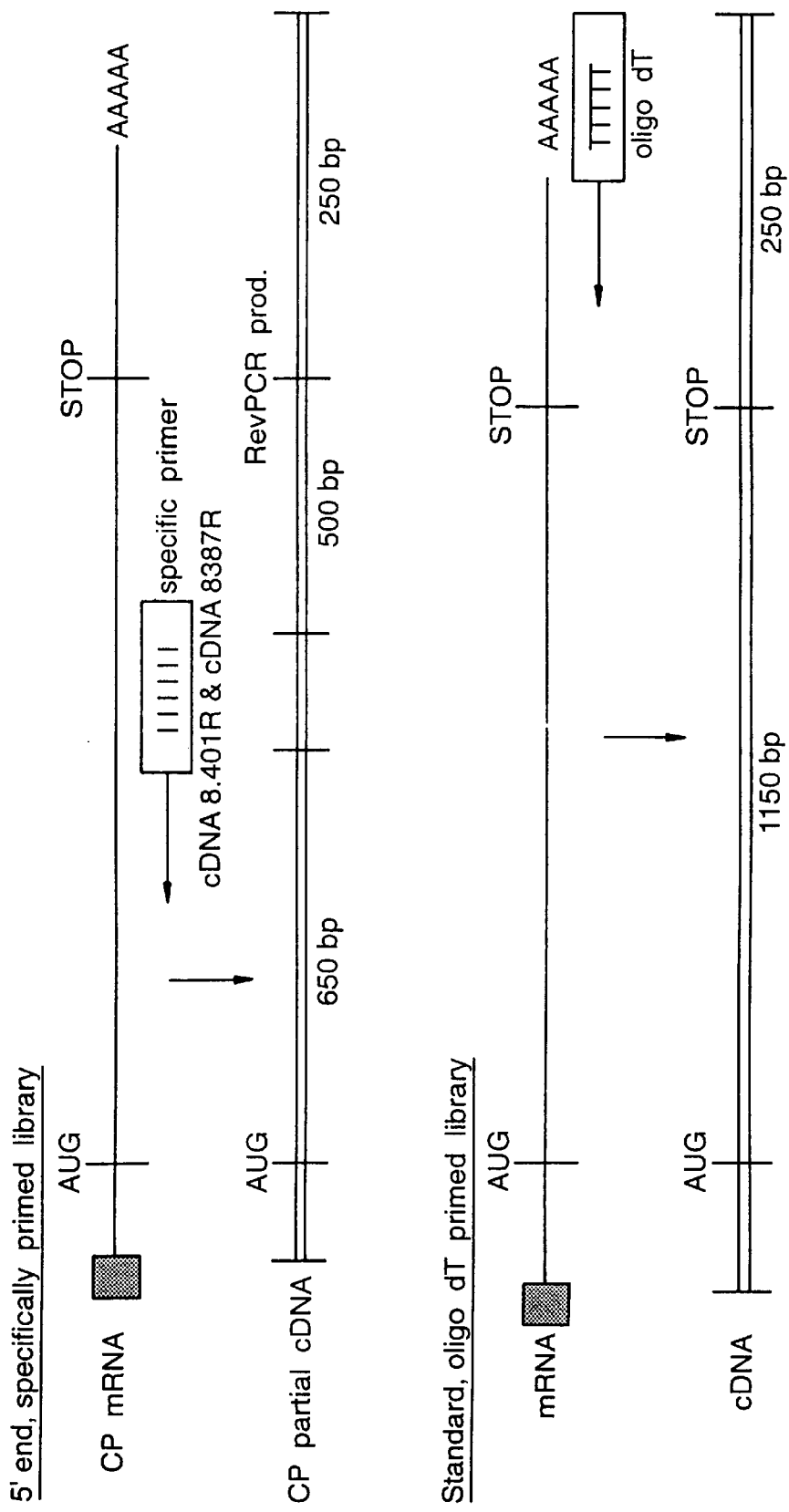
Figure 9:
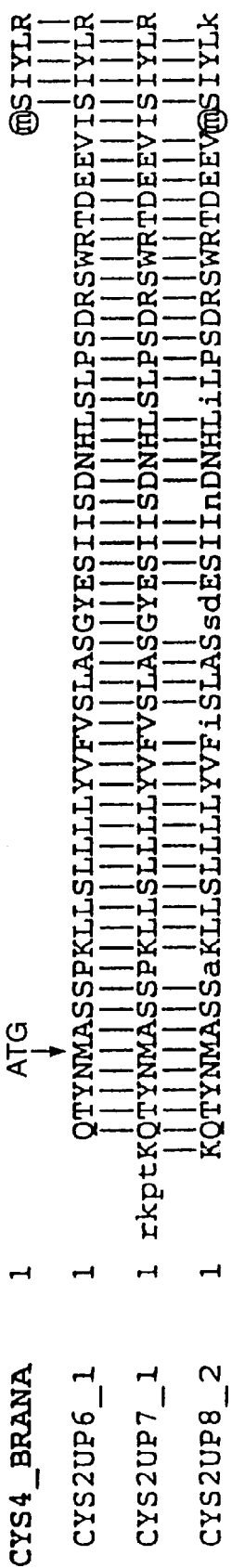

FIG. 8 shows a schematic outline of the identification of cysteine protease isoforms using a cDNA library;

FIGS. 9-1 and 9-2 show the alignment of the deduced amino acid sequences of the partial length cDNA class 2 clones, CYS2UP6.1 (SEQ ID NO: 49), CYS2UP7.1 (SEQ ID NO: 50) and CYS2UP8.2 (SEQ ID NO: 51), with each other and with COT44 (designated CYS4.BRANA) (SEQ ID NO: 79). The consensus sequence is SEQ ID NO: 80.

FIGS. 10-1–10-6 show the alignment of the nucleic acid sequences of the partial cDNA clones, CYS2UP6 (SEQ ID NO: 52), CYS2UP7 (SEQ ID NO: 53), CYS2UP8 (SEQ ID NO: 54), CYS6UP3 (SEQ ID NO: 55), CYS6UP5 (SEQ ID NO: 56), CYS6UP2 (SEQ ID NO: 57) and CYS6UP4 (SEQ ID NO: 58), with each other and with COT44 (SEQ ID NO: 85). The consensus sequence is SEQ ID NO: 81.

FIGS. 11-1–11-21 show the alignment of the full length cDNA clones, CDCYS66 (SEQ ID NO: 64), CDCYS24 (SEQ ID NO: 62), CDCYS22 (SEQ ID NO: 61), CDCYS25 (SEQ ID NO: 63), CDCYS12 (SEQ ID NO: 59) and CDCYS14 (SEQ ID NO: 60), with each other and with COT44 (SEQ ID NO: 36). The majority sequence is SEQ ID NO: 82.

Figures 11, 12, 13:
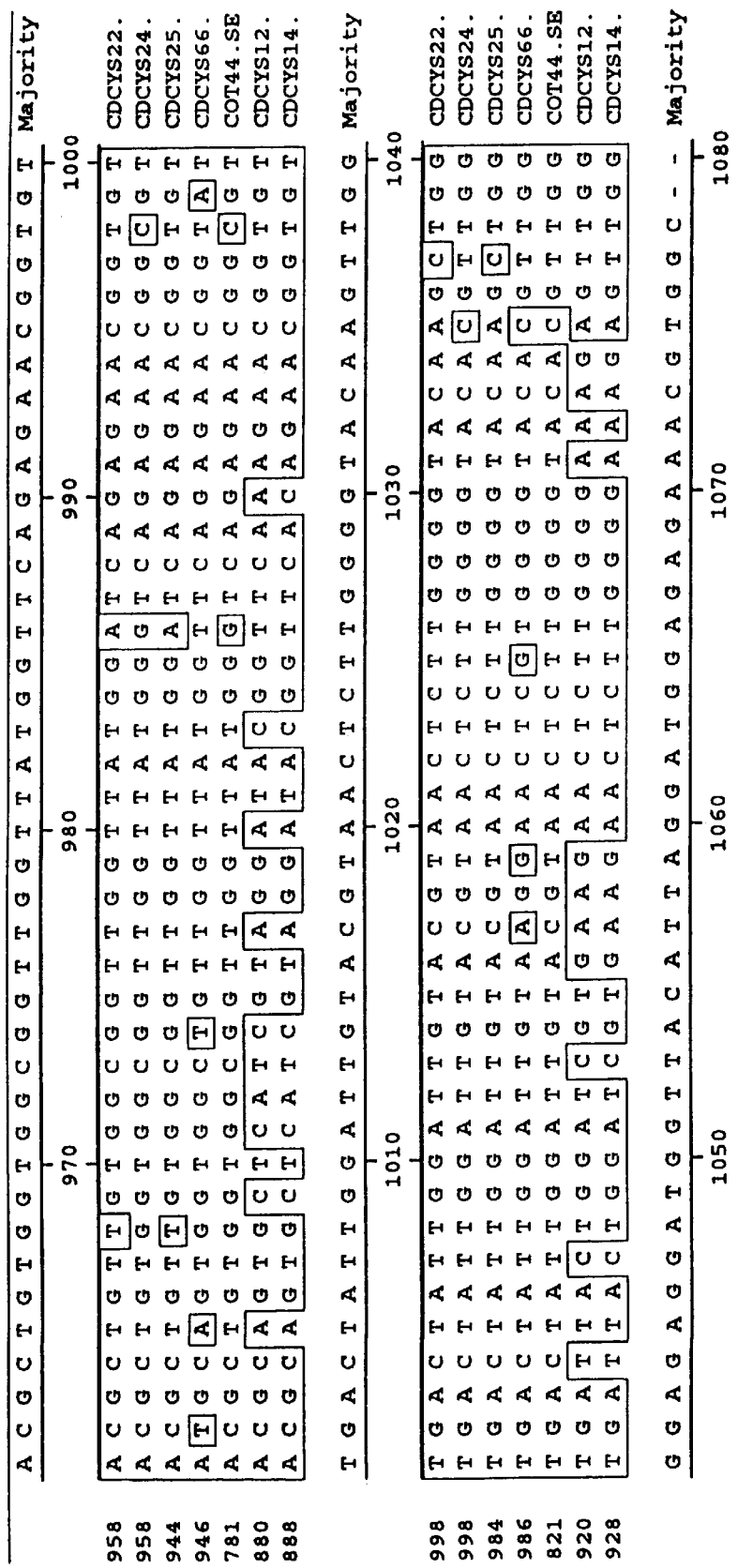
Figures 11, 12, 13, 14, 15, 16, 17:
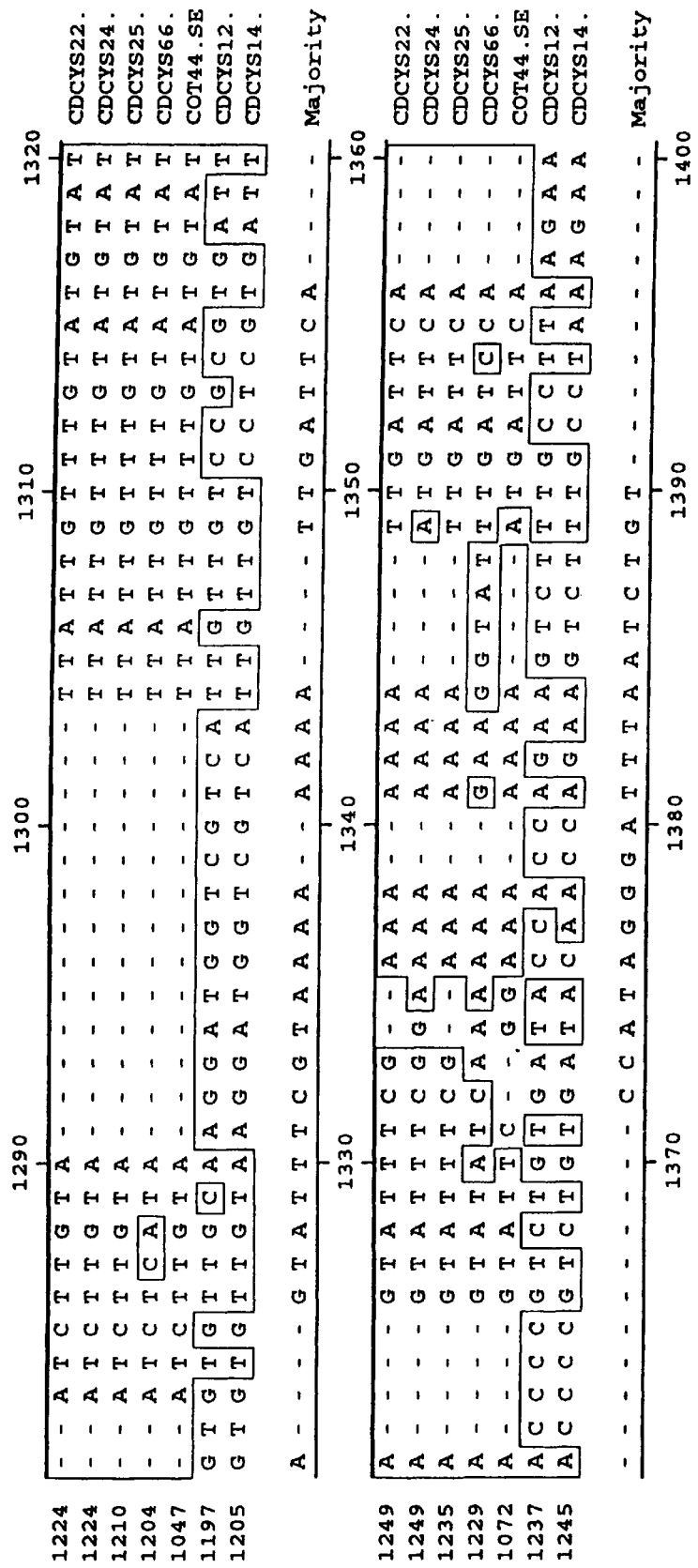
Figures 11, 12, 13, 14, 15, 16, 17, 18:
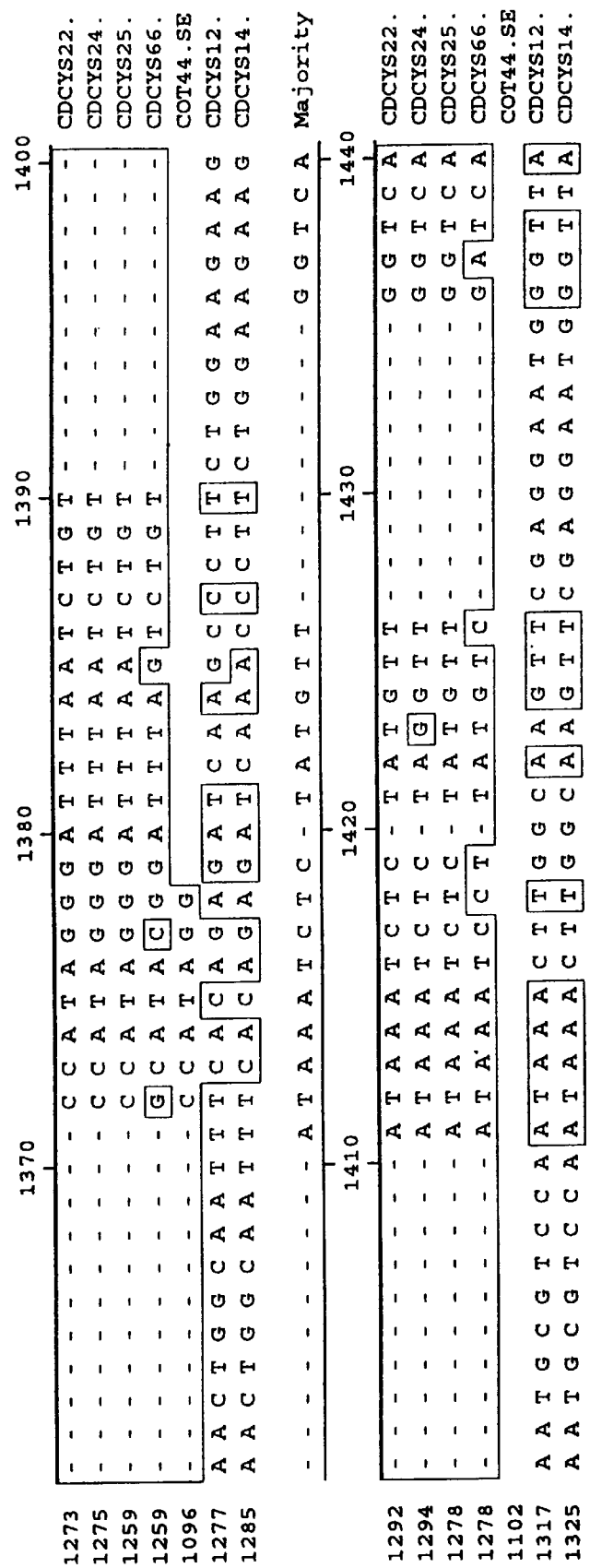

FIGS. 12-1 and 12-2 show the nucleic acid sequence of cDNA clone CDCYS12 (SEQ ID NO: 59);

FIGS. 13-1 and 13-2 show the nucleic acid sequence of cDNA clone CDCYS14 (SEQ ID NO: 60);

FIGS. 14-1 and 14-2 show the nucleic acid sequence of cDNA clone CDCYS22 (SEQ ID NO: 61);

FIGS. 15-1 and 15-2 show the nucleic acid sequence of cDNA clone CDCYS24 (SEQ ID NO: 62);

FIGS. 16-1 and 16-2 show the nucleic acid sequence of cDNA clone CDCYS25 (SEQ ID NO: 63);

FIGS. 17-1 and 17-2 show the nucleic acid sequence of cDNA clone CDCYS66 (SEQ ID NO: 64);

FIGS. 18-1–18-6 show the alignment of the predicted amino acid sequences of cDNA clones CDCYS12 (SEQ ID NO: 59), CDCYS14 (SEQ ID NO: 60), CDCYS22 (SEQ ID NO: 61), CDCYS24 (SEQ ID NO: 62), CDCYS25 (SEQ ID NO: 63) and CDCYS66 (SEQ ID NO: 64), and compares the sequences with the characterising features of plant cysteine proteases. The majority sequence is SEQ ID NO: 83. COT44.PRO is SEQ ID NO: 84. The motif $E_{x3}R_{x3}F_{x2}N_{x3}I_{x3}N$ is SEQ ID NO: 89.

Figures 11, 12, 13, 14, 15, 16, 17, 18, 19, 20:
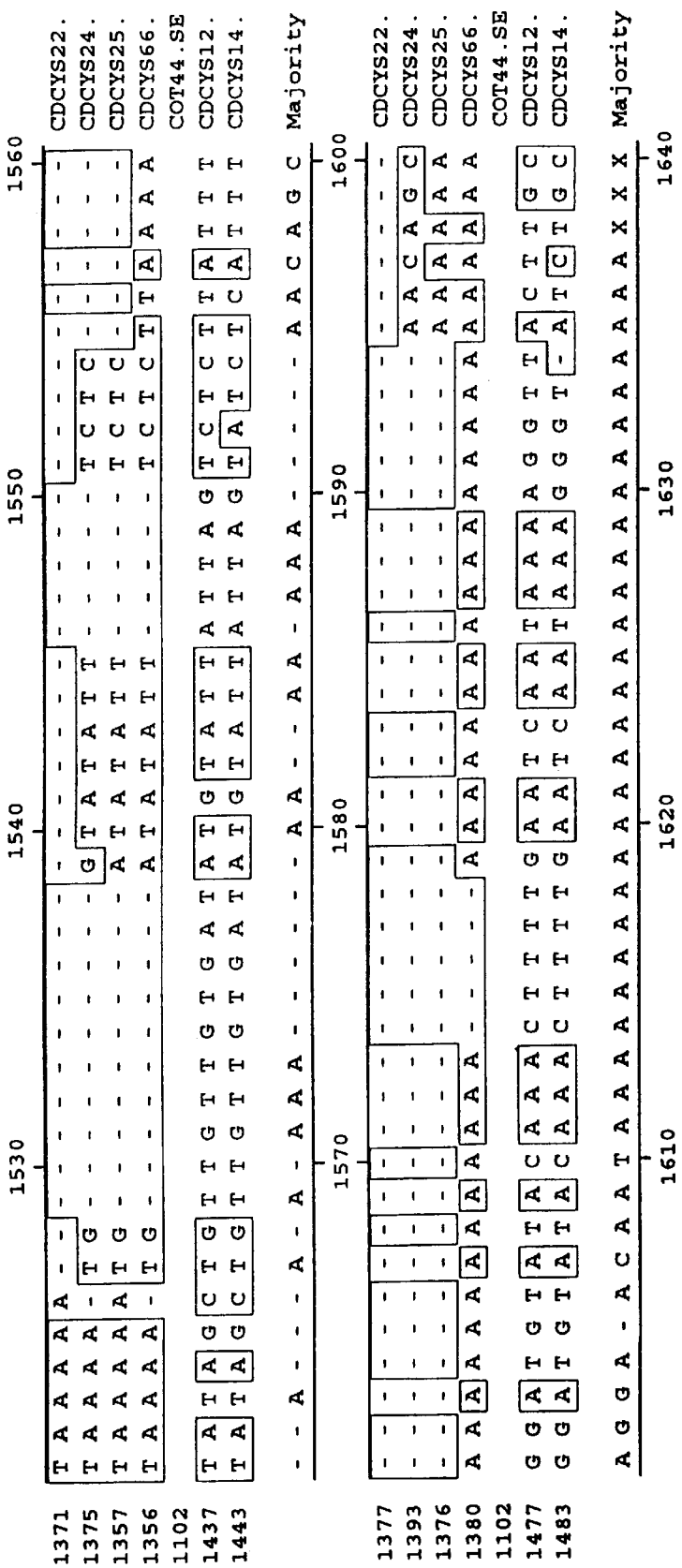
Figures 11, 12, 13, 14, 15, 16, 17, 18, 19, 20, 21:
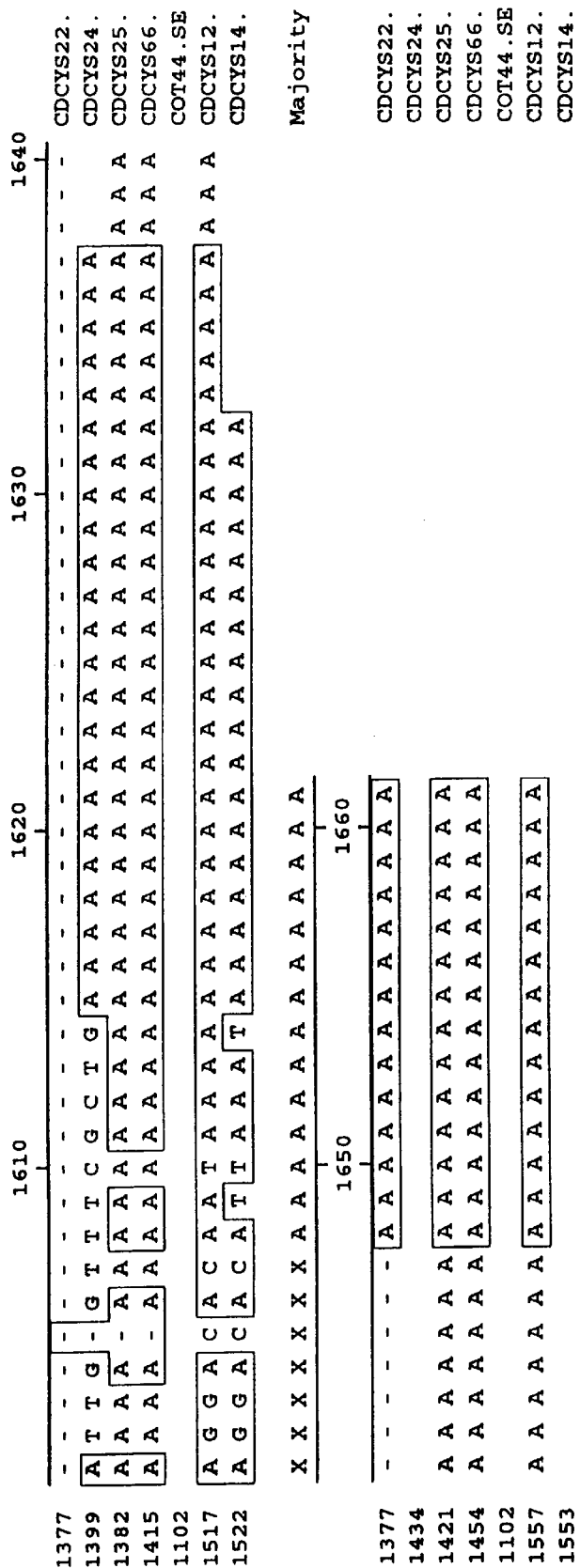
Figures 1, 18:
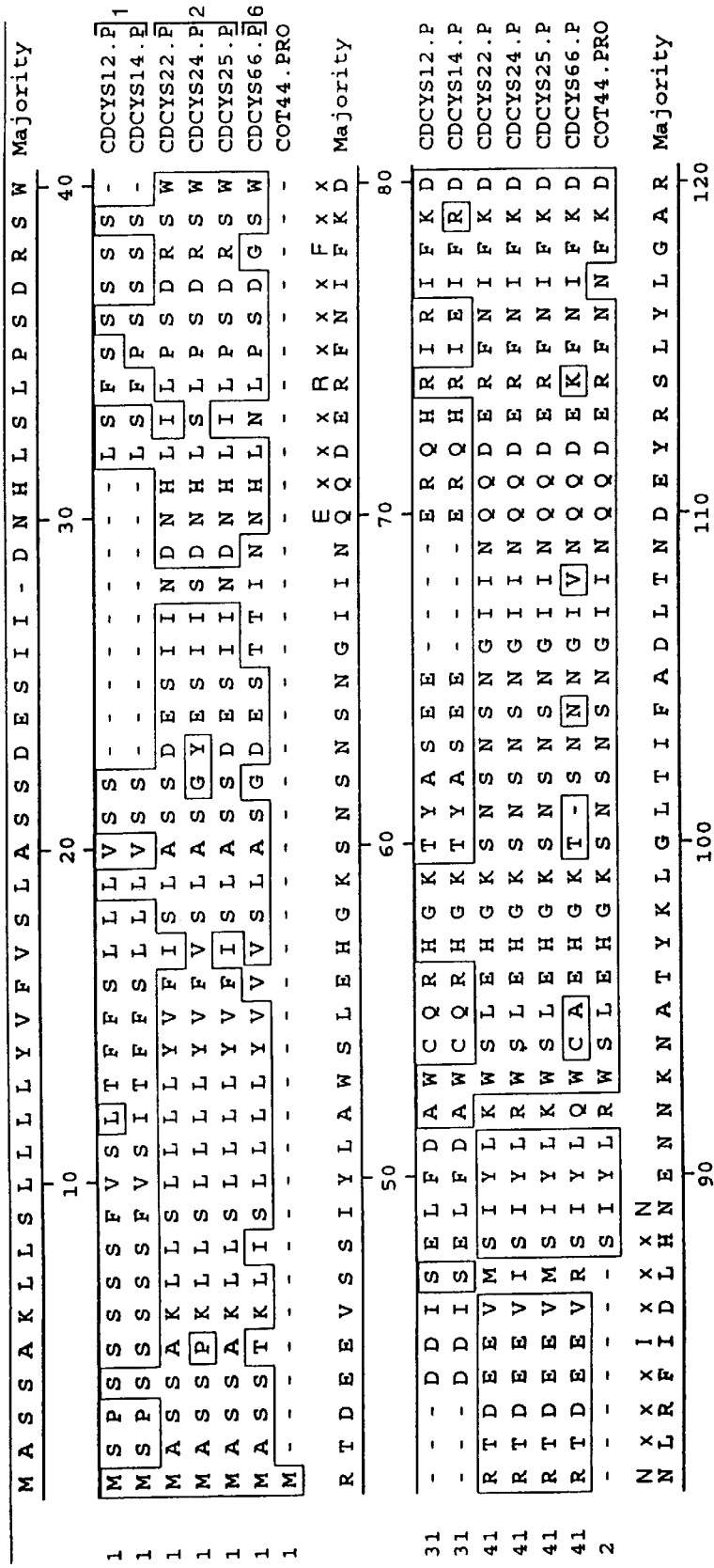
Figures 3, 18:
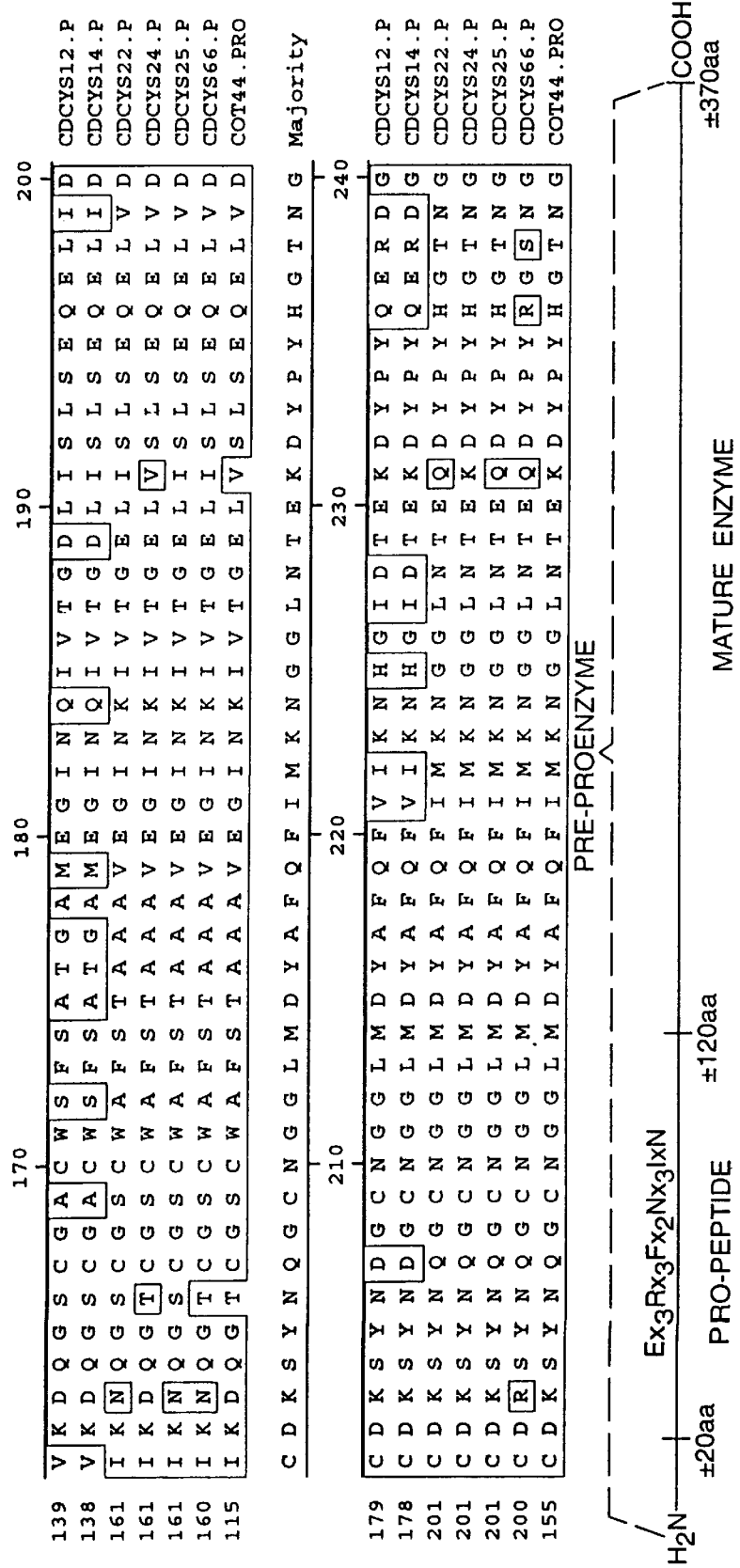

FIGS. 19-1 and 19-2 show a promoter nucleic acid sequence from class 1 genomic clone pKS12p6 (SEQ ID NO: 71).

FIGS. 20A-1–20A-3 and 20B-1–20B-2 show a promoter nucleic acid sequence from class 2 genomic clone pKS25p7 (SEQ ID NO: 72).

FIGS. 21-1, 21-2 and 21-3 show a promoter nucleic acid sequence from class 6 genomic clone PKS66P1 (SEQ ID NO: 73).

Figure 22:
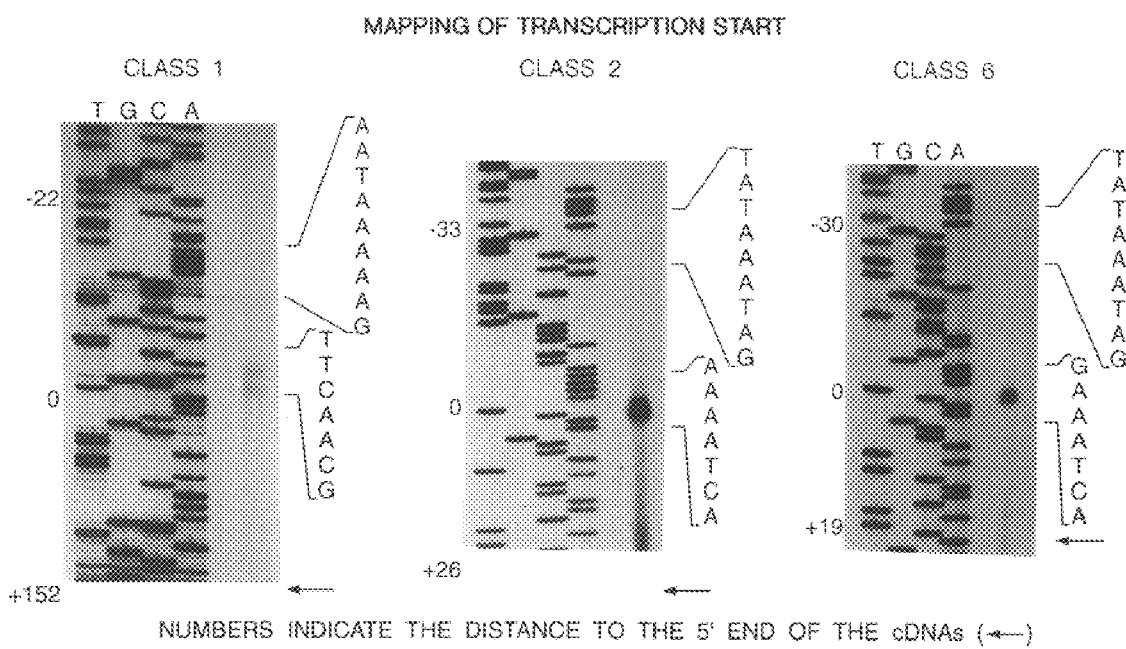

FIG. 22 shows the mapping of the transcription start by primer extension experiments as well as the position of the putative TATA box of clones pKS12P6 (SEQ ID NO: 71) (class 1), pKS25P7 (SEQ ID NO: 72) (class 2) and pKS66P1 (SEQ ID NO: 73) (class 6). Numbers indicate the distance to the 5'end of the cDNAs.

Figure 23:
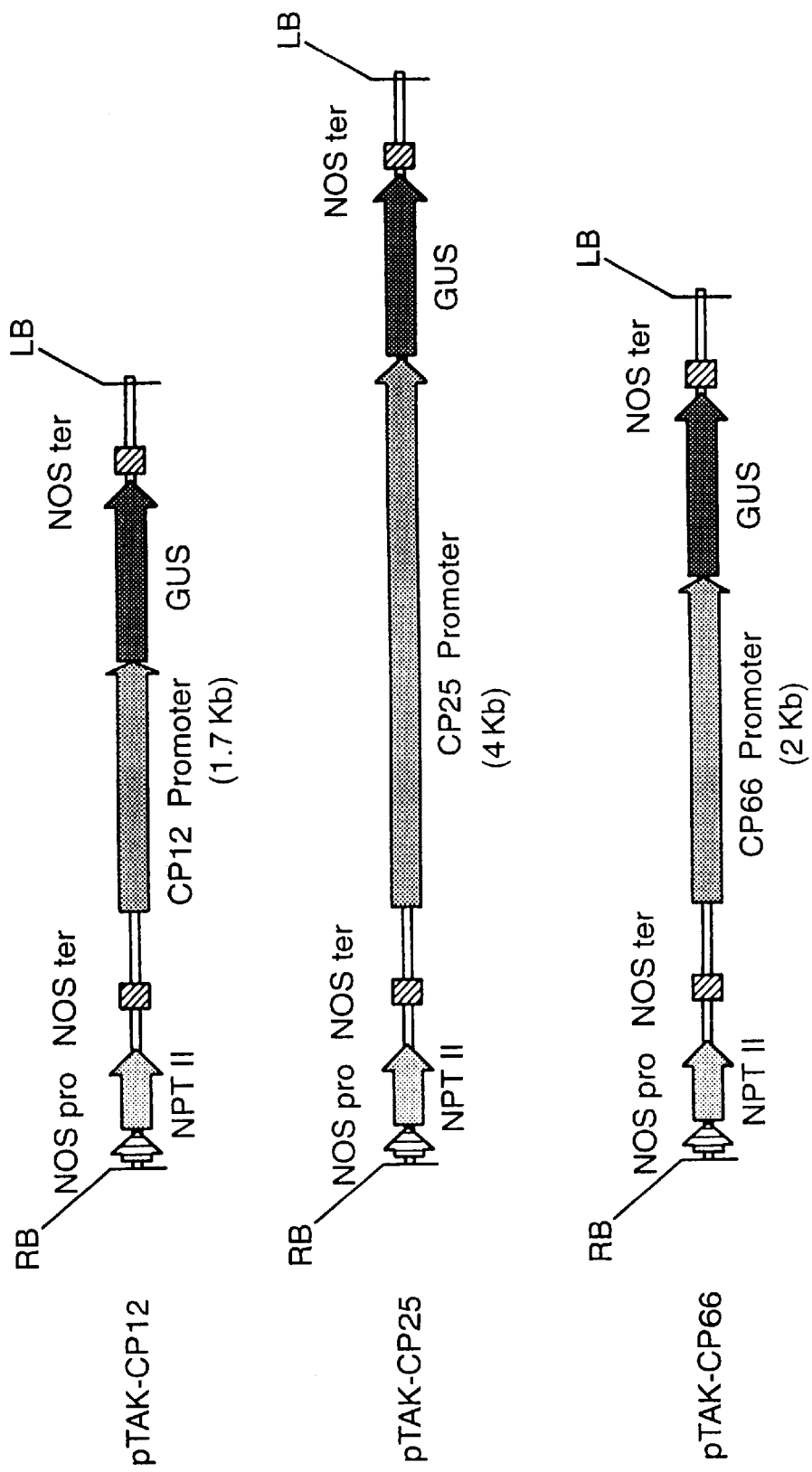

FIG. 23 shows the vector constructs for tobacco transformation.

Figure 24:
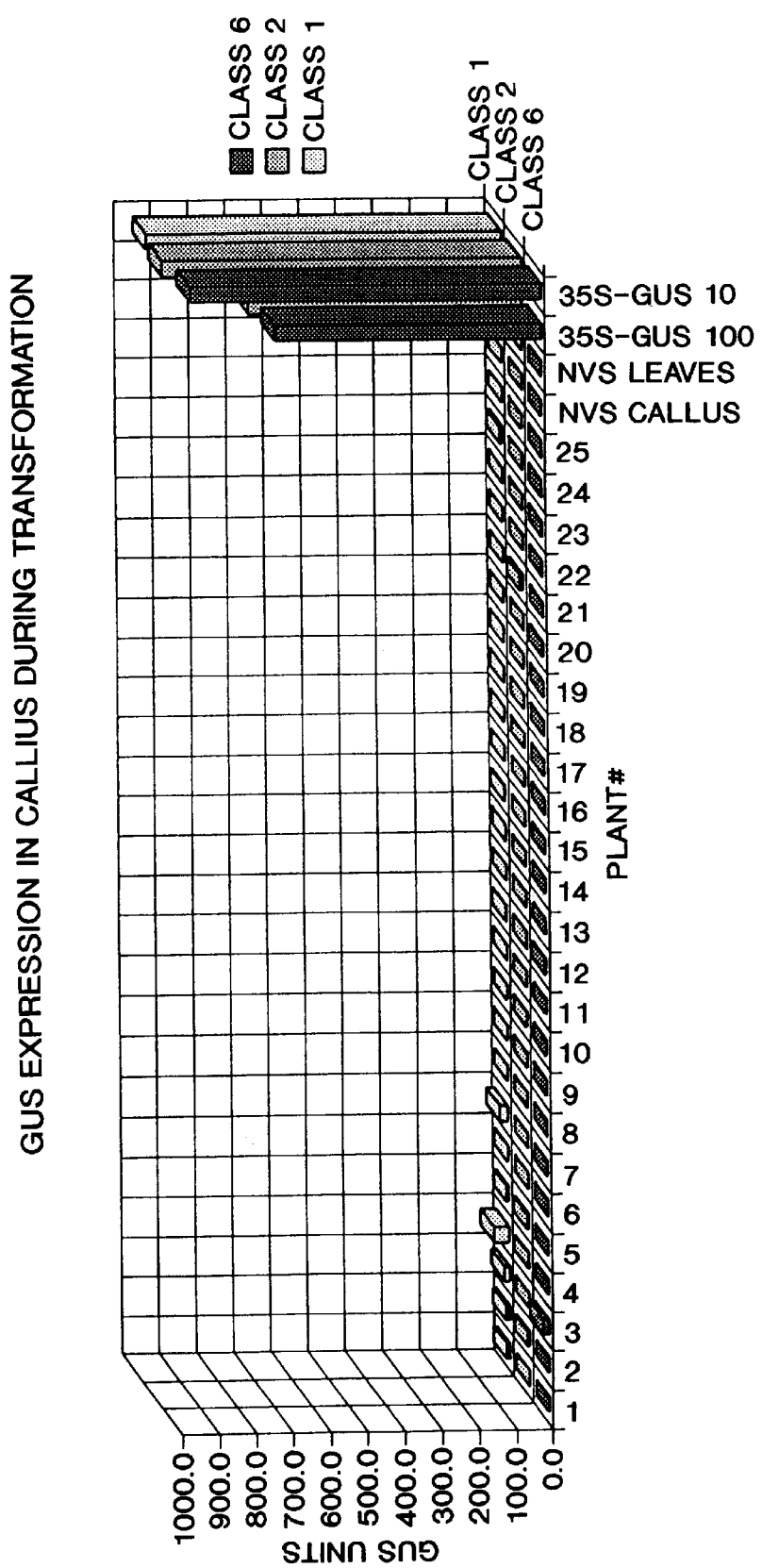

FIG. 24 shows the levels of GUS expression in shoot-generating calli during transformation.

Figure 25:
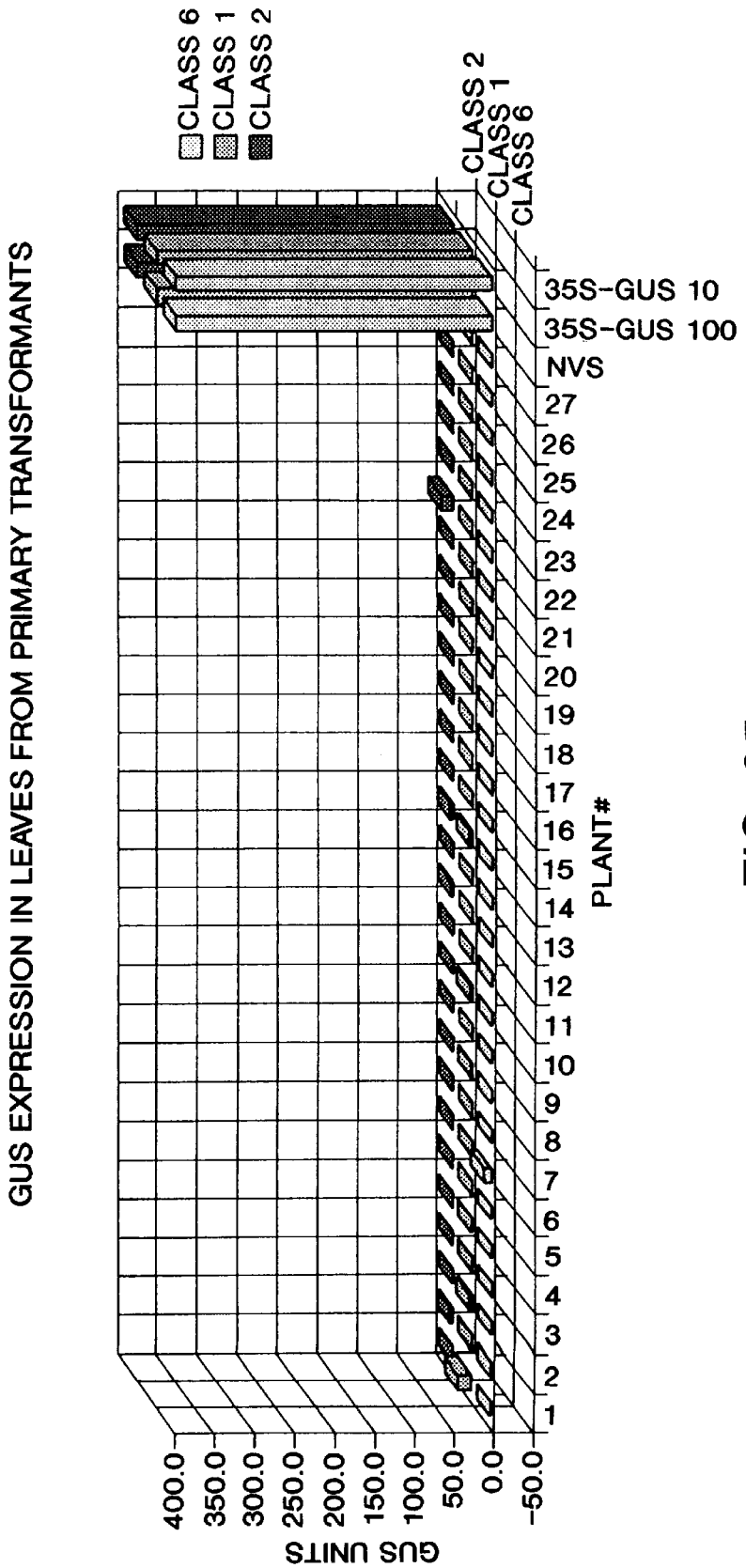

FIG. 25 shows the levels of GUS expression in leaves from primary transformants.

Figure 26:
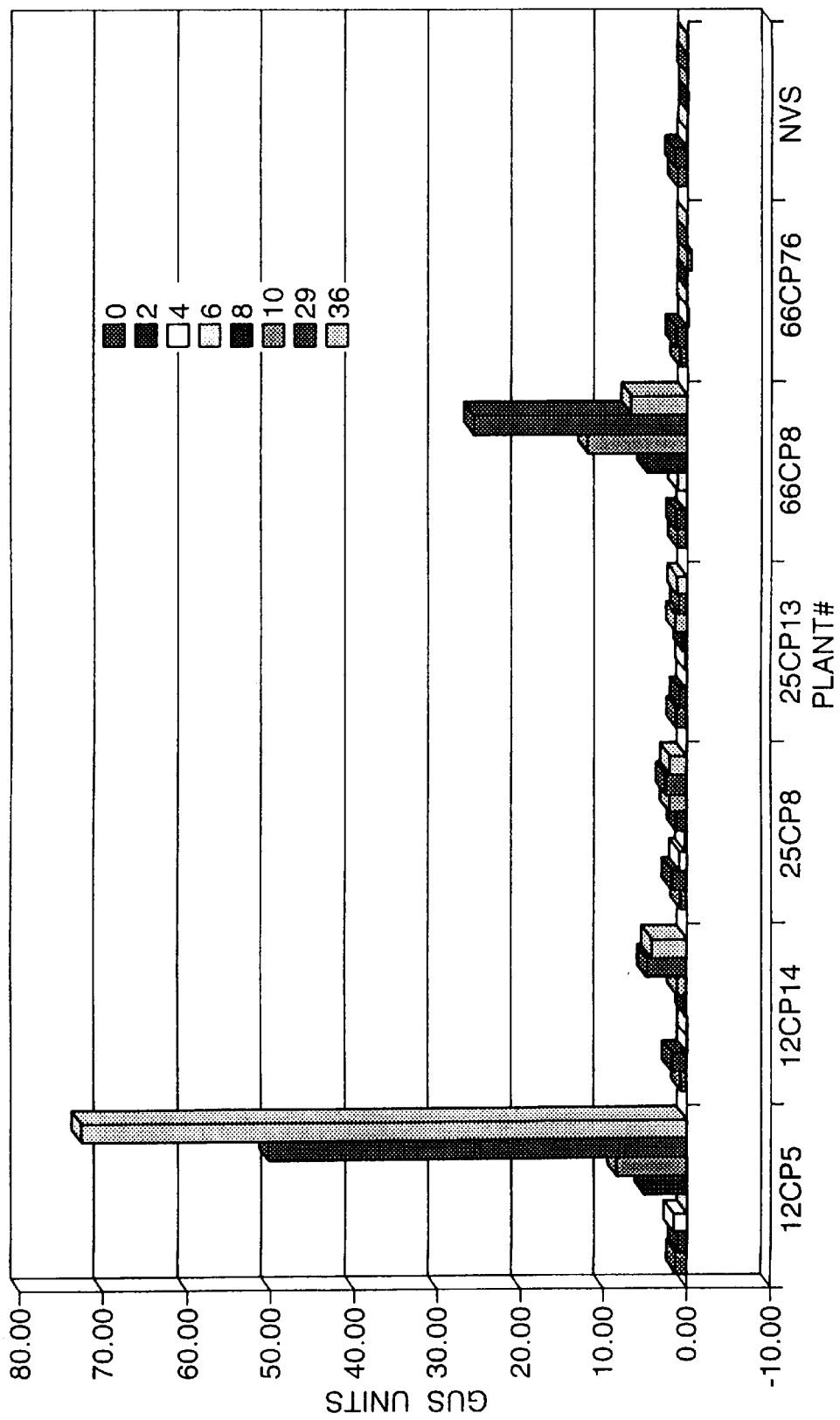

FIG. 26 shows the time course of GUS expression in the progeny of 2 random primary transformants per class, 0 to 36 days after imbibition (DAI). NVS designates the wild type negative control.

Figure 27:
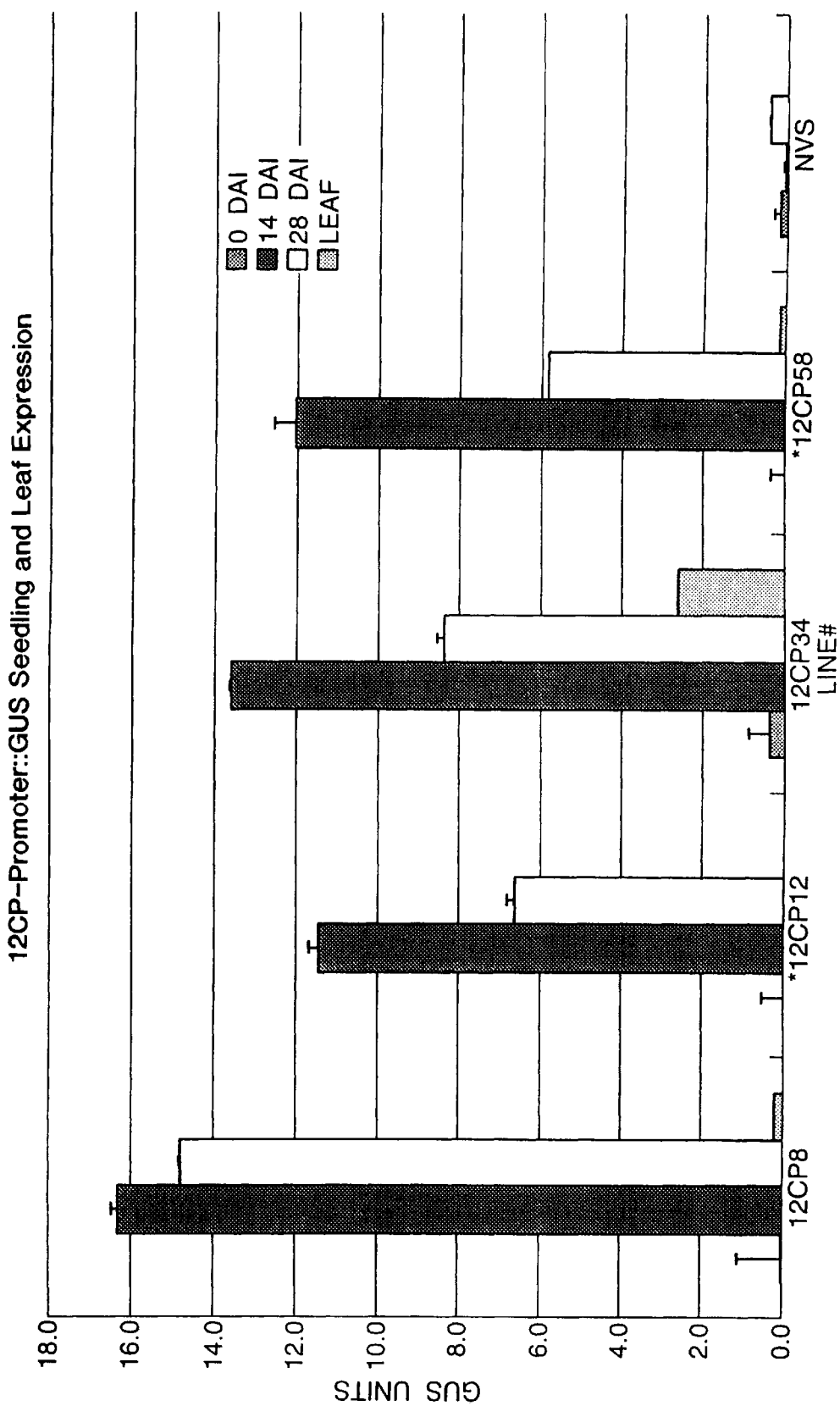

FIG. 27 shows the GUS activity in the progeny of 24 primary transformants of class 1. Seedlings were assessed at 0, 14 and 28 DAI. The Figure also includes the GUS activity in young leaves from the primary transformants.

Figure 28:
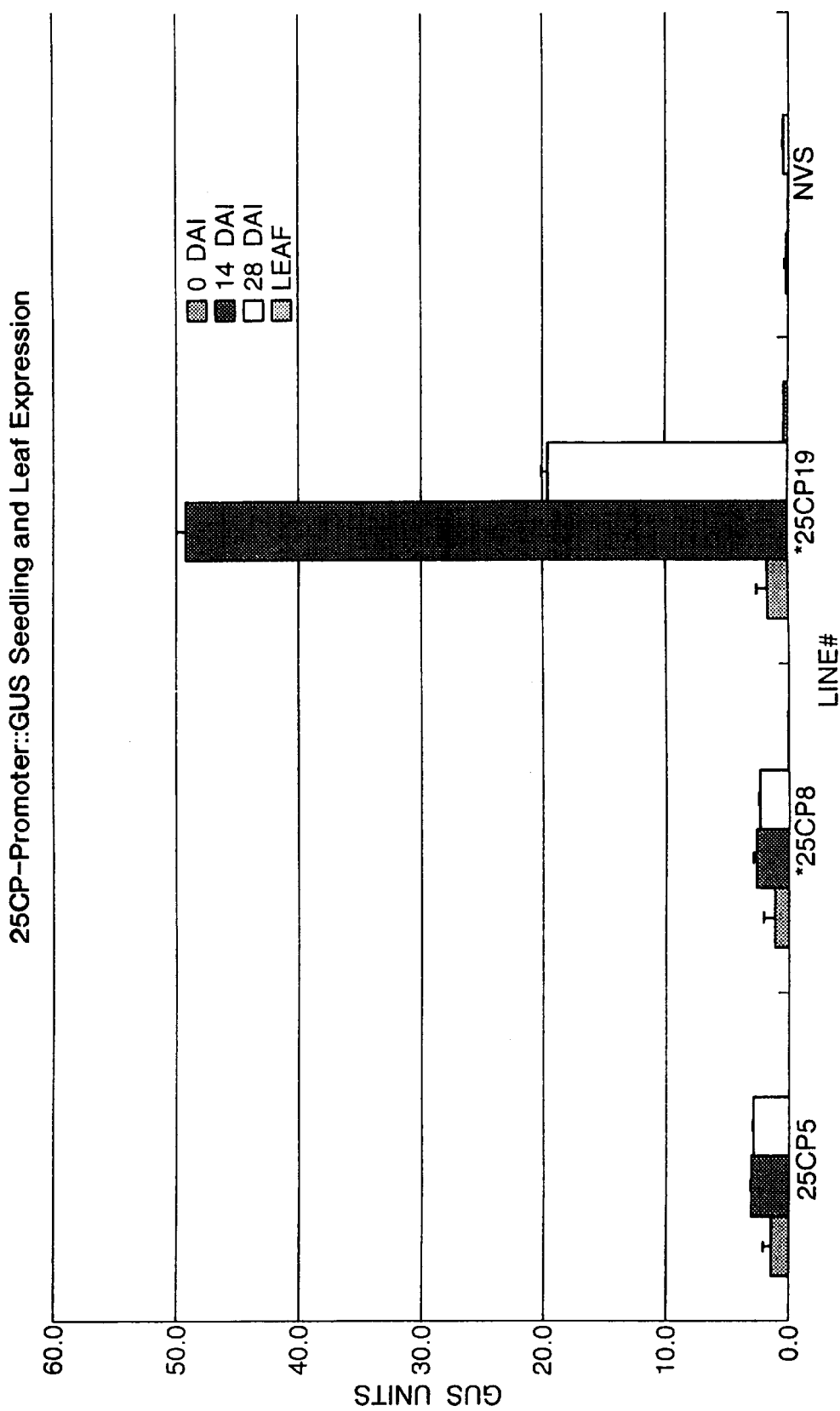

FIG. 28 shows the GUS activity in the progeny of 24 primary transformants of class 2. Seedlings were assessed at 0, 14 and 28 DAI. The Figure also includes the GUS activity in young leaves from the primary transformants.

Figure 29:
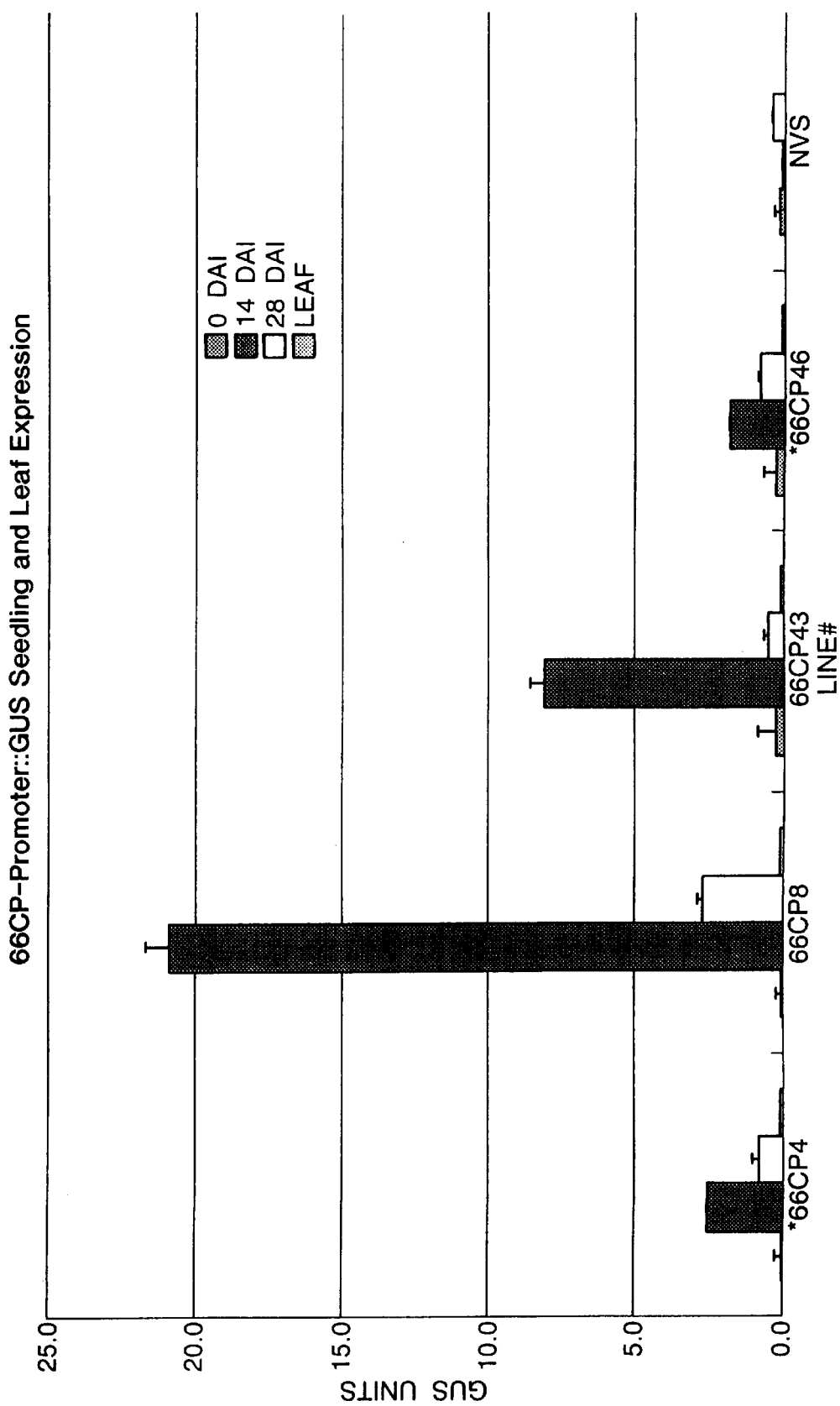

FIG. 29 shows the GUS activity in the progeny of 24 primary transformants of class 6. Seedlings were assessed at 0, 14 and 28 DAI. The Figure also includes the GUS activity in young leaves from the primary transformants.

In general, in the Figures the designations CO or COD in connection with a clone indicate the coding region, and NC or NCD indicates the non-coding region.

In outline, the Examples describe the amplification of a range of germination-expressed cysteine protease partial clones by reverse transcriptase polymerase chain reaction (RT-PCR) on germinating oilseed rape RNA. Preliminary assessment of the clones' expression in dry seeds and germinating seedlings by northern blotting, followed by more detailed northern blot experiments on selected clones to assess their time course of expression. A cDNA library was constructed from tissues showing a high expression of these clones, followed by screening of a genomic library to subclone the promoter areas. Final assessment of the spatial and temporal regulation of the cloned promoters was conducted by transcriptional fusion of the promoter fragments with the β-glucuronidase (GUS) reporter gene and transformation into tobacco.

EXAMPLE 1

Construction of a Cysteine Protease Reverse Transcribed PCR Library from Germinating Oilseed Rape Seedlings In order to identify germination specific sequences, a RT-PCR approach on oilseed rape seedling RNA was utilised. A reverse oligo(dT) primer and forward primers, designed to the cysteine protease coding regions conserved between several plant species, were used to amplify a 750 bp RT-PCR product covering 500 bp of the coding region and about 250 bp of the non-coding region. The 5'-end was sequenced to confirm the identity of the RT-PCR products as cysteine protease related clones. Since there is much less pressure of selection on non-coding regions, significant differences in the 3'-end non-coding regions may predict differences in the 3'-end untranslated regions with an effect on the promoter. This general approach is shown schematically in FIG. 1.

Preparatory Methods

Plant Material

Five grams of oil-seed rape seeds (*Brassica napus*) from the variety Westar were sterilised in 1% sodium hypochlorite for 10 minutes. After several washes in sterile water, seeds were imbibed with sterile water for 12 hours at 4° C. in the dark to synchronise the germination. They were sown on wet sterile Whattman paper and grown at 25° C. in the dark prior to harvesting the cotyledons.

RNA Extraction

Lithium Chloride Method

Total RNA was isolated from dry seeds and three days-old oil seed rape seedlings using a modification of the protocol described by Jepson et al., (1991). Tissues (5 g) were ground with liquid nitrogen in a mortar and pestle until a fine powder was obtained. After addition of 9 ml homogenisation buffer [400 mM NaCl; 50 mM Tris-HCl, pH 9.0; 1% SDS; 5 mM ethylene diamine tetraacetic acid (EDTA); 4 U/ml heparin; 1 mM aurintricarboxylic acid (ATT); 10 mM dithiothreitol (DTT)] and 4.0 ml phenol saturated in homogenisation buffer and supplemented with 10% (v/v) m-cresol before use, the tissues were ground again until a fine paste was obtained. The paste was transferred to a cold corex tube and centrifuged for 15 minutes at 13,000 rpm (Sorval, SS34, 4° C.). The supernatant was transferred to another tube, extracted for 5 minutes with 5 ml of phenol-chloroform and centrifuged for 30 minutes at 9,000 rpm (Sorval, SS34, 4° C.) to recover the aqueous phase. After 3 phenol-chloroform extractions, the RNA was recovered by precipitating the supernatant overnight on ice with one fifth volume of 12M lithium chloride. After centrifuging for 30 minutes at 9,000 rpm (Sorval, SS34, 4° C.), the supernatant was removed and the pellet resuspended in 1 ml of 5 mM Tris (pH 7.5) prior to transfer to a microtube. After a second lithium chloride precipitation overnight, the pellet was washed twice with 70% ethanol, resuspended in 0.2 ml DEPC treated water and stored at −70° C.

Caesium Chloride Method

Total RNA was isolated from a range of developmental stages of oil seed rape seedlings using a protocol modified from Okayama et al (1979). Tissues (2–4 g) were ground in a mortar and pestle with 1 g $Al_2O_3$ in the presence of liquid nitrogen. The powder, kept in dry ice, was then mixed in a corex tube with 8 ml of pre-warmed (65° C.) homogenisation buffer [5M thiocyanate guanidine; 0.5%, w/v, lauryl sarcosine sodium; 0.025M sodium citrate; pH 7.0] supplemented before use with 2.5% (v/v) B-mercaptoethanol, and incubated at 40° C. for 10 minutes with vortexing until complete defrosting of the tissues. After centrifugation at 12,000 rpm for 30 minutes at 15° C. (Sorval, SS34 rotor), the supernatant was recovered, homogenisation buffer added to 8 ml and supplemented with 0.1 g CsCl per ml. After the CsCl had dissolved, the homogenate was added in a 12 ml polyalomer tube containing 2.5 ml of a CsCl high density cushion [5.7M CsCl; 0.1M EDTA] without disturbing the cushion. After centrifugation at 25,000 rpm for 24 hours at 20° C. (Sorval, TH-641 rotor) the supernatant was removed by suction and the wall of the tube cleaned with absorbent paper before resuspension of the RNA loop into 300 μl resuspension buffer [7M urea; 2%, w/v, lauryl sarcosin sodium]. The RNA was then transferred to a 1.5 ml tube and extracted with an equal volume of phenol and an equal volume of chloroform/isoamylic alcohol [24:1, v/v]. Following centrifugation at 13,000 rpm for 5 minutes the aqueous phase was recovered and extracted again with an equal volume of chloroform. The RNA was precipitated overnight at −20° C. by adding a one-tenth volume of 3M sodium acetate and 2.5 volumes of cold ethanol. After centrifugation at 13,000 rpm for 15 minutes at 4° C., the supernatant was discarded and the pellet was washed with 1.5 ml of cold 70% ethanol. The centrifugation was repeated for 10 minutes, the supernatant was discarded and the pellet dried for 3–4 minutes in a speedvacuum. The pellet was resuspended in sterile DEPC-treated water, the RNA precipitated again and the pellet washed, as described above, and finally resuspended in 50 μl DEPC-treated water and stored at −70° C.

Labelling of DNA Probes

Terminal Exchange

The oligos (25–50 ng) were labelled by phosphorylating their hydroxylated 5'-end using 20 U T4 polynucleotide kinase (New England Biolabs) in a 25 μl reaction [30 uCi [$\gamma^{32}$P] ATP (Amersham, 5000 Ci/mmol), 1× kinasing buffer] at 37° C. for 30 minutes. The oligos were purified from the unincorporated nucleotides using G-25 sephadex spun columns (5prime→3prime, Inc®), as recommended by the manufacturer.

PCR

Plasmid DNA (5 ng) was amplified [(94° C., 1 minute; 65° C., 1 minute; 72° C., 1 minute) ×17 cycles; (72° C., 7 minutes)×1 cycle] using 2.5 U of Taq polymerase (Gibco BRL) in a 50 μl PCR reaction [0.25 μM [$\alpha$-$^{32}$P] dATP (Amersham, 3000 Ci/mmol); 0.4 μM DATP; 50 μM other dNTPs; 1.5 mM MgCl2; 0.5 μM oligos; 1×PCR buffer]. The probes were purified from the unincorporated nucleotides using G-50 sephadex spun columns (Pharmacia Biotech), as recommended by the manufacturer.

Random Priming

Plasmid DNA (25–50 ng) was labelled using the "Oligolabelling Kit" (Pharmacia) following manufacturer's recommendations.

Northern Blot Hybridization

Northern blot experiments were performed according to Sambrook et al. Total RNA (10 μg) was mixed with 2.5 vol of loading buffer (5prime→3prime, Inc®), sized by electrophoresis on a 1.2% agarose denaturing gel [1×MOPS(40 mM MOPS, pH 7.0; 10 mM sodium acetate; 1 mM EDTA); 17%, v/v, formaldehyde] in alkaline running buffer [1×MOPS; 7%, v/v, formaldehyde] and transferred to nylon membranes (Hybond N, Amersham) by capillary blotting according to the manufacturer's recommendations. Hybridizations were performed overnight at 65° C. in hybridisation buffer [5×SSPE (900 mM NaCl; 50 mM $NaH_2PO_4.H_2O$; 5 mM EDTA; pH 7.4, NaOH); 0.5% sodium dodecyl sulphate (SDS); 1% powdered milk] supplemented with 100 μg/ml denatured salmon sperm DNA. Blots were washed in 3×SSC [20×SSC: 450 mM NaCl; 45 mM $Na_3citrate.2H_2O$; pH 7.0, HCl] and 1% SDS for 1 hour at 65° C., and exposed to X-ray films (X-OMAT AR, Kodak) at −80° C. with intensifying screen.

RT-PCR Library Construction and Screening

A RT-PCR library was constructed from germinating oilseed rape seedlings using a "Perkin Elmer GeneAmp® RNA PCR Kit" and following the manufacturer's recommendations. Total RNA (1 μg) extracted from cotyledons 3 days after seeds imbibition was reverse transcribed [65° C., 2 minutes; 42° C., 30 minutes; 99° C., 5 minutes; 6° C., 5 minutes] using an oligo(dT) primer (MPRACE1B) (SEQ ID NO: 1) stabilised for the PCR. The heteroduplex DNA-RNA was subsequently amplified by PCR using the same downstream primer as for the reverse transcription and a set of two upstream degenerate primers (DEGCYS1 (SEQ ID NO: 2) and DEGCYS2 (SEQ ID NO: 3)) designed on the peptide level from a motif of cysteine protease coding regions conserved among most of the plant species [GCNCCLM (NED)]. Cycling conditions: [(95° C., 2 minutes; 55° C., 2 minutes; 72° C., 1.5 minutes)×2 cycles; (95° C., 2 minutes; 55° C., 1 minute; 72° C., 1.5 minutes)×33 cycles] followed by 7 minutes at 72° C.

The RT-PCR products were ligated into a pCRII vector before transforming *E. coli* using the "TA Cloning® Kit" (Invitrogen) following the manufacturer's recommendations. This system takes advantage of the non-template dependent activity of thermostable polymerases used in PCR that add a single deoxyadenosine to the 3'-ends of all duplex molecules provided by PCR. This allows direct cloning into a pCRII vector which contains overhanging deoxytimidine. Plasmid DNA was purified using "Wizard DNA miniprep DNA purification system" (Promega) and sequenced by the chain termination method (Sanger et al., 1977) with "Sequenase version 2.0 T7 DNA polymerase" (USB) according to the manufacturer's recommendations.

| OLIGOS | SEQUENCE (5'→3') | SEQ ID NO: |
|---|---|---|
| MPRACE 1B | GGC CAC GCG TCG ACT AGT TAC TCG AGT TTT TTT TTT TTT TTT T | SEQ ID NO: 1 |
| DEGYS 1 | GGI TC(CT) AA(CT) GGI GGI (CT)TI ATG | SEQ ID NO: 2 |
| DEGCYS2 | GGI TC(CT) AA(CT) GGI GGI (CT)TI ATG (GA)A | SEQ ID NO: 3 |

Analysis

The RT-PCR products were analysed by electrophoresis on an agarose gel. As can be seen in FIG. 2, two major 750 bp fragments of the expected size, amplified from cotyledons RNA, but not from seeds RNA were found. These were gel excised and cloned. In a parallel approach, aliquots of the RT-PCR products without gel purification were cloned to generate a three days-old expressed cysteine protease library containing 400 clones from which 22 came from gel excision. A colony screening with the oligos used for the RT-PCR identified 250 putative cysteine proteases. Seven clones from gel excision were taken at random and fully sequenced, all of them were cysteine proteases, and fell into 3 classes.

These clones were given the following designations:

| CLONES | CLASS | SEQ ID NO: |
|---|---|---|
| OSR8.401 | 1 | SEQ ID NO:34 |
| OSR8.402 | 2 | SEQ ID NO:38 |
| OSR8.403 | 2 | SEQ ID NO:36 |
| OSR8.404 | 2 | SEQ ID NO:37 |
| OSR8.406 | 6 | SEQ ID NO:35 |
| OSR.387 | 6 | SEQ ID NO:40 |
| OSR.389 | 6 | SEQ ID NO:39 |

The preliminary DNA sequences of these clones and their alignment is shown in FIGS. 3A-1–3A-8 and 3B-1–3B-3.

Figure 5:
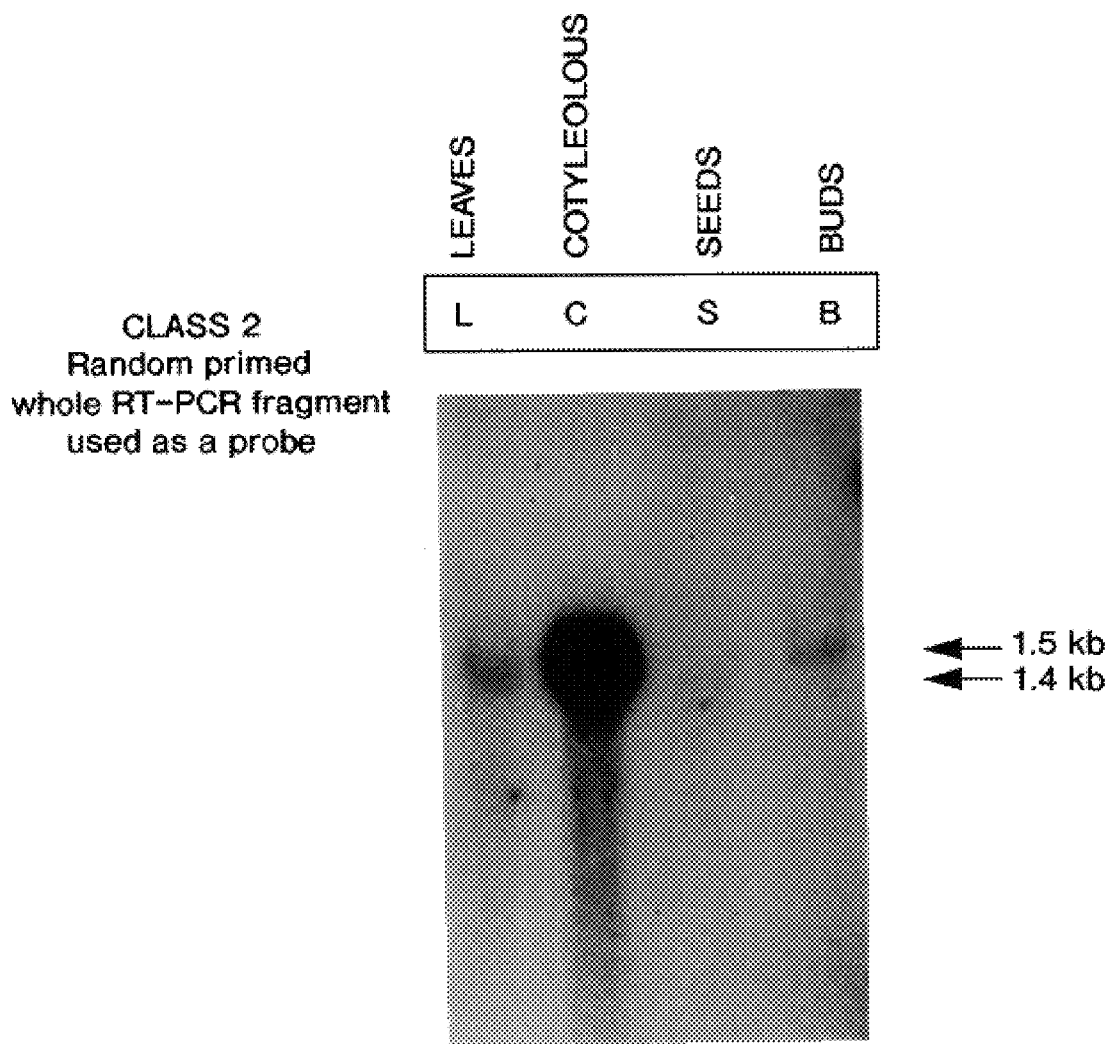

Three clones, one per class, OSR8.401 (SEQ ID NO: 34) (class 1); OSR8.402 (SEQ ID NO: 38) (class 2) and OSR8.389 (SEQ ID NO: 39) (class 6) whose preliminary DNA sequences are shown in FIGS. 4-1–4-4, were labelled by random priming and assessed on northern blots containing total RNA extracted from seeds and cotyledons using the lithium chloride method. They appeared to be well expressed during germination but not in dry seeds. Furthermore, some cross-hybridisation was observed between the different classes due to the nature of the probe. This is illustrated in FIG. 5 which shows the result for the class 2 clone, OSR8.402 (SEQ ID NO: 38), with a random primed whole RT-PCR fragment as probe.

The library was then screened using the five cysteine protease clones labelled by random priming. No new classes were clearly identified, all the diversity of clones was present in the gel-excised fragments. The expression pattern of the three classes of clones was assessed by northern blots with RNA, extracted with the caesium chloride method, from a range of developmental stages as shown in FIG. 6. For class 2 and 6, hybridisations were performed using the 3'-non coding regions of clones OSR8.402 (SEQ ID NO: 38) and OSR8.389 (SEQ ID NO: 39) respectively, to avoid any cross-hybridisation. For class 1, a part of the coding region of OSR8.401 clone was used as a probe because no non-coding region was available in the RT-PCR clones. To increase the specificity, probes were labelled by PCR using the oligo(dT) reverse primer (MPRACE1B) (SEQ ID NO: 1) and an internal reverse primer (CYS8.402 (SEQ ID NO: 6) and CYS8.389 (SEQ ID NO: 7)) for classes 2 and 6, whilst using 2 internal primers (CYS8.401 (SEQ ID NO: 4) and CYS8.401R (SEQ ID NO: 5)) for class 1. Classes 2 and 6 are expressed following seed imbibition and for the first 45 days of early seedling growth but are not expressed in mature plant organs or in the developing seed. Class 1 shows some expression in buds and leaves but this may be the result of some cross-hybridisation due to the nature of the probe. Class 2 is highly related to COT44, the only cysteine protease published for oilseed rape (Comai and Harrada, 1989). FIGS. 7-1–7-4 show alignment of deduced amino acid sequences of the clones with COT44. The clones shown in FIG. 7 have the following sequence designations:

| CLONE | SEQ ID NO: |
|---|---|
| OSR8.403CO | SEQ ID NO: 42 |
| OSR8.404CO | SEQ ID NO: 43 |
| OSR8.402CO | SEQ ID NO: 44 |
| OSR8.389CO | SEQ ID NO: 45 |
| OSR8.387CO | SEQ ID NO: 46 |
| OSR8.406CO | SEQ ID NO: 47 |
| OSR8.401CO | SEQ ID NO: 48 |

| OLIGOS | SEQUENCE (5'→3') | SEQ ID NO: |
|---|---|---|
| CYS8.401 | TAT CCT TAT CAA GAA CGT GAT GGC A | SEQ ID NO:4 |
| CYS8.401R | CCT ACG ATG AGC ACT GCG TGG T | SEQ ID NO:5 |
| CYS8.402 | GCA GTA ATC AAA TTG GGA TTG TTA TAA | SEQ ID NO:6 |
| CYS3.389 | CGT GGA ACC AGC AGT GTT TGA AGT T | SEQ ID NO:7 |

EXAMPLE 2

Construction of a Standard Oligod(T) Primed and a Cysteine Protease Specifically Primed cDNA Library from Germinating Oilseed Rape Seedlings As the RT-PCR products were not full length and to avoid PCR generated mutations, an oilseed rape cDNA library was constructed from a developmental stage showing a high expression of the three clones of interest. A specifically primed library was constructed using two specific oligos designed on the basis of the three classes of RT-PCR clones, rather than using an oligo(dT) primer. As a result only the cysteine protease clones were reverse transcribed, which provided a small number of short clones of about 650 bp, all of them being full length at the 5'-end. This allowed the design of oligos to the 5'-non-coding regions for use in screening a standard oligo(dT) primed cDNA library directly for full length clones. This general approach is shown in schematically in FIG. 8.

Preparatory Methods

Plant material

Five grams of oilseed rape seeds (*Brassica napus*) from the variety Westar were sterilised in 1% sodium hypochlorite for 10 minutes. After several washes in sterile water, seeds were imbibed with sterile water for 12 hours at 4° C. in the dark to synchronise the germination. They were sown on wet sterile Whattman paper and grown at 25° C. in the dark for 2 days prior to harvesting the cotyledons.

RNA Extraction and Purification

Total RNA was isolated from 2 days-old oil seed rape seedlings using the caesium chloride method described previously. Polyadenylated RNA was purified from 1 mg of total RNA using a "PolyATract mRNA isolation system" (Promega), according to the manufacturer's recommendations. The system uses a biotinylated oligo(dT) primer to hybridise at high efficiency in solution to the 3'-poly(A) region of the mRNAs. The hybrids were then captured and washed at high stringency using streptavidin coupled to paramagnetic particles and a magnetic separation strand, prior to elution with water.

cDNA Library Construction and Screening

The standard oligo(dT) primed cDNA library and the cysteine protease specifically primed library were constructed from 2 days-old oilseed rape poly(A) RNA (5 µg), using a lambda "ZAP-cDNA® Synthesis Kit" (Stratagene). The manufacturer's recommendation were followed strictly although, for the specific library, the reverse transcription was primed using a mix of two specific oligos (CDNA8.401R (SEQ ID NO: 8) and CDNA8.387R (SEQ ID NO: 9)) respectively for the class 1 and for classes 2 and 6 of the RT-PCR clones, modified to include a Xho I site at their 5'-end. The second strand was synthesised by nick-translation using DNA polymerase I, after treatment of the heteroduplex with RNase H. The cDNAs were filled in with Klenow, ligated to EcoR I adapters and digested with Xho I prior to size-fractionation on Sepharose®-400 spun column (Pharmacia) and directional cloning as an EcoR I-Xho I insert into the polylinker of pBluescript phagemid contained within the Uni-ZAP vector arms. Lambda-ZAP is a replacement lambda which has been engineered to contain pBluescript phagemid, which polylinker is used for cloning the cDNAs.

The library was packaged in vitro using Gigapack® II Gold packaging extract (Stratagene), plated on *E. coli* cell line XL1-Blue MRF' and transferred onto nylon membranes (Hybond N, Amersham) according to the manufacturer's recommendations. Labelling of probes, hybridisations and washes were performed as described previously.

Selected lambda-ZAP clones were excised in vivo to recover the cloned cDNA as a phagemid in pBluescript SK⁻. *E. coli* SolR cells were co-transfected with the recombinant lambda-ZAP and with a helper phage which provided the proteins necessary for the synthesis of a single strand of DNA which, once circularised, provide a functional phagernid.

Analysis a) A small cysteine proteaseenriched specifically primed cDNA library containing $1.10^4$ plaque forming units (pfu) was obtained from 2 days-old oilseed rape cotyledons. $5.10^3$ pfU were plated and transferred onto three replicate membranes to check for cross-hybridisation. Membranes were screened with 3 oligos (CYS8.401MR (SEQ ID NO: 10), CYS8.402MR (SEQ ID NO: 11), CYS8.406MR (SEQ ID NO: 12)) designed respectively to the 5'-end of classes 1, 2 and 6 of the RT-PCR clones and labelled as described above.

Five similar but distinct 5'-end cysteine protease cDNAs containing a short 5'-untranslated region and 650 bp of coding region were obtained, excised in vivo and sequenced. They fall into class 2 and class 6 but no 5'-end cDNA was found for class 1. Although clones from class 2 are highly related to COT44 cDNA (Comai and Harrada, 1989), their 5'-end is 160 bp longer. This indicates that COT44 is missing, 46 amino acids (aa) corresponding to the signal peptide and to a part of the propeptide. This is further illustrated by FIGS. 9-1 and 9-2 which shows the alignment of the deduced amino acid sequence of the cDNA clones CYS2UP6 (SEQ ID NO: 52), CYS2UP7 (SEQ ID NO: 53) and CYS2UP8 (SEQ ID NO: 54) from class 2 with COT44.

Two oligos (CYS6B-UP (SEQ ID NO: 13) and CYS6A-UP (SEQ ID NO: 14)) were designed to the 5'-non-coding region of respectively, cDNAs from classes 2 and 6, to screen the standard oligo(dT) primed library directly for full length clones. The preliminary sequence alignment of the clones with each other and COT 44 is shown in FIGS. 10-1–10-6. The clones shown in FIG. 10 have the following sequence designations:

| CLONE | SEQ ID NO: |
|---|---|
| CYS2UP6 | SEQ ID NO:52 |
| CYS2UP7 | SEQ ID NO:53 |
| CYS2UP8 | SEQ ID NO:54 |
| CYS6UP3NCOD | SEQ ID NO:55 |
| CYS6UP5NCOD | SEQ ID NO:56 |
| CYS6UP2NCOD | SEQ ID NO:57 |
| CYS6UP4NCOD | SEQ ID NO:58 |

| OLIGOS | SEQUENCE (5'→3') | SEQ ID NO: |
|---|---|---|
| CDNA8.401R | GAG AGA GAG AGA GAG AGA GAA CTA GTC TCG AGT CCC ATG GTT TTT AAT | SEQ ID NO:8 |
| CDNA8.387R | GAG AGA GAG AGA GAG AGA GAA CTA GTC TCG AGC CGC CGT TTT TCA T | SEQ ID NO:9 |

| OLIGOS | SEQUENCE (5'→3') | SEQ ID NO: |
|---|---|---|
| CYS8.401MR | CCC ATG GTT TTT AAT GAC AAA TTG AAA A | SEQ ID NO:10 |
| CYS8.402MR | CCC CCG TTT TTC ATT ATG AAT TGA AA | SEQ ID NO:11 |
| CYS8.406MR | CGC CGT TTT TCA TGA TGA ATT GAA AA | SEQ ID NO:12 | b) A representative oligo(dT) primed cDNA library containing $1.10^7$ pfu was obtained from 2 days-old oilseed rape cotyledons. The size of the inserts, estimated by PCR, is ranging from 0.75 kb to 3 kb with an average insert size of 1.5 kb. 1.10⁶ pfu were plated and transferred onto three replicate membranes to check for cross-hybridisation. Membranes were first screened with a 5'-end oligo (CYS8.401MR (SEQ ID NO: 10), CYS6B-UP (SEQ ID NO: 13) and CYS6A-UP (SEQ ID NO: 14)) designed respectively to the 5'-end coding region of class 1 RT-PCR clones and to the 5'-untranslated region of class 2 and class 6 cDNAs to identify fill length clones for class 2 and 6 (class 1, 20 positives; class 2, 250 positives; class 6, 130 positives).

| OLIGOS | SEQUENCE (5'→3') | SEQ ID NO: |
|---|---|---|
| CYS8.401MR | CCC ATG GTT TTT ATT GAC AAA TTG AAA A | SEQ ID NO:10 |
| CYS86B-UP | TAG AAA ACC AAC AAA ACA AAC ATA CAA T | SEQ ID NO:13 |
| CYS6A.UP | GAA CAA CCA AGC CAA ACA TAC AAT AT | SEQ ID NO:14 |

The same membranes were screened again with the 3'-end probes used on the developmental northern blots to ensure the correct form was chosen. For classes 2 and 6, hybridisations were performed using the 3'-non-coding regions labelled by PCR to avoid any cross hybridisation. For class 1, a part of the coding region was used as a probe because non-coding region was not available in the RT-PCR clone (class 1, 84 positives; class 2, 205 strong positives; class 6, 85 strong positives).

Comparison between the number of clones identified with both specific probes (5' and 3') confirmed that most of the cysteine protease cDNA clones present in the library are full length.

Ten clones per class which hybridised with (5' and 3' probes) but did not cross hybridise with probes from the two other classes were plaque purified and four clones per class were excised in vivo. Six full length cysteine protease cDNA clones falling into the three classes of cysteine proteases identified from the RT-PCR work were isolated and fully sequenced (two for class 1, three for class 2, and one for class 6). The alignment of the cDNA clones is shown in FIGS. 11-1–11-21. They fall into 3 classes of CP related to the papain super family and the pre-proenzymes share 52% (class 1), 90% (class 6) and 96% (class 2) identity with cot44. FIGS. 12 to 17 show the nucleic acid sequences of clones CDCYS12 (SEQ ID NO: 59), CDCYS14 (SEQ ID NO: 60), CDCYS22 (SEQ ID NO: 61), CDCYS24 (SEQ ID NO: 62), CDCYS25 (SEQ ID NO: 63) and CDCYS66 (SEQ ID NO: 64) respectively. The peptide sequences were predicted and showed the characteristic features present in most of the plant cysteine proteases, as shown in FIGS. 18-1–18-6 for clones CDCYS12, CDCYS14, CDCYS22, CDCYS24, CDCYS25 and CDCYS66 (SEQ ID NO: 64). The clones shown in FIG. 11 have the following designations:

| CLONE | SEQ ID NO: |
|---|---|
| CDCYS22 | SEQ ID NO:61 |
| CDCYS24 | SEQ ID NO:62 |
| CDCYS25 | SEQ ID NO:63 |
| CDCYS66 | SEQ ID NO:64 |

-continued

| CLONE | SEQ ID NO: |
|---|---|
| CDCYS12 | SEQ ID NO:60 |
| CDCYS14 | SEQ ID NO:61 |

The predicted amino acid sequences in FIG. 18 have the following sequence designations:

| Predicted Amino Acid Sequence CLONE | SEQ ID NO: |
|---|---|
| CDCYS12.P | SEQ ID NO:65 |
| CDCYS14.P | SEQ ID NO:66 |
| CDCYS22.P | SEQ ID NO:67 |
| CDCYS24.P | SEQ ID NQ:68 |
| CDCYS25.P | SEQ ID NO:69 |
| CDCYS66.P | SEQ ID NO:70 |

EXAMPLE 3

Screening of an Oilseed Rape Genomic Library and Subcloning and Characterisation of the Promoter Regions Oligonucleotide probes were generated to the 5'-end non-coding region of one cDNA clone per class and used to screen a genomic library in order to isolate clones carrying the promoter regions. For each class, genomic clones were isolated and the promoter subcloned into a phagemid for more precise characterisation and deletion.

Genomic Library Construction and Screening

An amplified λEMBL-3 random genomic library (Clontech) from oilseed rape (*Brassica napus* cv. Bridger) was constructed. DNA was partially digested with Mbo I and the fragments were separated on a sucrose gradient to produce size range between 8 to 22 kb before cloning into the BamH I site of a λEMBL-3 replacement vector. The library was plated on *E. coli* strain LE392 cells. Screening and plaque purification were performed as described by Sambrook et al. (1989). Genornic clones corresponding to the three classes of cDNAs were isolated and λDNA mini-preparations were carried out using a protocol from Grossberger (1987). Genomic clones were mapped using their restriction fragment length polymorphism (RFLP) patterns: clones were digested with a set of restriction enzymes, analysed on a 0.8% agarose gel and simultaneously transferred onto two membranes (Hybond N, Amersham) according to Sambrook et al., (1989) prior to hybridisation.

Analysis

For the primary screening twenty genome-equivalent (2.10⁶ pfu) were plated and transferred onto three replicate membranes to check for cross-hybridisation. Membranes were hybridised with 3 oligos (CDNA12 (SEQ ID NO: 15), CDNA25 (SEQ ID NO: 16) and CDNA66 (SEQ ID NO: 17)) designed respectively to the 5'-end of classes 1, 2 and 6 of the cDNA clones, to get as close as possible to the promoter area (class 1, sixteen strong positives; class 2, nine strong positives; class 6, eight strong positives). No cross-hybridisation was detected between the three classes and ten clones per class were chosen for a secondary screening.

| OLIGOS | SEQUENCE (5'→3') | SEQ ID NO: |
|---|---|---|
| CDNA12 | ATC GTC TTC TTC CTT TGT TTC TCT CA | SEQ ID NO:15 |
| CDNA25 | CTT CGT CAG CGA AAC TCC TCT CTT | SEQ ID NO:16 |
| CDNA66 | CAG AAC TAG AAC AAC CAA GCC AAA C | SEQ ID NO:17 |

The secondary screening was performed using 3'-end PCR probes as described in connection with FIG. 6, to specifically detect the genomic clones corresponding to the RT-PCR clones assessed by northern blots. Some of the clones were not identified by these probes (one for class 1 and two for class 6), since these were likely to be short clones in their 3'-end, thus useful for promoter isolation, they were rescued using the probes from the primary screening. Ten clones per class were plaque purified by two more rounds of purification using the probes from the primary screening. In order to avoid redundant clones (amplified, random library), DNA was prepared from eight genomic clones per class and characterised by RFLP. Clones were cut with Sal I and BamH I, analysed on a 0.8% agarose gel, transferred onto replicate membranes and hybridised with two sets of probes. Oligos were designed to the 5'-non-coding region (CDNA12 (SEQ ID NO: 15), CYS6B-UP (SEQ ID NO: 13) and CYS6A-UP (SEQ ID NO: 14)) and to the middle of the coding region (CYS8.401MR (SEQ ID NO: 10), CYS8.402MR (SEQ ID NO: 11) and CYS8.406MR (SEQ ID NO: 12)) of cDNA clones CDCYS12 (SEQ ID NO: 59), CDCYS25 (SEQ ID NO: 63) and CDCYS66 (SEQ ID NO: 64) respectively.

Four remaining clones per class (12g4, 12g5, 12g6, 12g8; 25g2, 25g4, 25g5, 25g7; 66g1, 66g4, 66g8 and 66g9) were further characterised using another round of digestion/hybridisation. Class 1 cDNAs contain a Bgl R site 500 bp from the translation start and class 2 and 3 cDNAs contain a Hind III site 300 bp from the translation start, these enzymes were used in association with and without Sal I, which releases the insert, to generate genomic fragments suitable for subcloning. PCR experiments were carried out on genomic DNA and cDNAs to predict the size of the promoter area by identifuing putative introns. PCR, using a forward primer in the 5'-non-coding region and a reverse primer located after the Bgl II and Hind III restriction sites, showed the presence of a 400 bp intron within the first 600 bp of class 1 cDNAs whilst no intron was present within the first 300 bp of class 2 and class 6. Promoter fragments with a predicted size in the range of 2–5 kb were identified for one genomic clone per class (12g6, 25g7 and 66g1), ready to be subcloned into pBluescript KS$^{+}$.

EXAMPLE 4

Characterisation of Transcription Starts

Genomic lambda-fragments containing the promoter were subcloned into pBluescript KS$^+$ for more precise characterisation. Sequencing allowed the identification of putative transcription signals before mapping the actual transcription start by primer extension experiments. This involved the extension of a labelled reverse primer designed in an area close to the translation start. After degradation of the RNA template the extension products were sized in a polyacrylamide gel.

Analysis

Genomic fragments containing the promoter were subcloned into pBluescript as a Bgl II-2.6 kb insert cloned in BamH I for class 1 (pKS12P6) (SEQ ID NO: 71), as a Hind III-4.2 kb insert for class 2 (pKS25P7) (SEQ ID NO: 72) and as a BamH I-Hind III-2.4 kb insert for class 6 (pKS66P1) (SEQ ID NO: 73). Sequencing with pUC1 and pUC4 vector oligos and with two internal reverse primers designed to the 5'-end of the cDNAs (CDNA14R (SEQ ID NO: 18) for class 1 and CDNA66R (SEQ ID NO: 19) for class 2 and 6), allowed the orientation of the clones and the identification of putative transcription signals (Pautot et al.,1989). The full nucleotide sequence of the promoters from the sub-cloned genomic fragments is given in FIG. 19 (SEQ ID NO:71), FIG. 20 ( SEQ ID NO:72) and FIG. 21 (SEQ ID NO:73) respectively for class 1, 2 and 6.

| OLIGOS | SEQUENCE (5'→3') | SEQ ID NO: |
|---|---|---|
| CDNA14R | GAA GAA ACT AGA AGA AGG GAG AAG AA | SEQ ID NO:18 |
| CDNA66 | TCA CTT CTT CAT CGG TTC TCC A | SEQ ID NO:19 |

Transcription starts have been mapped precisely by primer extension experiments according to Sambrook et al. (1989) modified as follows. Oligos (CYSGE12R (SEQ ID NO: 20), CYSGE25R (SEQ ID NO: 21) and CYSGE66R (SEQ ID NO: 22)) designed respectively for class 1, 2 and 6 were labelled by terminal exchange as described previously. Total RNA (50 ug), isolated from 3 days-old oilseed rape cotyledons using the caesium chloride method, was precipitated together with 2 ng of primers and resuspended in 30 $\mu$l hybridisation buffer [1 mM EDTA; 400 mM NaCl; 40 mM Pipes, pH 6.4; 70%, v/v, deionised formamide]. Annealing was performed overnight at 32° C. following denaturing at 85° C. for 10 minutes. After precipitation and resuspension in 25 $\mu$l of reverse transcription buffer [50 mM KCl; 10 mM MgCl$_2$; 1 mM dNTPs; 1 U/ul RNase inhibitor], the primers were extended for 90 minutes at 42° C. with 2.5 U MuLV reverse transcriptase (Perkin-Elmer). Template RNA was degraded for 30 minutes at 37° C. with 20 U of RNase (RNace-it, Stratagene). For each class, the extension products were analysed on a polyacrylamide denaturing gel in parallel with a sequencing reaction performed on the genomic clones (pKS12P6 (SEQ ID NO: 71), pKS25P7 (SEQ ID NO: 72) and pKS66P1 (SEQ ID NO: 73)) using the same primers as for the primer extension.

| OLIGOS | SEQUENCE (5'→3') | SEQ ID NO: |
|---|---|---|
| CYSGE12R | AGG AAG AAG ACG ATG ATG GTG ACA | SEQ ID NO:20 |
| CYSGE25R | GTA CAA GAG AAG TAA AGA GAG GAG T | SEQ ID NO:21 |
| CYSGE66R | CGT ATA GGA GAA GTA AAG AAA TGA GT | SEQ ID NO:22 |

As shown in FIG. 22, class 1 transcription start is in a good context [$t_{27}T_{35}C_{49}A_{78}a_{18}C_{45}g_{8\%}$] compared to 49 other plant genes compiled by Pautot et al. (1989). Conserved nucleotides are in capitals, important ones are in bold and the transcription start point is underlined. This transcription start has been mapped 22 nucleotides downstream a putative TATA box localised 179 nucleotides before the translation start and 152 nucleotides upstream the longest cDNA.

Although the consensus for the TATA box is not optimal [$c_{34}a_{18}t_{32}t_{34}a_3A_{97}T_{90}A_{94}a_{47}A_{95}a_{30}A_{71}G_{44\%}$] (SEQ ID NO: 87) compared to 79 other plant genes compiled by Pautot et al. (1989), this result is a confirmation of a previous primer extension experiment using an oligo priming 34 nucleotides downstream the ATG. The distance between the transcription start and the longest cDNA might be explained by the presence of an intron within the 5'untranslated region or by the existence of an alternative transcription start point.

The Class 2 transcription start is in a good context [$a_{18}a_{20}a_{22}\underline{A_{78}}T_{49}C_{45}A_{43\%}$], and has been localised 33 nucleotides after a putative TATA box fitting very well within the plant consensus [$T_{37}g_{11}g_{14}t_{34}T_{96}A_{97}T_{90}A_{94}a_{47}A_{95}T_{63}A_{71}G_{44\%}$] (SEQ ID NO: 38). This corresponds to 53 nucleotides before the translation start and 26 nucleotides upstream the cDNA (FIG. 22).

Class 6 transcription start is nearly in the same context as class 2 [$g_{18}a_{20}a_{22}\underline{A_{78}}T_{49}C_{45}A_{43\%}$] and has been localised 30 nucleotides after a putative TATA box showing exactly the same consensus as for class 2. This corresponds to 51 nucleotides before the translation start and 19 nucleotides upstream the cDNA (FIG. 22).

EXAMPLE 5

Promoter Excision

Prior to fusion with the reporter genes, promoters must be cut precisely between the transcription start and the translation start. Since no useful restriction site was available for the class 2 and 6 genomic clones, a site was engineered into a PCR fragment used to replace a corresponding endogenous fragment.

Analysis

A Hind III site was introduced by PCR on class 1 genomic clone, 2 nucleotides before the translation start, in order to eliminate the remaining part of coding region. The 270 bp fragment was generated by 15 cycles of PCR on pKS12p6 DNA (SEQ ID NO: 71), using CYSGE12C (SEQ ID NO: 23) and CYSG12CR (SEQ ID NO: 24) oligos.

In the same way, a BamH I site was introduced before the translation start of class 2 and class 6 genomic clones using 2 sets of oligos (CYSGE25C (SEQ ID NO: 25), CYSG25CR (SEQ ID NO: 26) and CYSGE66C (SEQ ID NO: 27), CYSG66CR (SEQ ID NO: 28)) respectively on pKS25p7 (SEQ ID NO: 72) and pKS66p1 DNA (SEQ ID NO: 73) to generate a 165 bp fragment.

For class 1, pKS12p6 (SEQ ID NO: 71) was cut with Bsm I and Hind III and gel recovered to excise a 900 bp fragment prior to replacement with the PCR fragment cut by Bsm I and Hind III, to generate pKS12P.

For class 2, pKS25p7 (SEQ ID NO: 72) was cut with Sph I and BamH I, gel recovered to excise a 460 bp fragment and ligated to the replacement PCR fragment cut by Sph I and BamH I, to generate pKS25P.

For class 6, pKS66p1 (SEQ ID NO: 73) was cut with Hind III, filled in with Klenow fragment of DNA polymerase I, cut with Sph I and gel recovered to excise a 440 bpfragment. The PCR fragment was blunt ended with T4 DNA polymerase, cut with Sph I and cloned into the deleted pKS66p1 (SEQ ID NO: 73) to generate pKS66P.

| OLIGOS | SEQUENCE (5'→3') | SEQ ID NO: |
|---|---|---|
| CYSGE12C | GTA ATG GCC TAG CCT GTC TGG C | SEQ ID NO:23 |
| CYSG12CR | GAT GAT GGT GAC <u>AAG CTT</u> TTT CTT ACA GG | SEQ ID NO:24 |
| CYSGE25C | CTA TCT TGC ATG CCC ATT ATT ACT TT | SEQ ID NO:25 |
| CYSG25CR | ACG AAG CC<u>G GAT CCT</u> ATG TTT GTT TTG TTG | SEQ ID NO:26 |
| CYSGE66C | CAT CTT GCA TGC CCA TTA CTG CAT | SEQ ID NO:27 |
| CYSG66CR | AGG AAG CC<u>G GAT CCT</u> ATG TTT GGC TTG G | SEQ ID NO:28 |

EXAMPLE 6

Promoter-GUS Constructs

In order to assess the spatial and temporal regulation of the cloned promoter regions in an heterologous system and under different biotic and environmental conditions, they were used them to drive a reporter gene into tobacco. Transcriptional fusions between each promoter fragment and the β-glucuronidase (GUS) gene were engineered for plant assays and histochemical localisation. For the avoidance of doubt, a reporter gene is used here for convenience only, and to demonstrate the principles involved. In non-test situations the gene controlled by the promoter of the present invention will be that which produces the desired effect.

Plasmid Construction

Standard recombinant DNA methods were adopted in the construction of plasmid vectors (Sambrook et al., 1989). The CP12 Hind III-Not I-1.7 kb promoter fragment was excised from pKS12P, filled in using Klenow fragment of DNA polymerase I and ligated into the Sma I site of the Agrobacterium Ti vector pTAK1 containing the *E. coli* uidA gene encoding β-glucuronidase (Jefferson et al., 1987), to produce a pTAKCP12 binary vector. In the same way CP25 Hind III-BamH I-3.7 kb and CP66 BamH I-1.9 kb promoter fragments were excised from pKS25P and pKS66P respectively, and ligated into pTAK1 cut with the same enzymes to produce pTAKCP25 and pTAKCP66 binary vectors. All constructs were transformed into *E. Coli* strain DH5α as an intermediate host for the vectors construction. The structure of the resultant chimeric reporter gene constructs was verified by PCR, restriction digest and sequence analysis. FIG. 23 shows a schematic of the constructs for plant transformation.

Plant Transformation

Plasmids pTAKCP12, pTAKCP25 and pTAKCP66 were transferred into *Agrobacteriun tumefaciens* LBA4404 using the freeze/thaw method described by Holsters et al. (1978). Tobacco (*Nicotiana tabacum* var. Samsun) transformants were produced by the leaf disc method (Bevan, 1984). Shoots were regenerated on medium containing 100 mg/l kanamycin and 200 mg/l carbenicillin. After rooting, plantlets were transferred to the glasshouse and grown under 16 h light/8 h dark conditions.

| Results | | | |
|---|---|---|---|
| | 12CP plants | 25CP plants | 66CP plants |
| # shoot taken | 440 | 250 | 404 |
| # shoot rooting | 130 (30%) | 82 (33%) | 120 (30%) |
| # shoot subdivided | 100 | 82 | 100 |
| # shoot re-rooting | 84 (84%) | 58 (70%) | 71 (71%) |

Primary Transformant Analysis

Objective

Primary transformants were first analysed by polymerase chain reaction (PCR) in order to reduce the number of plants to analyse and to make sure they contained the intact promoter-reporter gene cassette.

Since promoters can be deregulated in callus, GUS analysis were carried out on calli from transformation to make sure the promoters are not active at this stageas this might have had a deleterious effect on future transformations efficiency depending on the nature of the transgene (e.g. if barnase ribonuclease gene is driven by one of these promoters). Promoter activity was also assessed in young leaves from primary transformants to confirm the absence of ectopic expression at this stage.

Polymerase Chain Reaction

Genomic DNA for PCR analysis of transgenic plants was prepared according to Edwards et al. (1992). Plant extracts DNA (2.5 ul) was amplified [hot start at 80° C. ; (94° C., 1 min; 63° C., 1 min; 72° C., 1 min)×35 cycles; ( 72° C., 7 min)×1 cycle] using 2 U of Taq polymerase (Gibco BRL) in a 25 ul PCR reaction [200 uM dNTPs; 3 mM MgCl2; 1 uM oligos; 1×PCR buffer].

Results

A total of 37 individual transformants per class were randomly picked from in-vitro culture 12CP, 25CP and 66CP explants and analysed with 2 sets of primers. The first set contained one primer specific to the 5' end of the NOS terminator of the NPTII gene (NOSTER1) (SEQ ID NO: 33) and a reverse-primer specific to the 5'end of the cloned promoters (CYSGE12R (SEQ ID NO: 20), CYSGE25R (SEQ ID NO: 21) or CYSGE66R (SEQ ID NO: 22)). The second set contained one primer specific to the 3'-end of the promoters (CYSGE12C (SEQ ID NO: 23), CYSGE25C (SEQ ID NO: 25) or CYSGE66C (SEQ ID NO: 27)) and a reverse-primer specific to the 5' portion of the GUS gene (GUS1R (SEQ ID NO: 32)). A total of 34 explants was found to be double PCR positive for class 6 (94% of the plants tested), while for class 1 and class 2 only 27 plants gave the expected result (73% of the plants tested). Plants containing the intact cassette were transferred to the glass-house and self-pollinated.

| OLIGOS | SEQUENCE (5'→3') | SEQ ID NO: |
|---|---|---|
| CYSGE12RT | GGG TTC TTC TGG GTA GCA AAC TG | SEQ ID NO:29 |
| CYSGE25RT | ACT TCA CGT TCT GA TCT CAT CGA A | SEQ ID NO:30 |
| CYSGE66RT | GGG CCA GAA TGC GGA TTT TAC TAA | SEQ ID NO:31 |
| GUS1R | CGC TTT CCC ACC AAC GCT GAT C | SEQ ID NO:32 |
| NOSTER1 | TTG AAT CCT GTT GCC GGT CTT GC | SEQ ID NO:33 |

GUS Enzyme Assays

Fluorometric assays for GUS activity performed with the substrate 4-methylumbelliferyl-D-glucuronide (Sigma) were carried out using a Perkin-Elmer LS-35 fluorometer (Jefferson et al., 1987). Protein concentration of tissue homogenates were determined by the Bio-Rad protein assay (Bradford, 1976).

Results

GUS assays were carried out for each class on 20 regenerating calli resulting from the transformation process. Tobacco extracts from wild type leaves and callus as well as from leaves from 35S-GUS transgenic plants were used respectively as negative and positive controls. As shown in FIG. 24, no significant GUS activity could be detected in calli compared to the levels presents in leaves from the 35S-GUS plants.

FIG. 25 shows a preliminary assessment of the levels of GUS activity in young leaves from primary transformants of each class. Results indicate that the promoters are not active at this stage. This is a confirmation of the northern blot results obtained for class 2 and 6 but contradicts those for class 1 (FIG. 6). Class 1 CP showed some expression in leaves but it is thought to be due to a cross-hybridisation problem due to the nature of the probe. The GUS result seemed to confirm the latest hypothesis.

Analysis of Segregating Populations

Objective

The objective was to select for each class, four GUS expressing lines ranging from low expressors to high expressors, preferably from lines with a single locus insertion of the transgene as this facilitates the comparisons between lines. The number of loci in the primary transformants is estimated by the segregation of the NPTII (kanamycin-resistance) gene in the progeny.

Segregation Test

Seeds were sterilised in 10% bleach for 15 min. After several washes in sterile water around 150 seeds were sown on ½ MS medium (2.3 g/l MS salt, 1.5% sucrose, 0.8% Bactoagar, pH 5.9) containing 100 mg/l kanamycin. Seeds were grown for three weeks at 26° C. with 16 hours/8 hours light/dark prior to scoring. If the primary transformants contained one copy of the transgene, the expected ratio for $kan^R$ to $kan^S$ seeds was 3 to 1 (although in very rare cases one locus could possibly contain several transgenes).

Results

A substantial number of plants are showing a petaloïdie phenotype in which a variable proportion of the flowers in a plant have one or more normal stamens replaced by petals. Some of these plants were so badly affected that we could not recover any seeds.

The table below summarises the genetic data for the primary transformants.

|                       | 12CP plants | 25CP plants | 66CP plants |
|-----------------------|-------------|-------------|-------------|
| # lines in glasshouse | 27          | 27          | 34          |
| # lines giving seeds  | 22 (81%)    | 22 (81%)    | 29 (85%)    |
| # petaloidie phenotype| 13 (48%)    | 11 (41%)    | 5 (15%)     |
| # single loci inseriion| 11 (50%)   | 9 (41%)     | 12 (41%)    |

Preliminary Time Course Experiment

The northern blot results indicated an accumulation of CP mRNA in oil seed rape at 2 to 3 days after seeds imbibition (DAI). However, the heterologous expression in tobacco may differ from the endogenous expression in oil seed rape due to differences in physiology and transcription machinery. Furthermore, the activity of the promoter was indirectly analysed through a reporter protein, which delays the detection. So, in order to work out at which time point all the F1 generations should be analysed, the time course of GUS expression from each promoter had to be established.

Results

The experiment was carried out on 2 random lines per class as well as on wild type and 35S-GUS control lines. For each time point, 40 seeds of lines 12CP5, 12CP14, 25CP8, 25CP13, 66CP8 and 66CP76, as well as the controls, were grown at 26° C. with 16 hours/8 hours light/dark, on plates containing ½ MS media. Seedlings were sampled at 0, 2, 4, 6, 8, 10, 29 and 36 DAI and stored at −70° C. At time point 0 to 10 DAI, the 10 biggest seedlings were collected while only 5 were taken at 29 and 36 DAI which increased the variability within these samples.

In tobacco seedlings grown under the conditions described above, three lines out of 6 showed an induction of GUS expression during germination (FIG. 26). The activity peaked at around 30 DAI, although the protein accumulation clearly started at 8 DAI. Thus, the F1 generations should be assessed at 14 and 28 DAI to identify a range of GUS expressors. The maximum of activity was about 5% of 35S-GUS in the best expressing line (12CP5) although the relatively high level of expression in leaves suggests that this might be due to a position effect of the transgene. Normal levels of expression are more likely to be around 1% of 35S-GUS.

Identification of High GUS-expressing Lines During Germination

Results

Seedlings were grown on ½ MS media supplemented with 100 mg/l kanamycin in the conditions described previously. Five seedlings were harvested at 0 (dry seeds), 14 (2 expanded leaves) and 28 DAI (4 expanded leaves), pooled and assessed in duplicates as described previously.

FIGS. 27, 28, and 29 summarise the expression levels for class 1, 2 and 6 respectively. These preliminary data suggest that the promoters are expressed in a seedling-specific manner in tobacco. As expected from the RNA study in oilseed rape the levels of expression are low. Class 2 promoter fragment is more active than class 1 at this stage, while class 6 gives extremely low levels of expression.

GUS Histochemical Detection

GUS histochemical staining of whole seedlings was achieved by vacuum infiltration with a solution containing 1 mM X-gluc (5-bromo4-chloro-3-indolyl -D-glucuronide, 100 mM NaPO4 pH 7.5, 10 mM EDTA, 0.5 mM K3Fe(CN)6, 0.5 mM K4Fe(CN)6, 0.1% Titon X-100, 0.1% DMSO. After 12 h incubation at 37° C. intact seedling were photographed. Alternatively, stained seedlings were vacuum infiltrated with Tissue-Tek OCT compound prior to freezing in liquid nitrogen. A bright cryostat microtome (model 5030) was used to cut 20 μm sections at −23° C.

Other modifications of the present invention will be apparent to those skilled in the art without departing from the scope of the invention.

REFERENCES

Ascenzi P, Aducci P, Torroni A, Amiconi G, Ballio A, Menegatti E, Guarneri M: The pH dependence of pre-steady-state and steady-state kinetics for the papain-catalyzed hydrolysis of n-alpha carbobenzoxyglycine p-nitrophenyl ester. Biochem Biophys Acta 912 (2): 203–210 (1987).

Becker C, Fischer J, Nong V H, Munitz K: PCR cloning and expression analysis of cDNAs encoding cysteine proteinases from germinating seeds of Vicia sativa L. Plant Mol Biol 26: 1207–1212 (1994).

Bevan, M: Binary Agrobacterium vectors for plant transformation. Nucleic Acids Res 12, 8711–8721 (1984).

Boylan M T, Sussex I M: Purification of an endopeptidase involved with storage-protein degradation in Phaseolus vulgaris L. cotyledons. Planta 170 (3): 343–352 (1987).

Bradford M M: A rapid and sensitive method for the quantification of microgram quantities of protein utilising the principle of protein-dye binding. Anal Biochem 72: 248–254 (1976).

Cammue B P A, De Bolle M F C, Terras F R G, Proost P, Van Danme J, Rees S B, Vanderleyden J, Broekaert W F: Isolation and characterisation of a novel class of plant antimicrobial peptides from Mirabilis jalapa L. Seeds. JBC 267 (4): 2228–2233 (1992).

Cervantes E, Rodriguez A, Nicolas G: Ethylene regulates the expression of a cysteine proteinase gene during germination of chickpea (Cicer arietinum L.). Plant Mol Biol 25 (2): 207–215 (1994).

Cercos M, Mikkonen A, Ho T-H D: Promoter analysis of a GA-induced cysteine endoprotease gene in barley aleurone cells. Plant Physiol (Rockville) 108 (2 SUPPL.): 79 (1995).

Cohen L W, Coghlan V M, Dihel L C: Cloning and sequencing of papain-encoding cDNA. Gene 48: 219–227 (1986).

Comai L, Harada J J: Transcriptionnal activities in dry seed nuclei indicate the timing of the transition from embryogeny to germination. Proc Natl Acad Sci USA 87: 2671–2674 (1990).

deBarros E G, Larkins B A: Cloning of a cDNA encoding a putative cysteine protease from germinating maize seeds. Plant Science 99 (2): 189–197 (1994).

Dietrich R A, Maslyar D J. Heupel R C, Harada J J: Spatial patterns of gene expression in Brassica-napus seedlings: identification of a cortex-specific gene and localization of messenger RNA encoding isocitrate lyase and a polypeptide homologous to proteinases. Plant Cell 1 (1): 73–80 (1989).

Edwards K, Johnstone C, Thompson C: A simple and rapid method for the preparation of plant genomic DNA for PCR analysis. Nucleic Acids Res 19 (6): 1349 (1991).

Goetting-Minesky M P, Mullin B C: Differential gene expression in an actinorhizal symbiosis: Evidence for a nodule-specific cysteine proteinase. Proc Natl Acad Sci USA 91 (21): 9891–9895 (1994).

Goetting-Minesky P, Mullin B C: Evidence for a nodule-specific cysteine proteinase in an actinorhizal symbiosis. American Journal of Botany 81 (6 SUPPL.): 24 (1994).

Graham I A, Baker C J, Leaver C J: Analysis of the cucumber malate synthase gene promoter by transient expression and gel retardation assays. Plant Journal 6 (6): 893–902 (1994).

Grossberger: Minipreps of DNA from bacteriophage lambda. Nucleic Acids Res 15 (16): 6737 (1987).

Guerrero F D, Jones J T, Mullet J E: Turgor-responsive gene transcription and RNA levels increase rapidly when pea shoots are wilted sequence and expression of three inducible genes. Plant Mol Biol 15 (1): 11–26 (1990).

Hara-Nishimura I, Takeuchi Y, Nishimura M: Molecular characterization of a vacuolar processing enzyme related to a putative cysteine proteinase of Schistosoma mansoni. Plant Cell 5 (11): 1651–1659 (1993).

Hara-Nishhnura I, Shimada T, Hiraiwa N, Nishimura M: Vacuolar processing enzyme responsible for maturation of seed proteins. Journal of Plant Physiology 145 (5–6): 632–640 (1995).

Holsters M, de Waele D, Depicker A, Messen E, Van Montagu M, Schell J: Transfection and transformation of A. tumefaciens. Mol Gen Genet 163: 181–187 (1987).

Jefferson R A, Bevan M, Kavanagh T: The use of the Escherichia coli beta-glucuronidase gene as a gene fusion marker for studies of gene expression in higher plants— construction of promoter cloning vector plasmid pTAKI and detection of enzyme activity by fluorometric assay. Biochem Soc Trans 15: 17–18 (1987).

Jepson I, Bray J, Jenkins G, Schuch W, Edwards K: A rapid procedure for the construction of PCR cDNA libraries from small amounts of plant tissue. Plant Mol Biol Reporter 9 (2): 131–138 (1991).

Jiang B, Siregar U, Willeford K O, Luthe D S, Williams W P: Association of a 33-kilodalton cysteine proteinase found in corn callus with the inhibition of fall armyworm larval growth. Plant Physiol 108 (4): 1631–1640 (1995).

Jones M L, Larsen P B, Woodson W R: Ethylene-regulated expression of a carnation cysteine proteinase during flower petal senescence. Plant Mol Biol 28 (3): 505–512 (1995).

Karrer K M, Peiffer S L, DiTomas M E: Two distinct gene subfamilies within the family of cysteine protease genes. Proc Nad Acad Sci USA 90: 3063–3067 (1993).

Kianian S F, Quiros C F: Genetic analysis of major multigene families in Brassica oleracea and related species. Genome 35 (3): 516–527 (1992).

Koehler S M, Ho T-H D: Hormonal regulation processing and secretion of cysteine proteinases in barley aleurone layers. Plant Cell 2 (8): 769–784 (1990).

Korodi I; Asboth B; Polgar L: Disulfide bond formation between the active-site thiol and one of the several free thiol groups of chymopapain. Biochemistry 25 (22): 6895–6900 (1986).

Lidgett A, Moran M, Wong K A L Furze J, Rhodes M J C and Hamill J D: Isolation and expression pattern of a cDNA encoding a cathepsin B-like protease from Nicotiana rustica. Plant Mol Biol 29 (2): 379–384 (1995).

Lin E; Burns D J W; Gardner R C: Fruit developmental regulation of the kiwifruit actinidin promoter is conserved in transgenic petunia plants. Plant Mol Biol 23 (3): 489–499 (1993).

Linthorst H J M, Van Der Does C, Van Kan J A L, Bol J F: Nucleotide sequence of a cdna clone encoding tomato Lycopersicon esculentum cysteine proteinase. Plant Physiol 101 (2): 705–706 (1993).

Linthorst H J M, Van Der Does C, Brederode F T, Bol J F: Circadian expression and induction by wounding of tobacco genes for cysteine proteinase. Plant Mol Biol 21 (4): 685–694 (1993).

Mallinson D J, Lockwood B C, Coombs G H, North M J: Identification and molecular cloning of four cysteine proteinase genes from the pathogenic protozoon Trichomonas vaginalis. Microbiology 140 (10): 2725–2735 (1994).

Mikkelsen T R, Andersen B and Jorgensen R B: The risk of crop transgene spread. Nature 380: 31 (7 March 1996).

Marttila S, Porali I, Ho T-H D, Mikkonen A: Expression of the 30 kd cysteine endoprotease b in germinating barley seeds. Cell biol int 17 (2): 205–212 (1993).

Marttila S, Jones B L, Mikkonen A: Differential localization of two acid proteinases in germinating barley (Hordeum vulgare) seed. Physiologia Plantarum 93 (2): 317–327 (1995).

Mckee R A, Adams S, Matthews J A, Smith C J, Smith H: Molecular cloning of two cysteine proteinases from pawpaw (carica-papaya). Biochem J 237 (1): 105–1101 (1986).

Minami A and Fukuda H: Transient and specific expression of a cysteine endopeptidase associated with autolysis during differentiation of Zinnia mesophyll cells into tracheary elements. Plant Cell Physiol 36 (8): 1599–1606 (1995).

Mino M, Inoue M: Hybrid vigor in relation to lipid and protein metabolism in germinating maize kernels. Jpn J Breed 38 (4): 428–436 (1988).

Nong V H, Becker C, Muentz K: cDNA cloning for a putative cysteine proteinase from developing seeds of soybean. Biochim et Biophys Acta 1261 (3): 435–438 (1995).

Okayama H, Kawaichi M, Brownstein M, Lee F, Yokota T, Arai K: High-efficiency cloning of full-length cDNA: construction and screening of cDNA expression libraries from mammalian cells. Meth. in Enzymology 154: 3–27 (1987).

Pautot V, Brzezinski R, Tepfer M: Expression of a mouse metallothionein gene in transgenic plant tissues. Gene 77:133–140 (1989).

Pladys D, Vance C P: Proteolysis during development and senescence of effective and plant gene-controlled ineffective alfalfa nodules. Plant Physiol 103 (2): 379–384 (1993).

Praekelt U M, Mckee R A, Smith H: Molecular analysis of actinidin the cysteine proteinase of Actinidia chinensis. Plant Mol Biol 10 (3): 193–202 (1988).

Revell d f, Cummings N J, Baker K C, Collins M E, Taylor M A J, Sumner I G, Pickersgill R W, Connerton I F, Goodenough P W: Nucleotide sequences and expression in Escherichia coli of cDNA encoding papaya proteinase omega from Carica papaya. Gene 127 (2): 221–225 (1993).

Sambrook J, Fritsch E F, Maniatis T: Molecular cloning, a laboratory manual. Cold Spring Harbor Laboratory, Cold Spring Harbor, N.Y. (1989).

Sanger F, Milkin S, Coulson A R: DNA sequencing with chain-terminating inhibitors. Proc Natl Acad Sci USA 74: 5463–5467 (1977).

Schaffer M A, Fischer R L: Analysis of mRNAs that accumulate in response to low temperatures identifies a thiol protease gene in tomato. Plant Physiol 87: 431–436 (1988).

Shimada T, Hiraiwa N, Nishimura M, Hara-Nishimura I: Vacuolar processing enzyme of soybean that converts proproteins to the corresponding mature forms. Plant Cell Physiol 35 (4): 713–718 (1994).

Shintani A, Yamauchi D, Minamikawa T: Nucleotide sequence of cDNA for a putative cysteine protease from rice seeds. Plant Physiol 107 (3): 1025 (1995).

Shutov A D, Vaintraub I A: Degradation of storage proteins in germinating seeds. Phytochemistry 26 (6): 1557–1566 (1987).

Smart C M, Hosken S E, Thomas H, Greaves J A, Blair B G, Schuch W: The timing of maize leaf senescence and characterisation of senescence-related cDNAs. Physiol Plant 93 (4): 673–682(1995).

Takeda O, MIura Y, Mitta M, Matsushita H, Kato I, Abe Y, Yokosawa H Ishii S-I: Isolation and analysis of cDNA encoding a precursor of *Canavalia ensiformis* asparaginyl endopeptidase (Legumain). Journal of Biochemistry 16 (3): 541–546 (1994).

Taylor M A J, Baker K C, Briggs G S, Connerton I F, Cumnings N J, Pratt K A, Revell D F, Freedman R B, Goodenough P W: Recombinant pro-regions from papain and papaya proteinase IV are selective high affinity inhibitors of the mature papaya enzymes. Protein Engineering 8 (1): 59–62 (1995).

Terras R G, Torrekens S, Van Leuven F, Osborn R W, Vanderleyden J, Cammue B P A, Broekaert W F: A new family of basic cysteine-rich plant antifungal proteins from Brassicaceae species. FEBS Lett 316 (3): 233–240 (1993).

Thomas M P, Topham C M, Kowlessur D, Mellor G W, Thomas E W, Whitford D, Brocklehurst K: Structure of chymopapain M the late-eluted chymopapain deduced by comparative modelling techniques and active-centre characteristics determined by pH-dependent kinetics of catalysis and reactions with time-dependent inhibitors: The Cys-25-His-159 ion-pair is insufficient for catalytic competence in both chymopapain M and papain. Biochemical Journal 300 (3): 805–820 (1994).

Valpuesta V, Lange N E, Guerrero C, Reid M S: Up-regulation of a cysteine protease accompanies the ethylene-insensitive senescence of daylily (Hemerocallis) flowers. Plant Mol Biol 28 (3): 575–582 (1995).

Vernet T, Berti P J, De Montigny C, Musil R, Tessier D C, Menard R, Magny M-C, Storer A C, Thomas D Y: Processing of the papain precursor: the ionization state of a conserved amino acid motif within the Pro region participates in the regulation of intramolecular processing. J Biol Chem 270 (18): 10838–10846 (1995).

Watanabe H, Abe K, Emori Y, Hosoyama H, Arai S: Molecular cloning and gibberellin-induced expression of multiple cysteine proteinases of rice seeds (oryzains). J Biol Chem 266 (25): 16897–16902(1991).

Wiederanders B, Broemme D, Kirschke H, Von Figura K, Schmidt B, Peters C: Phylogenetic conservation of cysteine proteinases cloning and expression of a cDNA coding for human cathepsins. J Biol Chem 267 (19): 13708–13713 (1992).

Yamauchi D, Akasofu H, Minamikawa T: Cysteine endopeptidase from *Vigna mungo*: gene structure and expression. Plant Cell Physiol. 33 (6): 789–797 (1992).

---

What is claimed is:

1. An isolated promoter comprising the DNA sequence of an oil seed rape cysteine protease gene promoter wherein said DNA sequence is selected from the group consisting of SEQ ID NO:71, SEQ ID NO:72 and SEQ ID NO:73, or a part of SEQ ID NO: 71, SEQ ID NO: 72 or SEQ ID NO: 73 which is sufficient to control expression of a gene of interest; or a nucleotide sequence which will hybridize to any of these under high stringency hybridization conditions and which controls expression of a gene of interest.

2. A recombinant DNA construct comprising the promoter of claim 1 operably linked to a gene of interest.

3. An expression system comprising a construct according to claim 2.

4. Plant germ plasm comprising a recombinant DNA construct of claim 2.

5. An expression system for the tissue or tissues of a plant material, the expression systemn comprising a gene of interest fused to a gene promoter as defined in claim 1, wherein the expression system is capable of being expressed in the tissue or tissues of the plant material.

6. An expression system according to claim 5 wherein the expression system is capable of being expressed in the tissue of a germinating seedling or developing grain or plant.

7. An expression system according to claim 6 wherein the expression system is integrated within a germinating seedling's genomic DNA or a developing grain's genomic DNA or a plant's genomic DNA.

8. An expression system according to claim 7 which is stably integrated within a germinating seedling's genomic DNA or a developing grain's genomic DNA or a plant's genomic DNA.

9. A recombinant DNA construct functional in a plant comprising
   (i) a first promoter according to claim 1,
   (ii) a sequence encoding a disrupter product capable of disrupting cell function, said sequence being under the control of said promoter;
   (iii) a second promoter which is inducible by the external application of a chemical, and
   (iv) a control sequence which is fmctionally liiked to said sequence encoding a disrupter product and which is under the control of said second promoter.

10. A recombinant DNA construct according to claim 9 wherein said control sequence comprises a repressor protein gene and wherein an operator sequence which is recognized by the repressor protein is provided, such that in the presence of the inducer the repressor protein is produced which interacts with the operator sequence thereby disabling the first producer and inhibiting expression of the sequence encoding the disrupter product.

11. A recombinant DNA construct according to claim 10 wherein the repressor protein gene encodes a bacterial repressor.

12. A recombinant DNA construct according to claim 11 wherein the repressor protein gene encodes the lac repressor or a repressor used by 434, P22 or lambda-bacteriophages.

13. A recombinant DNA construct according to claim 10 wherein the operator sequence comprises a "pseudo-operator".

14. A recombinant DNA construct according to claim 9 wherein the sequence encoding the disrupter product is a nucleotide sequence, which is in sense orientation to all or part of an endogenous plant gene that is essential to plant development or a gene conferring a desired characteristic on the plant.

15. A recombinant DNA construct according to claim 14 wherein the endogenous plant gene is essential to seed germination or early seedling development.

16. A recombinant DNA construct according to claim 9 wherein the sequence encoding the disrupter product is a nucleotide sequence, which is in antisense orientation to an endogenous plant gene that is essential to plant development or a gene conferring a desired characteristic on the plant.

17. A recombinant DNA construct according to claim 16 wherein the endogenous plant gene is essential to seed germination or early seedling development.

18. A recombinant DNA construct according to claim 9 wherein the second promoter is a chemically inducible gene promoter sequence from the glutathione S-transferase system, the Alc system or the ecdysone system.

19. A recombinant DNA construct according to claim 9 wherein the disrupter product is the product of a cytotoxic gene.

20. A recombinant DNA construct according to claim 9 wherein the said disrupter product is a recombinase or transposase adapted to excise a nucleotide sequence flanked by recombinase recognition sequences.

21. A recombinant DNA construct according to claim 9 wherein the construct is capable of being expressed in the tissue or tissues of a germinating seedling or a developing grain or a plant when the construct is integrated within the grain's or seedling's or plant's genomic DNA.

22. A recombinant DNA construct according to claim 21 wherein the construct is capable of being expressed in the tissue or tissues of a germinating seedling or a developing grain or a plant when the construct is within the grain's or seedling's or plant's genomic DNA.

23. A plant or seed which is incapable of growing to maturity comprising a recombinant DNA construct of claim 9.

24. The recombinant DNA construct of claim 9 wherein said first promoter is selected from the group consisting of SEQ ID NO: 71, SEQ ID NO: 72 or SEQ ID NO: 73 or a part of SEQ ID NO: 71, SEQ ID NO: 72 or SEQ ID NO: 73 which is sufficient to control expression of a gene of interest.

25. The recombinant DNA construct of claim 24 wherein said first promoter is selected from the group consisting of SEQ ID NO: 71, SEQ ID NO; 72 and SEQ ID NO: 73.

26. An isolated promoter comprising SEQ ID NO:71 or a part thereof which is sufficient to control expression of a gene of interest; or a nucleotide sequence which will hybridize to any of these under high stringency hybridization conditions and which controls expression of a gene of interest.

27. A promoter according to claim 26 which comprises SEQ ID NO:71 or a part thereof which is sufficient to control expression of a gene of interest.

28. A recombinant DNA construct comprising the promoter of claim 25 operably linked to a gene of interest.

29. Plant germplasm comprising a rembinant DNA construct of claim 28.

30. An expression system for the tissue or tissues of a plant material, the expression system compnsing a gene of interest fuised to a gene promoter as defined in claim 25. wherein the expression system is capable of being expressed in the tissue or tissues of the plant material.

31. An isolated promoter comprising SEQ ID NO:72 or a part thereof which is sufficient to control expression of a gene of interest; or a nucleotide sequence which will hybridize to any of these under high stringency hybridization conditions and which controls expression of a gene of interest.

32. A promoter according to claim 31 which comprises SEQ ID NO:72 or a part thereof which is sufficient to control expression of a gene of interest.

33. A recombinant DNA construct according to claim 32 wherein the construct is capable of being expressed in the tissue or tissues of a germinating seedling or a developing grain or a plant when the construct is integrated within the grain's or seedling's or plant's genomic DNA.

34. An expression system comprising a construct according to claim 32.

35. Plant germplasm comprising a recombinant DNA construct of claim 32.

36. An isolated promoter which comprises SEQ ID NO:72 or a part thereof which is sufficient to control expression of a gene of interest.

37. An expression system for the tissue or tissues of a plant material, the expression system comprising a gene of interest fused to a gene promoter as defined in claim 36, wherein the expression system is capable of being expressed in the tissue or tissues of the plant material.

38. An isolated promoter comprising SEQ ID NO:73 or a pat thereof which is sufficient to control expression of a gene of interest; or a nucleotide sequence which will hybridize to any of these under high stringency hybridization conditions and which controls expression of a gene of interest.

39. A promoter according to claim 38 which comprises SEQ ID NO, 73 or a part thereof which is sufficient to control expression of a gene of interest.

40. A recombinant DNA construct comprising the promoter of claim 38 operably linked to a gene of interest.

41. Plant germplasm comprsing a recombinant DNA construct of claim 40.

42. An expression system for the tissue or tissues of a plant material the expression system compnsimg a gene of interest fused to a gene promoter as defined in claim 38, wherein the expression system is capable of being expressed in the tissue or tissues of the plant material.

43. A recombinant plant genome comprising a foreign sequence selected from the group consisting of:
  (a) a promoter comprising a DNA sequence selected from the group consisting of SEQ ID NO:71, SEQ ID NO:72 and SEQ ID NO:73 or a part of SEQ ID NO:71, SEQ ID NO:72 or SEQ ID NO:73 which is sufficient to control expression of a gene of interest; or a nucleotide sequence which will hybridize to any of these umder high stringency hybridization conditions and which controls expression of a gene of interest;
  (b) a DNA sequence encoding a protein of SEQ ID NO: 65, SEQ ID NO: 66, SEQ ID NO:67, SEQ ID NO:68 SEQ ID NO:69 or SEQ ID NO: 70;
  (c) a recombinant DNA construct comprising a gene of interest operably linked to a promoter comprising a DNA segquece selected from the group consisting of SEQ ID NO:71, SEQ ID NO:72 and SEQ ID NO:73 or a part of SEQ ID NO:71, SEQ ID NO:72 or SEQ ID NO:3 which is sufficient to control expression of a gene of interest; or a nucleotide sequence which will hybridize to any of these under high stringency hybridization conditions and which controls expression of a gene of interest;
  (d) an expression system comprising a gene of interest fuised to a promoter comprising a DNA seauence selected from the group consisting of SEQ ID NO: 71, SEQ ID NO:72 and SEQ ID NO:73 or a part of SEQ ID NO:72 or SEQ ID NO:74 which is sufficient to control expression of a gene of interest; or a nucleotide sequence which will hybridize to any of these under high stringency hybridization conditions and which controls expression of a gene or interest.

44. A plant, plant seed, or plant cell comprising the recombinant plant genome of claim 43.

45. The recombinant plant genome of claim 43 wherein said promoter comprises a DNA sequence selected from the group consisting of SEQ ID NO: 71, SEQ ID NO: 72 and SEQ ID NO: 73 or part of SEQ ID NO: 71, SEQ ID NO: 72 or SEQ ID NO: 73 which is sufficicnt to control expression of a gene of interest.

46. The recombinant plant genome of claim 43 wherein said promoter is selected from the group consisting of SEQ ID NO: 71, SEQ ID NO: 72 and SEQ ID NO: 73.

47. The recombinant plant genome of claim 43 wherein said DNA construct comnprises a gene of interest operably linked to a promoter comprising a DNA sequence selected from the group consisting of SEQ ID NO: 71, SEQ ID NO: 72 and SEQ ID NO: or part of SEQ ID NO: 71, SEQ ID NO: 72 or SEQ ID NO: 73 which is sufficient to control expression of a gene of interest.

48. The recombinant plant genome of clam 47 wherein said promoter is selected from the group consisting of SEQ ID NO: 71, SEQ ID NO: 72 or SEQ ID NO: 73.

49. The recombinant plant genome of claim 43 wherein said expression system comprises a gene of interest fuised to a promoter comprising a DNA sequence selected from the group consisting of SEQ ID NO: 71, SEQ ID NO: 72 and SEQ ID NO: 73 or part, of SEQ ID NO: 71, SEQ ID NO: 72 or SEQ ID NO: 73 which is sufficient to control expression of a gene of interest.

50. The recombinant plant genome of claim 49 wherein said promoter is selected from the group consisting of SEQ ID NO: 71, SEQ ID NO: 72 and SEQ ID NO: 73.

51. An isolated DNA sequence encoding the protein shown in SEQ ID NO: 65.

52. The DNA sequence of claim 51 wherein said DNA sequence is SEQ ID NO: 59.

53. A recombinant DNA construct finctional in a plant compnsing the DNA sequence of claim 51 operably linked to a promoter.

54. An isolated DNA sequence encoding the protein shown in SEQ ID NO: 66.

55. The sequence DNA of claim 54 wherein said DNA sequence is SEQ ID NO: 60.

56. A reconbinant DNA construct fimctional in a plant comprising the DNA sequence of claim 54 operably linked to a promoter.

57. An isolated DNA sequence encoding the protein shown in SEQ ID NO:67.

58. The DNA sequence of claim 57 wherein said DNA sequence is SEQ ID NO:61.

59. A recombinant DNA construct functional in a plant comprising the DNA sequence of claim 57 operably linked to a promoter.

60. An isolated DNA sequence encoding the protein shown in SEQ ID NO:68.

61. The sequence DNA of claim 60 wherein said DNA sequence is SEQ ID NO:62.

62. A recombinant DNA construct finctional in a plant comprising the DNA sequence of claim 60 operably linked to a promoter.

63. An isolated DNA sequence encoding the protein shown in SEQ ID NO:69.

64. The DNA sequence of claim 63 wherein said DNA sequence is SEQ ID NO:63.

65. A recombinant DNA construct functional in a plant comprising the DNA sequence of claim 63 operably linked to a promoter.

66. An isolated DNA sequence encoding the protein shown in SEQ ID NO: 70.

67. The DNA sequence of claim 66 wherein said DNA sequence is SEQ ID NO: 64.

68. A recombinant DNA construct functional in a plant comprising the DNA sequence of claim 65 operably linked to a promoter.

* * * * *

SEQUENCE LISTING

<160> NUMBER OF SEQ ID NOS: 89

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence: Oligo

<400> SEQUENCE: 1
ggccacgcgt cgactagtta ctcgagtttt ttttttttt ttt                     43

<210> SEQ ID NO 2
<211> LENGTH: 21
<212> TYPE: DNA
<213> ORGANISM: Artificial Sequence
<220> FEATURE:
<221> NAME/KEY: misc_feature
<222> LOCATION: (3, 12, 15, 18)
<223> OTHER INFORMATION: n = i
<220> FEATURE:
<223> OTHER INFORMATION: Description of Artificial Sequence: Oligo

<400> SEQUENCE: 2
ggntgyaayg gnggnytnat g                                            21

<210> SEQ ID NO 3
<211> LENGTH: 23
<212> TYPE: DNA
<213> ORGANISM: Artificial Sequence
<220> FEATURE:
<221> NAME/KEY: misc_feature
<222> LOCATION: (3, 12, 15, 18)
<223> OTHER INFORMATION: n = i
<220> FEATURE:
<223> OTHER INFORMATION: Description of Artificial Sequence: Oligo

<400> SEQUENCE: 3
ggntgyaayg gnggnytnat gra                                           23

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Oligo

<400> SEQUENCE: 4
tatccttatc aagaacgtga tggca                                         25

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Oligo

<400> SEQUENCE: 5
cctacgatga gcactgcgtg gt                                            22

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Oligo

<400> SEQUENCE: 6
gcagtaatca aattgggatt gttataa                                       27

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Oligo

<400> SEQUENCE: 7
cgtggaacca gcagtgtttg aagtt                                         25

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence: Oligo

<400> SEQUENCE: 8
gagagagaga gagagagaga actagtctcg agtcccatgg tttttaat                48

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence: Oligo

<400> SEQUENCE: 9
gagagagaga gagagagaga actagtctcg agccgccgtt tttcat                  46

<210> SEQ ID NO 10

```
<211> LENGTH: 28
<212> TYPE: DNA
<213> ORGANISM: Artificial Sequence
<220> FEATURE:
<223> OTHER INFORMATION: Description of Artificial Sequence: Oligo

<400> SEQUENCE: 10
cccatggttt ttaatgacaa attgaaaa                                          28

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Oligo

<400> SEQUENCE: 11
ccgccgtttt tcattatgaa ttgaaa                                            26

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Oligo

<400> SEQUENCE: 12
cgccgttttt catgatgaat tgaaaa                                            26

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Oligo

<400> SEQUENCE: 13
tagaaaacca acaaaacaaa catacaat                                          28

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Oligo

<400> SEQUENCE: 14
gaacaaccaa gccaaacata caatat                                            26

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Oligo

<400> SEQUENCE: 15
atcgtcttct tcctttgttt ctctca                                            26

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Oligo

<400> SEQUENCE: 16
```

```
cttcgtcagc gaaactcctc tctt                                              24

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Oligo

<400> SEQUENCE: 17
cagaactaga acaaccaagc caaac                                             25

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Oligo

<400> SEQUENCE: 18
gaagaaacta gaagaaggga gaagaa                                            26

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Oligo

<400> SEQUENCE: 19
tcacttcttc atcggttctc ca                                                22

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Oligo

<400> SEQUENCE: 20
aggaagaaga cgatgatggt gaca                                              24

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Oligo

<400> SEQUENCE: 21
gtacaagaga agtaaagaga ggagt                                             25

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Oligo

<400> SEQUENCE: 22
cgtataggag aagtaaagaa atgagt                                            26

<210> SEQ ID NO 23
<211> LENGTH: 22
<212> TYPE: DNA
```

```
<213> ORGANISM: Artificial Sequence
<220> FEATURE:
<223> OTHER INFORMATION: Description of Artificial Sequence: Oligo

<400> SEQUENCE: 23
gtaatggcct agcctgtctg gc                                              22

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Oligo

<400> SEQUENCE: 24
gatgatggtg acaagctttt tcttacagg                                       29

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Oligo

<400> SEQUENCE: 25
ctatcttgca tgcccattat tactttt                                         26

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Oligo

<400> SEQUENCE: 26
acgaagccgg atcctatgtt tgttttgttg                                      30

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Oligo

<400> SEQUENCE: 27
catcttgcat gcccattact gcat                                            24

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Oligo

<400> SEQUENCE: 28
aggaagccgg atcctatgtt tggcttgg                                        28

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Oligo

<400> SEQUENCE: 29
gggttcttct gggtagcaaa ctg                                             23
```

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Oligo

<400> SEQUENCE: 30
acttcacgtt ctgaatctca tcgaa                                          25

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Oligo

<400> SEQUENCE: 31
gggccagaat gcggatttta ctaa                                           24

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Oligo

<400> SEQUENCE: 32
cgctttccca ccaacgctga tc                                             22

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Oligo

<400> SEQUENCE: 33
ttgaatcctg ttgccggtct tgc                                            23

<210> SEQ ID NO 34
<211> LENGTH: 317
<212> TYPE: DNA
<213> ORGANISM: Brassica napus
<220> FEATURE:
<221> NAME/KEY: misc_feature
<222> LOCATION: (1)..(5), 10, 15, 16, 25..29, 197
<223> OTHER INFORMATION: n is unknown

<400> SEQUENCE: 34
nnnnncaatn ggggnntgat ggacnnnnnt tttcaatttg tcattaaaaa ccatgggatt     60
gacacagaga aagattatcc ttatcaagaa cgtgatggca cctgtaagaa agataagttg    120
aatagaaagg ttgtgacaat tgatagctac gctggtgtaa aatcaaatga cgagaaagcg    180
ttactagaag ctgtagncgc tcagccagtt agtgttggta tctgtgggag cgagagagcg    240
tttcagttat actctaaggg aatattctct ggcccatgtt caacatcatt ggaccacgca    300
gtgctcatcg taggata                                                  317

<210> SEQ ID NO 35
<211> LENGTH: 361
<212> TYPE: DNA
<213> ORGANISM: Brassica napus
<220> FEATURE:

```
<221> NAME/KEY: misc_feature
<222> LOCATION: (1)..(28)
<223> OTHER INFORMATION: n is unknown

<400> SEQUENCE: 35
nnnnnnnnnn nnnnnnnnnn nnnnnnnnct tttcaattca tcatgaaaaa cggcggtttg      60
aacaccgagc aagattatcc ttaccgtggt tccaatggaa aatgcaattc tttactgaat     120
tcaagagttg taactattga tggttacgaa gatgttccta ctgaagatga aacggcgttg     180
aagagagcag tttcatacca gcccgtgagt gttgccattg aagctggtgg aagagttttc     240
caacattacc aatcggggat cttcactggg aagtgtggga caaatctaga tcatgcagtg     300
gtggctgttg gttatggttc agagaacggt attgactatt ggattgtaag gaactcgtgg     360
g                                                                    361

<210> SEQ ID NO 36
<211> LENGTH: 468
<212> TYPE: DNA
<213> ORGANISM: Brassica napus
<220> FEATURE:
<221> NAME/KEY: misc_feature
<222> LOCATION: (1)..(29), 439, 441
<223> OTHER INFORMATION: n is unknown

<400> SEQUENCE: 36
nnnnnnnnnn nnnnnnnnnn nnnnnnnnnt tttcaattca taatgaaaaa cggcggatta      60
aacaccgaga aagactaccc ttaccacgga accaatggca aatgcaactc tttacttaag     120
aattcaagag ttgtaactat cgatggatac gaagatgttc ctagtaaaga tgaaaccgcg     180
ttgaagagag cagtttcata ccagcctgtg agtgttgcta ttgatgctgg tggaagagct     240
ttccaacatt accaatctgg aatcttcact ggaaagtgtg gtacgaatat ggatcacgct     300
gtggtggcgg ttggttatgg tcagagaaac ggcgttgact attggattgt acgtaactct     360
tggggtacac gttggggaga ggatggttac attaggatgg agagaaacgt ggcgtctaaa     420
tccggtaagt gtgggattnc natagaagcc tcgtatccgg ttaagtac                  468

<210> SEQ ID NO 37
<211> LENGTH: 743
<212> TYPE: DNA
<213> ORGANISM: Brassica napus
<220> FEATURE:
<223> OTHER INFORMATION: Full sequence provided ie coding and non-coding
      sequences in Figures 3A and 3B
<220> FEATURE:
<221> NAME/KEY: misc_feature
<222> LOCATION: (1)..(5), 10, 12..15, 28, 411, 412
<223> OTHER INFORMATION: n is unknown

<400> SEQUENCE: 37
nnnnncaacn gnnnnctgat ggattatnct tttcaattca taatgaaaaa cggcggatta      60
aacaccgaga aagactatcc ttaccacgga accaatggca aatgcaactc tttacttaaa     120
aattcgagag ttgtgactat cgatggatac gaagatgttc ctagtaaaga tgaaaccgcg     180
ttgaagagag cagtttcgta ccagcctgtg agtgttgcta ttgatgctgg tggaagagct     240
ttccaacatt accaatctgg aatcttcact ggaaagtgtg gtacgactat ggatcacgct     300
gttgtggcgg ttggttatgg atcagagaac ggtgttgact attggattgt acgtaactct     360
tggggtacac gttggggaga ggatggttac attaggatgg agagaaacgt nncgtctaaa     420
tccggtaagt gtgggattgc gatagaagcc tcgtatccgg ttaagtacag cccaaacccg     480
```

-continued

```
gttcgtggga ccagcagtgt ttgaaggtaa caaaaagcat ctcatgcagt aatcaaattg    540
ggattgttat aagttaaatt aatcttgtat tattgtttgt atgtatagta tttcgaaaaa    600
aaatgattca ccatagggat ttaatctgta taaatctcta ggttggtcaa atatcatttc    660
attcaaagaa tatttgcttt gacttgatta tgtattaaga gaaatataat aaaatggtat    720
atttctcaac agcaaaaaaa aaa                                            743
```

<210> SEQ ID NO 38
<211> LENGTH: 743
<212> TYPE: DNA
<213> ORGANISM: Brassica napus
<220> FEATURE:
<223> OTHER INFORMATION: Full sequence provided ie coding and non-coding
      sequences in Figures 3A and 3B
<220> FEATURE:
<221> NAME/KEY: misc_feature
<222> LOCATION: 13, 178, 180, 217, 226, 236..238
<223> OTHER INFORMATION: n is unknown

<400> SEQUENCE: 38

```
gggtgcaacg ggngactgat ggactatgct tttcaattca tcatgaaaaa cggcggtttg     60
aacaccgagc aagattatcc ttaccgtggt tccaatggaa aatgcaattc tttactgaag    120
aattcaagag ttgtaactat tgatggatac gaagatgttc ctagtaaaga tgaaaccncn    180
ttgaagagag cagtttcata ccagcctgtg agtgttncta ttgatnctgg tggaannnct    240
ttccaacatt accaatctgg aatcttcact ggaaagtgtg gtacgaatat ggatcacgct    300
gtggtggcgg ttggttatgg gtcagagaac ggcgttgact attggattgt acgtaactct    360
tggggtacac tttggggaga ggatggttac attaggatgg agagaaacgt ggcgtctaaa    420
tccggtaagt gtgggattgc gatagaagcc tcgtatccgg ttaagtacag cccaaacccg    480
gttcgtnnga ccagcagtgt ttgaaggtaa caaaaagaat ctcatgcagt aatcaaattg    540
ggattgttat aagttaaatt aatcttgtat tattgtttgt atgtatggta tttcgaaaaa    600
aattgattca ccatagggat ttaatctgta taaatctcta tgttggtcaa tatcatttca    660
ttcaaagaat atttgctttg cttgattat gtattaagag aaatataata aaatgatat     720 atttctcagc agcaaaaaaa aaa                                            743
```

<210> SEQ ID NO 39
<211> LENGTH: 744
<212> TYPE: DNA
<213> ORGANISM: Brassica napus
<220> FEATURE:
<223> OTHER INFORMATION: Full sequence provided ie coding and non-coding
      sequences in Figures 3A and 3B
<220> FEATURE:
<221> NAME/KEY: misc_feature
<222> LOCATION: 427, 442, 444, 448, 451, 452, 460
<223> OTHER INFORMATION: n is unknown

<400> SEQUENCE: 39

```
gggtgcaacg gggggttgat ggactatgct tttcaattca tcatgaaaaa cggcggtttg     60
aacaccgagc aagattatcc ttaccgtggt tccaatggaa aatgcaattc tttactgaag    120
aattcaagag ttgtaactat tgatggatac gaagatgttc ctactgaaga tgaaacggcg    180
ttgaagagag cagtttcata ccagcccgtg agtgttgcca ttgaagctgg tggaagagtt    240
ttccaacatt accaatcggg gatcttcact gggaagtgtg ggacaaatct agatcatgca    300
gtggtggctg ttggttatgg ttcagagaac ggtattgact attggattgt aaggaactcg    360
tggggtacac gttggggaga ggatggttac attagaatgg agagaaactt ggcaaggtcc    420
```

```
aagtccngca agtgtggaat tncngttnaa nnctcgtacn cggttaagta cagtccaaac    480
ccggttcgtg gaaccagcag tgtttgaagt ttttttaaaa taaaactcaa taatcacttg    540
ggagttttat aactaagatt taatctcata ttattgtttg tatgtatagt atatcaaaaa    600
agaaggtatt tgatccacca tacggattta atctgtatgg atccttatgt cgatcaatat    660
catttcgttt aaagaaagat taatttggtt gtttatgtat taagagaagt ataataaaat    720
gatatatttc tcttaaaaaa aaaa                                            744

<210> SEQ ID NO 40
<211> LENGTH: 750
<212> TYPE: DNA
<213> ORGANISM: Brassica napus
<220> FEATURE:
<223> OTHER INFORMATION: Full sequence provided ie coding and non-coding
      sequences in Figures 3A and 3B
<220> FEATURE:
<221> NAME/KEY: misc_feature
<222> LOCATION: (175)..(238), 243, 248, 257, 425, 427, 434, 436, 444,
      484, 548
<223> OTHER INFORMATION: n is unknown

<400> SEQUENCE: 40
gggtgcaacg gggggttgat ggactatgct tttcaattca tcatgaaaaa cggcggtttg    60
aacaccgagc aagattatcc ttaccgtggt tccaatggaa aatgcaattc tttactgaag    120
aattcaagag ttgtaactat tgatggttac gaagatgttc ctactgaaga tgaannnnnn    180
nnnnnnnnnn nnnnnnnnnn nnnnnnnnnn nnnnnnnnnn nnnnnnnnnn nnnnnnnntt    240
ttncaacntt accaatnggg gatcttcact gggaagtgtg ggacaaatct agatcatgca    300
gtggtggctg ttggttatgg ttcagagaac ggtattgact attggattgt aaggaactcg    360
tggggtacac gttggggaga ggatggttac attagaatgg agagaaactt ggcaaggtcc    420
aagtncngca agtntngaat tgcngttgaa gcctcgtacc cggttaagta cagtccaaac    480
ccgnttcgtg gaaccagcag tgtttgaagt tcttttaaaa taaaactcaa taatcacttg    540
ggagtttnat aactaagatt taatctcata ttattgtttg tatgtatagt atatcaaaaa    600
agaaggtatt tgatccacca tacggattta atctgtatgg atccttatgt cgatcaatat    660
catttcgttt aaagaaagat taatttggtt gtttatgtat taagagaagt ataataaaat    720
gatatatttc tcttaacctc aaaaaaaaaa                                      750

<210> SEQ ID NO 41
<211> LENGTH: 317
<212> TYPE: DNA
<213> ORGANISM: Brassica napus
<220> FEATURE:
<221> NAME/KEY: misc_feature
<222> LOCATION: (1)..(6), 10, 15, 16, 25..29
<223> OTHER INFORMATION: n is unknown

<400> SEQUENCE: 41
nnnnncaatn ggggnntgat ggacnnnnnt tttcaatttg tcattaaaaa ccatgggatt    60
gacacagaga aagattatcc ttatcaagaa cgtgatggca cctgtaagaa agataagttg    120
aatagaaagg ttgtgacaat tgatagctac gctggtgtaa aatcaaatga cgagaaagcg    180
ttactagaag ctgtagncgc tcagccagtt agtgttggta tctgtgggag cgagagagcg    240
tttcagttat actctaaggg aatattctct ggcccatgtt caacatcatt ggaccacgca    300
gtgctcatcg taggata                                                   317
```

-continued

```
<210> SEQ ID NO 42
<211> LENGTH: 156
<212> TYPE: PRT
<213> ORGANISM: Brassica napus
<220> FEATURE:
<221> NAME/KEY: SITE
<222> LOCATION: (1)..(10), 147
<223> OTHER INFORMATION: Xaa is unknown

<400> SEQUENCE: 42

Xaa Xaa Xaa Xaa Xaa Xaa Xaa Xaa Xaa Xaa Phe Gln Phe Ile Met Lys
  1               5                  10                  15

Asn Gly Gly Leu Asn Thr Glu Lys Asp Tyr Pro Tyr His Gly Thr Asn
             20                  25                  30

Gly Lys Cys Asn Ser Leu Leu Lys Asn Ser Arg Val Val Thr Ile Asp
         35                  40                  45

Gly Tyr Glu Asp Val Pro Ser Lys Asp Glu Thr Ala Leu Lys Arg Ala
     50                  55                  60

Val Ser Tyr Gln Pro Val Ser Val Ala Ile Asp Ala Gly Gly Arg Ala
 65                  70                  75                  80

Phe Gln His Tyr Gln Ser Gly Ile Phe Thr Gly Lys Cys Gly Thr Asn
                 85                  90                  95

Met Asp His Ala Val Val Ala Val Gly Tyr Gly Ser Glu Asn Gly Val
            100                 105                 110

Asp Tyr Trp Ile Val Arg Asn Ser Trp Gly Thr Arg Trp Gly Glu Asp
        115                 120                 125

Gly Tyr Ile Arg Met Glu Arg Asn Val Ala Ser Lys Ser Gly Lys Cys
    130                 135                 140

Gly Ile Xaa Ile Glu Ala Ser Tyr Pro Val Lys Tyr
145                 150                 155

<210> SEQ ID NO 43
<211> LENGTH: 167
<212> TYPE: PRT
<213> ORGANISM: Brassica napus
<220> FEATURE:
<221> NAME/KEY: SITE
<222> LOCATION: 1, 2, 4, 5, 10, 138
<223> OTHER INFORMATION: Xaa is unknown

<400> SEQUENCE: 43

Xaa Xaa Asn Xaa Xaa Leu Met Asp Tyr Xaa Phe Gln Phe Ile Met Lys
  1               5                  10                  15

Asn Gly Gly Leu Asn Thr Glu Lys Asp Tyr Pro Tyr His Gly Thr Asn
             20                  25                  30

Gly Lys Cys Asn Ser Leu Leu Lys Asn Ser Arg Val Val Thr Ile Asp
         35                  40                  45

Gly Tyr Glu Asp Val Pro Ser Lys Asp Glu Thr Ala Leu Lys Arg Ala
     50                  55                  60

Val Ser Tyr Gln Pro Val Ser Val Ala Ile Asp Ala Gly Gly Arg Ala
 65                  70                  75                  80

Phe Gln His Tyr Gln Ser Gly Ile Phe Thr Gly Lys Cys Gly Thr Thr
                 85                  90                  95

Met Asp His Ala Val Val Ala Val Gly Tyr Gly Ser Glu Asn Gly Val
            100                 105                 110

Asp Tyr Trp Ile Val Arg Asn Ser Trp Gly Thr Arg Trp Gly Glu Asp
        115                 120                 125

Gly Tyr Ile Arg Met Glu Arg Asn Val Xaa Ser Lys Ser Gly Lys Cys
```

-continued

```
           130                 135                 140
Gly Ile Ala Ile Glu Ala Ser Tyr Pro Val Lys Tyr Ser Pro Asn Pro
145                 150                 155                 160

Val Arg Gly Thr Ser Ser Val
                165

<210> SEQ ID NO 44
<211> LENGTH: 167
<212> TYPE: PRT
<213> ORGANISM: Brassica napus
<220> FEATURE:
<221> NAME/KEY: SITE
<222> LOCATION: 5, 60, 73, 76, 79, 80, 163
<223> OTHER INFORMATION: Xaa is unknown

<400> SEQUENCE: 44

Gly Cys Asn Gly Xaa Leu Met Asp Tyr Ala Phe Gln Phe Ile Met Lys
  1               5                  10                  15

Asn Gly Gly Leu Asn Thr Glu Gln Asp Tyr Pro Tyr Arg Gly Ser Asn
                20                  25                  30

Gly Lys Cys Asn Ser Leu Leu Lys Asn Ser Arg Val Val Thr Ile Asp
            35                  40                  45

Gly Tyr Glu Asp Val Pro Ser Lys Asp Glu Thr Xaa Leu Lys Arg Ala
        50                  55                  60

Val Ser Tyr Gln Pro Val Ser Val Xaa Ile Asp Xaa Gly Gly Xaa Xaa
 65                  70                  75                  80

Phe Gln His Tyr Gln Ser Gly Ile Phe Thr Gly Lys Cys Gly Thr Asn
                85                  90                  95

Met Asp His Ala Val Val Ala Val Gly Tyr Gly Ser Glu Asn Gly Val
                100                 105                 110

Asp Tyr Trp Ile Val Arg Asn Ser Trp Gly Thr Leu Trp Gly Glu Asp
            115                 120                 125

Gly Tyr Ile Arg Met Glu Arg Asn Val Ala Ser Lys Ser Lys Cys
        130                 135                 140

Gly Ile Ala Ile Glu Ala Ser Tyr Pro Val Lys Tyr Ser Pro Asn Pro
145                 150                 155                 160

Val Arg Xaa Thr Ser Ser Val
                165

<210> SEQ ID NO 45
<211> LENGTH: 168
<212> TYPE: PRT
<213> ORGANISM: Brassica napus
<220> FEATURE:
<221> NAME/KEY: SITE
<222> LOCATION: 143, 148, 150, 151, 154
<223> OTHER INFORMATION: Xaa is unknown

<400> SEQUENCE: 45

Gly Cys Asn Gly Gly Leu Met Asp Tyr Ala Phe Gln Phe Ile Met Lys
  1               5                  10                  15

Asn Gly Gly Leu Asn Thr Glu Gln Asp Tyr Pro Tyr Arg Gly Ser Asn
                20                  25                  30

Gly Lys Cys Asn Ser Leu Leu Lys Asn Ser Arg Val Val Thr Ile Asp
            35                  40                  45

Gly Tyr Glu Asp Val Pro Thr Glu Asp Glu Thr Ala Leu Lys Arg Ala
        50                  55                  60

Val Ser Tyr Gln Pro Val Ser Val Ala Ile Glu Ala Gly Gly Arg Val
 65                  70                  75                  80
```

```
Phe Gln His Tyr Gln Ser Gly Ile Phe Thr Gly Lys Cys Gly Thr Asn
                85                  90                  95

Leu Asp His Ala Val Val Ala Val Gly Tyr Gly Ser Glu Asn Gly Ile
            100                 105                 110

Asp Tyr Trp Ile Val Arg Asn Ser Trp Gly Thr Arg Trp Gly Glu Asp
            115                 120                 125

Gly Tyr Ile Arg Met Glu Arg Asn Leu Ala Arg Ser Lys Ser Xaa Lys
            130                 135                 140

Cys Gly Ile Xaa Val Xaa Xaa Ser Tyr Xaa Val Lys Tyr Ser Pro Asn
145                 150                 155                 160

Pro Val Arg Gly Thr Ser Ser Val
                165

<210> SEQ ID NO 46
<211> LENGTH: 168
<212> TYPE: PRT
<213> ORGANISM: Brassica napus
<220> FEATURE:
<221> NAME/KEY: SITE
<222> LOCATION: (59)..(81), 83, 86, 142, 143, 145, 146, 162
<223> OTHER INFORMATION: Xaa is unknown

<400> SEQUENCE: 46

Gly Cys Asn Gly Gly Leu Met Asp Tyr Ala Phe Gln Phe Ile Met Lys
1               5                   10                  15

Asn Gly Gly Leu Asn Thr Glu Gln Asp Tyr Pro Tyr Arg Gly Ser Asn
                20                  25                  30

Gly Lys Cys Asn Ser Leu Leu Lys Asn Ser Arg Val Val Thr Ile Asp
            35                  40                  45

Gly Tyr Glu Asp Val Pro Thr Glu Asp Glu Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Gln Xaa Tyr Gln Xaa Gly Ile Phe Thr Gly Lys Cys Gly Thr Asn
                85                  90                  95

Leu Asp His Ala Val Val Ala Val Gly Tyr Gly Ser Glu Asn Gly Ile
            100                 105                 110

Asp Tyr Trp Ile Val Arg Asn Ser Trp Gly Thr Arg Trp Gly Glu Asp
            115                 120                 125

Gly Tyr Ile Arg Met Glu Arg Asn Leu Ala Arg Ser Lys Xaa Xaa Lys
            130                 135                 140

Xaa Xaa Ile Ala Val Glu Ala Ser Tyr Pro Val Lys Tyr Ser Pro Asn
145                 150                 155                 160

Pro Xaa Arg Gly Thr Ser Ser Val
                165

<210> SEQ ID NO 47
<211> LENGTH: 120
<212> TYPE: PRT
<213> ORGANISM: Brassica napus
<220> FEATURE:
<221> NAME/KEY: SITE
<222> LOCATION: (1)..(10)
<223> OTHER INFORMATION: Xaa is unknown

<400> SEQUENCE: 47

Xaa Xaa Xaa Xaa Xaa Xaa Xaa Xaa Xaa Xaa Phe Gln Phe Ile Met Lys
1               5                   10                  15
```

-continued

```
Asn Gly Gly Leu Asn Thr Glu Gln Asp Tyr Pro Tyr Arg Gly Ser Asn
         20                  25                  30

Gly Lys Cys Asn Ser Leu Leu Asn Ser Arg Val Val Thr Ile Asp Gly
     35                  40                  45

Tyr Glu Asp Val Pro Thr Glu Asp Thr Ala Leu Lys Arg Ala Val
     50                  55                  60

Ser Tyr Gln Pro Val Ser Val Ala Ile Glu Ala Gly Gly Arg Val Phe
 65                  70                  75                  80

Gln His Tyr Gln Ser Gly Ile Phe Thr Gly Lys Cys Gly Thr Asn Leu
                 85                  90                  95

Asp His Ala Val Val Ala Val Gly Tyr Gly Ser Glu Asn Gly Ile Asp
                100                 105                 110

Tyr Trp Ile Val Arg Asn Ser Trp
                115                 120
```

<210> SEQ ID NO 48
<211> LENGTH: 105
<212> TYPE: PRT
<213> ORGANISM: Brassica napus
<220> FEATURE:
<221> NAME/KEY: SITE
<222> LOCATION: 1, 2, 4, 6, 9, 10, 66
<223> OTHER INFORMATION: Xaa is unknown

<400> SEQUENCE: 48

```
Xaa Xaa Asn Xaa Gly Xaa Met Asp Xaa Xaa Phe Gln Phe Val Ile Lys
 1                   5                  10                  15

Asn His Gly Ile Asp Thr Glu Lys Asp Tyr Pro Tyr Gln Glu Arg Asp
                 20                  25                  30

Gly Thr Cys Lys Lys Asp Lys Leu Asn Arg Lys Val Val Thr Ile Asp
     35                  40                  45

Ser Tyr Ala Gly Val Lys Ser Asn Asp Glu Lys Ala Leu Leu Glu Ala
 50                  55                  60

Val Xaa Ala Gln Pro Val Ser Val Gly Ile Cys Gly Ser Glu Arg Ala
 65                  70                  75                  80

Phe Gln Leu Tyr Ser Lys Gly Ile Phe Ser Gly Pro Cys Ser Thr Ser
                 85                  90                  95

Leu Asp His Ala Val Leu Ile Val Gly
                100                 105
```

<210> SEQ ID NO 49
<211> LENGTH: 225
<212> TYPE: PRT
<213> ORGANISM: Brassica napus
<220> FEATURE:
<221> NAME/KEY: SITE
<222> LOCATION: 130, 131, 135, 147
<223> OTHER INFORMATION: Xaa is unknown

<400> SEQUENCE: 49

```
Gln Thr Tyr Asn Met Ala Ser Ser Pro Lys Leu Leu Ser Leu Leu Leu
 1                   5                  10                  15

Leu Tyr Val Phe Val Ser Leu Ala Ser Gly Tyr Glu Ser Ile Ile Ser
                 20                  25                  30

Asp Asn His Leu Ser Leu Pro Ser Asp Arg Ser Trp Arg Thr Asp Glu
                 35                  40                  45

Glu Val Ile Ser Ile Tyr Leu Arg Trp Ser Leu Glu His Gly Lys Ser
 50                  55                  60

Asn Ser Asn Ser Asn Gly Ile Ile Asn Gln Gln Asp Glu Arg Phe Asn
```

```
                65                  70                  75                  80
Ile Phe Lys Asp Asn Leu Arg Phe Ile Asp Leu His Asn Asp Asn Asn
                    85                  90                  95

Lys Asn Ala Thr Tyr Lys Leu Gly Leu Thr Ile Phe Ala Asp Leu Thr
                100                 105                 110

Asn Asp Glu Tyr Arg Ser Leu Tyr Leu Gly Ala Arg Thr Glu Pro Val
                115                 120                 125

Arg Xaa Xaa Thr Lys Ala Xaa Asn Val Asn Met Lys Tyr Ser Ala Ala
    130                 135                 140

Val Asn Xaa Val Glu Val Pro Glu Thr Val Asp Trp Arg Lys Lys Gly
145                 150                 155                 160

Ala Val Asn Ala Ile Lys Asp Gln Gly Thr Cys Gly Ser Cys Trp Ala
                165                 170                 175

Phe Ser Thr Ala Ala Val Glu Gly Ile Asn Lys Ile Val Thr Gly
                180                 185                 190

Glu Leu Val Ser Leu Ser Glu Gln Glu Leu Val Asp Cys Asp Lys Ser
                195                 200                 205

Tyr Asn Gln Gly Cys Asn Gly Gly Leu Met Asp Tyr Ala Phe Gln Phe
    210                 215                 220

Ile
225

<210> SEQ ID NO 50
<211> LENGTH: 230
<212> TYPE: PRT
<213> ORGANISM: Brassica napus
<220> FEATURE:
<221> NAME/KEY: SITE
<222> LOCATION: 135, 136, 140, 152
<223> OTHER INFORMATION: Xaa is unknown

<400> SEQUENCE: 50

Arg Lys Pro Thr Lys Gln Thr Tyr Asn Met Ala Ser Ser Pro Lys Leu
  1               5                  10                  15

Leu Ser Leu Leu Leu Leu Tyr Val Phe Val Ser Leu Ala Ser Gly Tyr
                 20                  25                  30

Glu Ser Ile Ile Ser Asp Asn His Leu Ser Leu Pro Ser Asp Arg Ser
                 35                  40                  45

Trp Arg Thr Asp Glu Val Ile Ser Ile Tyr Leu Arg Trp Ser Leu
    50                  55                  60

Glu His Gly Lys Ser Asn Ser Asn Ser Asn Gly Ile Ile Asn Gln Gln
 65                  70                  75                  80

Asp Glu Arg Phe Asn Ile Phe Lys Asp Asn Leu Arg Phe Ile Asp Leu
                 85                  90                  95

His Asn Glu Asn Asn Lys Asn Ala Thr Tyr Lys Leu Gly Leu Thr Ile
                100                 105                 110

Phe Ala Asp Leu Thr Asn Asp Glu Tyr Arg Ser Leu Tyr Leu Gly Ala
                115                 120                 125

Arg Thr Glu Pro Val Arg Xaa Xaa Thr Lys Ala Xaa Asn Val Asn Met
    130                 135                 140

Lys Tyr Ser Ala Ala Val Asn Xaa Val Glu Val Pro Glu Thr Val Asp
145                 150                 155                 160

Trp Arg Lys Lys Gly Ala Val Asn Ala Ile Lys Asp Gln Gly Thr Cys
                165                 170                 175

Gly Ser Cys Trp Ala Phe Ser Thr Ala Ala Val Glu Gly Ile Asn
                180                 185                 190
```

```
Lys Ile Val Thr Gly Glu Leu Val Ser Leu Ser Glu Gln Glu Leu Val
            195                 200                 205

Asp Cys Asp Lys Ser Tyr Asn Gln Gly Cys Asn Gly Gly Leu Met Asp
            210                 215                 220

Tyr Ala Phe Gln Phe Ile
225                 230

<210> SEQ ID NO 51
<211> LENGTH: 225
<212> TYPE: PRT
<213> ORGANISM: Brassica napus
<220> FEATURE:
<221> NAME/KEY: SITE
<222> LOCATION: 131, 132, 136, 148, 218
<223> OTHER INFORMATION: Xaa is unknown

<400> SEQUENCE: 51

Lys Gln Thr Tyr Asn Met Ala Ser Ser Ala Lys Leu Leu Ser Leu Leu
  1               5                  10                  15

Leu Leu Tyr Val Phe Ile Ser Leu Ala Ser Ser Asp Glu Ser Ile Ile
             20                  25                  30

Asn Asp Asn His Leu Ile Leu Pro Ser Asp Arg Ser Trp Arg Thr Asp
             35                  40                  45

Glu Glu Val Met Ser Ile Tyr Leu Lys Trp Ser Leu Glu His Gly Lys
         50                  55                  60

Ser Asn Ser Asn Ser Asn Gly Ile Ile Asn Gln Gln Asp Glu Arg Phe
 65                  70                  75                  80

Asn Ile Phe Lys Asp Asn Leu Arg Phe Ile Asp Leu His Asn Glu Asn
                 85                  90                  95

Asn Lys Asn Ala Thr Tyr Lys Leu Gly Leu Thr Ile Phe Ala Asp Leu
            100                 105                 110

Thr Asn Asp Glu Tyr Arg Ser Leu Tyr Leu Gly Ala Arg Thr Glu Pro
            115                 120                 125

Val Arg Xaa Xaa Thr Lys Ala Xaa Asn Val Asn Met Lys Tyr Ser Ala
        130                 135                 140

Ala Val Asn Xaa Val Glu Val Pro Glu Thr Val Asp Trp Arg Gln Lys
145                 150                 155                 160

Gly Ala Val Asn Ala Ile Lys Asn Gln Gly Ser Cys Gly Ser Cys Trp
                165                 170                 175

Ala Phe Ser Thr Ala Ala Ala Val Glu Gly Ile Asn Lys Ile Val Thr
            180                 185                 190

Gly Glu Leu Ile Ser Leu Ser Glu Gln Glu Leu Val Asp Cys Asp Lys
            195                 200                 205

Ser Tyr Asn Gln Gly Cys Asn Gly Gly Xaa Met Asp Tyr Ala Phe Gln
            210                 215                 220
Phe
225

<210> SEQ ID NO 52
<211> LENGTH: 675
<212> TYPE: DNA
<213> ORGANISM: Brassica napus
<220> FEATURE:
<221> NAME/KEY: misc_feature
<222> LOCATION: 388, 390, 391, 402, 403, 439..441
<223> OTHER INFORMATION: n is unknown

<400> SEQUENCE: 52
```

| | |
|---|---|
| caaacataca atatggcttc ctcaccaaaa ctcctctctt tacttctctt atacgtcttc | 60 |
| gtttcgttag cctccggtta tgagtccatc atcagtgaca accatctcag tcttccatct | 120 |
| gaccgttcgt ggagaaccga tgaagaagtg atatccatct acttaagatg gtccttggag | 180 |
| cacgggaaaa gtaacagcaa cagcaacggt attatcaacc aacaagacga aagattcaat | 240 |
| attttcaaag acaacctaag attcatcgat ctacacaacg acaacaacaa gaacgctact | 300 |
| tacaagcttg gtctaaccat attcgctgat ctcactaacg atgagtaccg gagtttatac | 360 |
| ctcggggcaa gaaccgagcc tgtccgcngn ntcactaagg cnnagaacgt taacatgaaa | 420 |
| tactcagccg cagtaaacnn ngtggaggtt ccggagacgg ttgactggag aaagaaagga | 480 |
| gccgttaatg ccattaaaga ccaaggaact tgcggaagtt gttgggcgtt ttcaacagct | 540 |
| gcagcagtag aaggtataaa caagatcgta acaggagaac tcgtatcttt gtccgaacaa | 600 |
| gaacttgtcg actgcgacaa atcgtacaac caaggctgta acggcggtct aatggattat | 660 |
| gcttttcaat tcata | 675 |

<210> SEQ ID NO 53
<211> LENGTH: 690
<212> TYPE: DNA
<213> ORGANISM: Brassica napus
<220> FEATURE:
<221> NAME/KEY: misc_feature
<222> LOCATION: 403, 406, 417..419, 455, 456
<223> OTHER INFORMATION: n is unknown

<400> SEQUENCE: 53

| | |
|---|---|
| agaaaaccaa caaaacaaac atacaatatg gcttcctcac caaaactcct ctctttactt | 60 |
| ctcttatacg tcttcgtttc gttagcctcc ggttatgagt ccatcatcag tgacaaccat | 120 |
| ctcagtcttc catctgaccg ttcgtggaga accgatgaag aagtgatatc catctactta | 180 |
| agatggtcct tggagcacgg gaaaagcaac agcaacagca acggtattat caaccaacaa | 240 |
| gacgaaagat tcaatatttt caaagacaac ctaagattca tcgatctaca acgagaaac | 300 |
| aacaagaact ctacttacaa gcttggtcta accatattcg ctgatctcac taacgatgag | 360 |
| taccggagtt tatacctcgg ggcaagaacc gagcctgtcc gcngcntcac taaggcnnng | 420 |
| aacgttaaca tgaaatactc agccgcagta acgnngtgg aggttccgga gacggttgac | 480 |
| tggagaaaga aaggagccgt taatgccatt aaagaccaag gaacttgcgg aagttgttgg | 540 |
| gcgttttcaa cagctgcagc agtagaaggt ataaacaaga tcgtaacagg agaactcgta | 600 |
| tctttgtccg aacaagaact tgtcgactgc gacaaatcgt acaaccaagg ctgtaacggc | 660 |
| ggtctaatgg attatgcttt tcaattcata | 690 |

<210> SEQ ID NO 54
<211> LENGTH: 679
<212> TYPE: DNA
<213> ORGANISM: Brassica napus
<220> FEATURE:
<221> NAME/KEY: misc_feature
<222> LOCATION: 392, 395, 406..408, 443..445, 652, 653
<223> OTHER INFORMATION: n is unknown

<400> SEQUENCE: 54

| | |
|---|---|
| aaaacaaaca tacaatatgg cttcgtcagc gaaactcctc tctttacttc tcttgtacgt | 60 |
| cttcatttca ttagcctcca gtgatgagtc catcatcaac gacaaccatc tcattcttcc | 120 |
| atctgaccgc tcgtggagaa ccgatgaaga agtgatgtcc atctacttaa aatggtcctt | 180 |
| ggagcacggg aaaagtaaca gcaacagcaa cggtattatc aaccaacaag atgaaagatt | 240 |

```
caatattttc aaagacaaacc taagattcat cgatctacac aacgagaaca acaagaacgc    300
tacttacaag cttggtctaa ccatattcgc tgatctcact aacgatgagt accggagttt    360
atacctcggg gcaagaaccg agcctgtccg cngcntcact aaggcnnnga acgttaacat    420
gaaatactca gccgcagtaa acnnngtgga ggttccggag acggttgact ggagacagaa    480
aggagccgtt aatgccatta aaaccaagg atcttgcgga agttgttggg cgttttcaac    540
agctgcagca gtagaaggca taaacaagat cgtaacagga gagctcatat ctctgtccga    600
acaagaactt gtcgactgcg acaaatcata caaccaaggc tgtaacggcg gnntaatgga    660
ttatgctttt caattcatc                                                 679

<210> SEQ ID NO 55
<211> LENGTH: 322
<212> TYPE: DNA
<213> ORGANISM: Brassica napus
<220> FEATURE:
<221> NAME/KEY: misc_feature
<222> LOCATION: 5..7, 57
<223> OTHER INFORMATION: n is unknown

<400> SEQUENCE: 55
cgtcnnngaa actcctctct ttacttctct tgtacgtctt catttcatta gcctccngtg    60
atgagtccat catcaacgac aaccatctca ttcttccatc tgaccgctcg tggagaaccg    120
atgaagaagt gatgtccatc tacttaaaat ggtccttgga gcacgggaaa agtaacagca    180
acagcaacgg tattatcaac caacaagatg aaagattcaa tattttcaaa gacaacctaa    240
gattcatcga tctacacaac gagaacaaca agaacnctac ttacaagctt ggtctaacca    300
tattcgctga tctcactaac ga                                             322

<210> SEQ ID NO 56
<211> LENGTH: 307
<212> TYPE: DNA
<213> ORGANISM: Brassica napus
<220> FEATURE:
<221> NAME/KEY: misc_feature
<222> LOCATION: 7, 269, 279, 282
<223> OTHER INFORMATION: n is unknown

<400> SEQUENCE: 56
tagaaancca acaaaacaaa catacaatat ggcttcgtca gcgaaactcc tctctttact    60
tctcttgtac gtcttcattt cattagcctc cagtgatgag tccatcatca acgacaacca    120
tctcattctt ccatctgacc gctcgtggag aaccgatgaa gaagtgatgt ccatctactt    180
aaaatggtcc ttggagcacg ggaaaagtaa cagcaacagc aacggtatta tcaaccaaca    240
agatgaaaga ttcaatattt tcaaagacna cctaagatnc ancgatctac acaacgagaa    300
caacaag                                                              307

<210> SEQ ID NO 57
<211> LENGTH: 288
<212> TYPE: DNA
<213> ORGANISM: Brassica napus
<220> FEATURE:
<221> NAME/KEY: misc_feature
<222> LOCATION: 45, 273, 283, 286
<223> OTHER INFORMATION: n is unknown

<400> SEQUENCE: 57
aaactagaaa accaacaaaa caaacataca atatggcttc gtcancgaaa ctcctctctt    60
```

```
tacttctctt gtacgtcttc atttcattag cctccagtga tgagtccatc atcaacgaca    120
accatctcat tcttccatct gaccgctcgt ggagaaccga tgaagaagtg atgtccatct    180
acttaaaatg gtccttggag cacgggaaaa gtaacagcaa cagcaacggt attatcaacc    240
aacaagatga aagattcaat attttcaaag acnacctaag atncancg                288
```

<210> SEQ ID NO 58
<211> LENGTH: 255
<212> TYPE: DNA
<213> ORGANISM: Brassica napus
<220> FEATURE:
<221> NAME/KEY: misc_feature
<222> LOCATION: 136, 187, 192
<223> OTHER INFORMATION: n is unknown

<400> SEQUENCE: 58

```
gaacaaccaa gccaaacata caatatggct tcctcaacaa aactcatttc tttacttctc     60
ctatacgtcg tcgtttcatt agcctccggt gatgagtcca ctaccattaa caaccatctc    120
aatcttccat cggacngctc atggagaacc gatgaagaag tgaggtccat ctacttacag    180
tggtgtncgg angggaaaac tagcaacaac aacggtatcg tcaaccaaca agacgaaaag    240
ttcaatattt tcaaa                                                     255
```

<210> SEQ ID NO 59
<211> LENGTH: 1577
<212> TYPE: DNA
<213> ORGANISM: Brassica napus

<400> SEQUENCE: 59

```
cttgttttgg tttccctgta agaaaagaaa tgtcaccatc atcgtcttct tcctttgttt     60
ctctcacttt cttctccctt cttctagttt cttctctgag cttctcatca tcatcttccg    120
atgacatctc cgagctgttc gacgcttggt gccagagaca cggcaaaacg tacgcttcgg    180
aggaagagag acaacacagg attcgaatct ttaaagacaa tcacgacttc gtcacacgac    240
acaacaacat cgctaactct acttactctc tctcactcaa tgccttcgcg gatctgactc    300
accacgagtt caaggcctct cgtcttggag gattctctgc ttcttcagct cctttgctga    360
tggctaaggg acagagtgtt gagaacgttc ggggaaaggt tccagattct gttgattgga    420
ggaagaaagg agctgttact aatgtcaaag atcaaggaag ctgcggagcg tgttggtctt    480
tctcggcgac tggagctatg gaaggaatca accagattgt aacaggagat ctcatcagcc    540
tctctgagca agaactcatt gattgtgata agtcatacaa cgatggatgc aatggtggtc    600
tcatggacta cgcttttcaa tttgtcatta aaaaccatgg gattgacaca gagaaagatt    660
atccttatca agaacgtgat ggcacctgtm agaaagataa gttgaataga aaggttgtga    720
caattgatag ctacgctggt gtaaaatcaa atgacgagaa agcgttacta gaagctgtag    780
cggctcagcc agttagtgtt ggtatctgtg ggagcgagag agcgtttcag ttatactcta    840
agggaatatt ctctggccca tgttcaacat cattggacca cgcagtgctc atcgtaggat    900
acggttcaaa gaacggtgtt gattactgga tcgtgaagaa ctcttgggga aagagttggg    960
gaatggatgg gtttatccac atgcagcgta acaccggcaa cgcagaagga gtatgcggaa   1020
tcaacatgct ggcttcatat cccatcaaga cacatccaaa ccctcctcca ccgtcccctc   1080
ccggccccac gaaatgcaac ctttcacct attgttcagc tgatgagact tgttgctgtg   1140
cgagaaactt gtttggtttg tgtttctcgt ggaaatgctg cgagctagag tctgctgtgt   1200
gttgcaagga tggtcgtcat tgttgtccgc gtgattaccc cgtctgtgat accaccagaa   1260
```

```
gtctttgcct taagaaaact ggcaatttca cagagatcaa gcccttctgg aagaagaatg   1320
cgtccaataa acttggcaag ttcgaggaat gggttatgta agaggaagtt ttcaaactct   1380
ttcacacggt aagcctcttt ggattcgttt atctataagc tgagagatga ttactttata   1440
gctgttgttg tgatatgtat tattagtctc ttatttggat gtatacaaac ttttgaatca   1500
ataaaaggtt acttgcagga cacaataaaa aaaaaaaaaa aaaaaaaaaa aaaaaaaaaa   1560
aaaaaaaaaa aaaaaaa                                                  1577

<210> SEQ ID NO 60
<211> LENGTH: 1553
<212> TYPE: DNA
<213> ORGANISM: Brassica napus

<400> SEQUENCE: 60
aaaagctctt cttgtttcgg tttccctgta aggaaaagaa atgtcaccat catcgtcttc     60
ttcctttgtc tctatcactt tcttctccct tcttctagtt tcttctctga gcttcccatc    120
atcatcttcc gatgacatct ccgagctgtt cgacgcttgg tgccagagac acggcaaaac    180
gtacgcttcg gaagaagaga acaacacag gattgaaatc tttagagaca atcacgactt     240
cgtcacacga cacaacggca tcgctaactc tacttactct ctctcactca atgccttcgc    300
ggatctgact caccacgagt tcaaggcctc tcgtcttgga ctctctgctt cttcagctcc    360
gttgctggtg gctaagggag aaagtgttga aacgttgggg gcaaagttc cagattctgt     420 tgattggagg aagaaaggag ctgttactaa tgtcaaagat caaggaagct gcggagcgtg    480
ttggtctttc tcggcgactg gagcaatgga aggaatcaac cagattgtaa caggagatct    540
catcagcctc tctgagcagg aactaattga ttgtgacaag tcctacaacg atggatgcaa    600
tggtggtctc atggactacg cttttcaatt tgtcattaaa aaccatggaa tcgacacaga    660
gaaagattat ccttatcaag aacgtgatgg cacctgtaaa aagataagt tgaaaagaaa     720 ggttgtgaca attgatagct atgctggcgt aaaatcaaac gacgagaaag cgttactgga    780
agctgtagcg gctcagccag ttagtgttgg catctgtggc agcgagagag cgtttcagct    840
atactctaag ggaatattct ctggcccatg ttcaacatca ttggaccacg cagtgctcat    900
cgtaggatac ggttcacaga acggtgttga ttactggatc gtgaagaact cttggggaaa    960
gagttggggt atggatgggt ttatgcacat gcagcgtaac accggcaact cggaaggagt   1020
atgtggaatc aaatatgctcg cttcgtatcc catcaagaca catccaaacc ctcctccacc   1080
gtccccttcc ggccccacga aatgcaacct tttcacctat tgtgcagctg atgagacttg   1140
ttgctgtgcg agaaacttgt ttggtttgtg tttctcgtgg aaatgccgcg agctagagtc   1200
tgctgtgtgt tgtaaggatg gtcgtcattg ttgtcctcgt gattacccg tctgtgatac    1260 aaccagaagt ctttgcctaa agaaaactgg caatttcaca gagatcaaac ccttctggaa   1320
gaagaatgcg tccaataaac ttggcaagtt cgaggaatgg ttatgtaag agaagttttt    1380 taaactcttc cacacggaag cctctttgga ttcgttatgt ataagctgag agatgattat    1440
tttatagctg ttgttgtgat atgtattatt agtatctcat tggatgtat acaaactttt    1500 gaatcaataa agggtatctg caggacacat taaataaaaa aaaaaaaaa aaa           1553

<210> SEQ ID NO 61
<211> LENGTH: 1390
<212> TYPE: DNA
<213> ORGANISM: Brassica napus
```

-continued

```
<400> SEQUENCE: 61
caactatcaa aactagaaaa ccaacaaaac aaacatacaa tatggcttcg tcagcgaaac      60
tcctctcttt acttctcttg tacgtcttca tttcattagc ctccagtgat gagtccatca     120
tcaacgacaa ccatctcatt cttccatctg accgctcgtg gagaaccgat gaagaagtga    180
tgtccatcta cttaaaatgg tccttggagc acgggaaaag taacagcaac agcaacggta    240
ttatcaacca acaagatgaa agattcaata ttttcaaaga caacctaaga ttcatcgatc    300
tacacaacga gaacaacaag aacgctactt acaagcttgg tctaaccata ttcgctgatc    360
tcactaacga tgagtaccgg agtttatacc tcggggcaag aaccgagcct gtccgccgca    420
tcactaaggc caagaacgtt aacatgaaat actcagccgc agtaaacgac gtggaggttc    480
cggagacggt tgactggaga cagaaaggag ccgttaatgc cattaaaaac caaggatctt    540
gcggaagttg ttgggcgttt tcaacagctg cagcagtaga aggcataaac aagatcgtaa    600
caggagagct catatctctg tccgaacaag aacttgtcga ctgcgacaaa tcatacaacc    660
aaggctgtaa cggcggtcta atggattatg cttttcaatt catcatgaaa aacgcggat    720 taaacaccga gcaagactat ccttaccacg gaaccaatgg caaatgcaac tctttactta    780
aaaattcgag agttgtgact atcgatggat acgaagatgt tcctagtaaa gatgaaaccg    840
cgttgaagag agcagtttcg taccagcctg tgagtgttgc tattgatgct ggtggaagag    900
ctttccaaca ttaccaatct ggaatcttca ctggaaagtg tggtacgact atggatcacg    960
ctgttgtggc ggttggttat ggatcagaga acggtgttga ctattggatt gtacgtaact   1020
cttggggtac aagctgggga gaggatggtt acattaggat ggagagaaac gtggcgtcca   1080
aatccggtaa gtgtgggatt gcgattgaag cctcgtatcc ggttaagtac agcccaaacc   1140
cggttcgtgg aaccagcagt gtttgaagtt aacaaaaaga atctcatgca gtaatcaaat   1200
tgggattgtt ataagttaaa ttaatcttgt attattgttt gtatgtatag tatttcgaaa   1260
aaaattgatt caccataggg atttaatctg tataaatctc tatgttggtc aatatcattt   1320
cattcaaaga atatttgctt tggcttgatt atgtattaag agaaatataa taaaaaaaaa   1380
aaaaaaaaa                                                           1390

<210> SEQ ID NO 62
<211> LENGTH: 1434
<212> TYPE: DNA
<213> ORGANISM: Brassica napus

<400> SEQUENCE: 62
caactatcaa aactagaaaa ccaacaaaac aaacatacaa tatggcttcc tcaccaaaac     60
tcctctcttt acttctctta tacgtcttcg tttcgttagc ctccggttat gagtccatca    120
tcagtgacaa ccatctcagt cttccatctg accgttcgtg gagaaccgat gaagaagtga    180
tatccatcta cttaagatgg tccttggagc acgggaaaag taacagcaac agcaacggta    240
ttatcaacca acaagacgaa agattcaata ttttcaaaga caacctaaga ttcatcgatc    300
tacacaacga gaacaacaag aacgctactt acaagcttgg tctaaccata ttcgctgatc    360
tcactaacga tgagtaccgg agtttatacc tcggggcaag aaccgagcct gtccgccgca    420
tcactaaggc caagaacgtt aacatgaaat actcagccgc agtaaacgac gtggaggttc    480
cggagacggt tgactggaga agaaaggag ccgttaatgc cattaaagac caaggaactt     540
gcggaagttg ttgggcgttt tcaacagctg cagcagtaga aggtataaac aagatcgtaa    600
caggagaact cgtatctttg tccgaacaag aacttgtcga ctgcgacaaa tcgtacaacc    660
```

```
aaggctgtaa cggcggtcta atggattatg cttttcaatt cataatgaaa aacggcggat    720
taaacaccga gaaagactat ccttaccacg gaaccaatgg caaatgcaac tctttactta    780
agaattcaag agttgtaact atcgatggat acgaagatgt tcctagtaaa gatgaaaccg    840
cgttgaagag agcagtttca taccagcctg tgagtgttgc tattgatgct ggtggaagag    900 cttccaaca ttaccaatct ggaatcttca ctggaaagtg tggtacgaat atggatcacg    960
ctgtggtggc ggttggttat ggtcagaga acggcgttga ctattggatt gtacgtaact   1020
cttggggtac acgttgggga gaggatggtt acattaggat ggagagaaac gtggcgtcta   1080
aatccggtaa gtgtgggatt gcgatagaag cctcgtatcc ggttaagtac agcccaaacc   1140
cggttcgtgg aaccagcagt gtttgaagtt aacaaaaaga atctcatgca gtaatcaaat   1200
tgggattgtt ataagttaaa ttaatcttgt attattgttt gtatgtatag tatttcggaa   1260
aaaaaaatga ttcaccatag ggatttaatc tgtataaatc tctaggttgg tcaaatatca   1320
tttcattcaa agaatatttg mctttgactt gattatgtat aagagaaat ataataaaat   1380 ggtatatttc tcaacagcat tggtttcgct gaaaaaaaaa aaaaaaaaa aaaa          1434
```

<210> SEQ ID NO 63
<211> LENGTH: 1441
<212> TYPE: DNA
<213> ORGANISM: Brassica napus

<400> SEQUENCE: 63

```
agaaaaccaa caaacaaac atacaatatg gcttcgtcag cgaaactcct ctctttactt     60
ctcttgtacg tcttcatttc attagcctcc agtgatgagt ccatcatcaa cgacaaccat    120
ctcattcttc catctgaccg ctcgtggaga accgatgaag aagtgatgtc catctactta    180
aaatggtcct tggagcacgg gaaaagtaac agcaacagca acggtattat caaccaacaa    240
gatgaaagat tcaatatttt caaagacaac ctaagattca tcgatctaca caacgagaac    300
aacaagaacg ctacttacaa gcttggtcta accatattcg ctgatctcac taacgatgag    360
taccggagtt tatacctcgg ggcaagaacc gagcctgtcc gccgcatcac taaggccaag    420
aacgttaaca tgaaatactc agccgcagta acgacgtgg aggttccgga gacggttgac    480
tggagacaga aaggagccgt taatgccatt aaaaaccaag gatcttgcgg aagttgttgg    540
gcgttttcaa cagctgcagc agtagaaggc ataaacaaga tcgtaacagg agagctcata    600
tctctgtccg aacaagaact tgtcgactgc gacaaatcat acaaccaagg ctgtaacggc    660
ggtctaatgg attatgcttt tcaattcatc atgaaaaacg gcggattaaa caccgagcaa    720
gactatcctt accacggaac caatggcaaa tgcaactctt tacttaaaaa ttcgagagtt    780
gtgactatcg atggatacga agatgttcct agtaaagatg aaaccgcgtt gaagagagca    840
gtttcgtacc agcctgtgag tgttgctatt gatgctggtg gaagagcttt ccaacattac    900
caatctggaa tcttcactgg aaagtgtggt acgactatgg atcacgctgt tgtggcggtt    960
ggttatggat cagagaacgg tgttgactat tggattgtac gtaactcttg gggtacaagc   1020
tggggagagg atggttacat taggatggag agaaacgtgg cgtccaaatc cggtaagtgt   1080
gggattgcga ttgaagcctc gtatccggtt aagtacagcc caaacccggt tcgtggaacc   1140
agcagtgttt gaagttaaca aaaagaatct catgcagtaa tcaaattggg attgttataa   1200
gttaaattaa tcttgtatta ttgtttgtat gtatagtatt tcgaaaaaaa ttgattcacc   1260 ataggggattt aatctgtata aatctctatg ttggtcaata tcatttcatt caaagaatat   1320
```

-continued

| ttgctttggc ttgattatgt attaagagaa atataataaa aatgatatat ttctcaaaaa | 1380 |
| aaaaaaaaaa aaaaaaaaaa aaaaaaaaaa aaaaaaaaaa aaaaaaaaaa aaaaaaaaaa | 1440 |
| a | 1441 |

<210> SEQ ID NO 64
<211> LENGTH: 1474
<212> TYPE: DNA
<213> ORGANISM: Brassica napus

<400> SEQUENCE: 64

| cagaactaga acaaccaagc caaacataca atatggcttc ctcaacaaaa ctcatttctt | 60 |
| tacttctcct atacgtcgtc gtttcattag cctccggtga tgagtccact accattaaca | 120 |
| accatctcaa tcttccatcg gacggctcat ggagaaccga tgaagaagtg aggtccatct | 180 |
| acttacagtg gtgtgcggag cacgggaaaa ctagcaacaa caacggtatc gtcaaccaac | 240 |
| aagacgaaaa gttcaatatt tcaaagaca acctaaggtt cattgatcta cacaatgaga | 300 |
| acaacaagaa cgctacttac aagcttggtc tcaccatatt ctctgatctc actaacgatg | 360 |
| agtaccggag gttatacctc ggggcaagaa ccgagtctgt ccgccgcatc actaaggcca | 420 |
| agaacgttaa catgaaatac tcggccgcag taaacgacgt ggaggttccg gagacggttg | 480 |
| attggagacg gaaaggagcc gttaatgcca ttaaaaacca aggaacttgc ggaagttgtt | 540 |
| gggcgttttc gacagctgca gcagtagaag gtataaacaa gatcgtaaca ggagaactca | 600 |
| tatctctgtc cgaacaagaa cttgtcgact gcgacagatc ctacaaccaa ggctgcaacg | 660 |
| gtggtttaat ggactatgct tttcaattca tcatgaaaaa cggcggtttg aacaccgagc | 720 |
| aagattatcc ttaccgtggt tccaatggaa atgcaattc tttactgaag aattcaagag | 780 |
| ttgtaactat tgatggttac gaagatgttc ctactgaaga tgaaacggcg ttgaagagag | 840 |
| cagtttcata ccagcccgtg agtgttgcca ttgaagctgg tggaagagtt ttccaacatt | 900 |
| accaatcggg gatcttcact ggaaagtgtg ggacaaatct agatcatgca gtggtggctg | 960 |
| ttggttatgg ttcagagaac ggtattgact attggattgt aaggaactcg tggggtacac | 1020 |
| gttggggaga ggatggttac attaggatgg agagaaactt ggcaaggtcc aagtccggca | 1080 |
| agtgtggaat tgcggttgaa gcctcgtacc cggttaagta cagtccaaac ccggttcgtg | 1140 |
| gaaccagcag tgtttgaagt ttttaaaata aaactcaatt gggagtttta taactaagat | 1200 |
| ttaatctcat attattgttt gtatgtatag tatatcaaaa aagaaggtat ttgatccagc | 1260 |
| atacggatt agtctgtata aatccttatg tcgatcaata tcatttcgtt caaagaaaga | 1320 |
| ttgatttggt tgtttatgta ttaagagaag tataataaaa tgatatattt ctcttaaaaa | 1380 |
| aaaaaaaaaa aaaaaaaaaa aaaaaaaaaa aaaaaaaaaa aaaaaaaaaa aaaaaaaaaa | 1440 |
| aaaaaaaaaa aaaaaaaaaa aaaaaaaaaa aaaa | 1474 |

<210> SEQ ID NO 65
<211> LENGTH: 443
<212> TYPE: PRT
<213> ORGANISM: Brassica napus

<400> SEQUENCE: 65

Met Ser Pro Ser Ser Ser Ser Phe Val Ser Leu Thr Phe Phe Ser
 1               5                  10                  15

Leu Leu Leu Val Ser Ser Leu Ser Phe Ser Ser Ser Ser Asp Asp
                20                  25                  30

Ile Ser Glu Leu Phe Asp Ala Trp Cys Gln Arg His Gly Lys Thr Tyr

-continued

```
                35                  40                  45
Ala Ser Glu Glu Arg Gln His Arg Ile Arg Ile Phe Lys Asp Asn
     50                  55                  60
His Asp Phe Val Thr Arg His Asn Asn Ile Ala Asn Ser Thr Tyr Ser
 65                  70                  75                  80
Leu Ser Leu Asn Ala Phe Ala Asp Leu Thr His His Glu Phe Lys Ala
                 85                  90                  95
Ser Arg Leu Gly Gly Phe Ser Ala Ser Ser Ala Pro Leu Leu Met Ala
                100                 105                 110
Lys Gly Gln Ser Val Glu Asn Val Arg Gly Lys Val Pro Asp Ser Val
                115                 120                 125
Asp Trp Arg Lys Lys Gly Ala Val Thr Asn Val Lys Asp Gln Gly Ser
            130                 135                 140
Cys Gly Ala Cys Trp Ser Phe Ser Ala Thr Gly Ala Met Glu Gly Ile
145                 150                 155                 160
Asn Gln Ile Val Thr Gly Asp Leu Ile Ser Leu Ser Glu Gln Glu Leu
                165                 170                 175
Ile Asp Cys Asp Lys Ser Tyr Asn Asp Gly Cys Asn Gly Gly Leu Met
            180                 185                 190
Asp Tyr Ala Phe Gln Phe Val Ile Lys Asn His Gly Ile Asp Thr Glu
            195                 200                 205
Lys Asp Tyr Pro Tyr Gln Glu Arg Asp Gly Thr Cys Xaa Lys Asp Lys
210                 215                 220
Leu Asn Arg Lys Val Val Thr Ile Asp Ser Tyr Ala Gly Val Lys Ser
225                 230                 235                 240
Asn Asp Glu Lys Ala Leu Leu Glu Ala Val Ala Ala Gln Pro Val Ser
                245                 250                 255
Val Gly Ile Cys Gly Ser Glu Arg Ala Phe Gln Leu Tyr Ser Lys Gly
            260                 265                 270
Ile Phe Ser Gly Pro Cys Ser Thr Ser Leu Asp His Ala Val Leu Ile
            275                 280                 285
Val Gly Tyr Gly Ser Lys Asn Gly Val Asp Tyr Trp Ile Val Lys Asn
            290                 295                 300
Ser Trp Gly Lys Ser Trp Gly Met Asp Gly Phe Ile His Met Gln Arg
305                 310                 315                 320
Asn Thr Gly Asn Ala Glu Gly Val Cys Gly Ile Asn Met Leu Ala Ser
                325                 330                 335
Tyr Pro Ile Lys Thr His Pro Asn Pro Pro Ser Pro Pro Gly
            340                 345                 350
Pro Thr Lys Cys Asn Leu Phe Thr Tyr Cys Ser Ala Asp Glu Thr Cys
            355                 360                 365
Cys Cys Ala Arg Asn Leu Phe Gly Leu Cys Phe Ser Trp Lys Cys Cys
370                 375                 380
Glu Leu Glu Ser Ala Val Cys Cys Lys Asp Gly Arg His Cys Cys Pro
385                 390                 395                 400
Arg Asp Tyr Pro Val Cys Asp Thr Thr Arg Ser Leu Cys Leu Lys Lys
            405                 410                 415
Thr Gly Asn Phe Thr Glu Ile Lys Pro Phe Trp Lys Lys Asn Ala Ser
            420                 425                 430
Asn Lys Leu Gly Lys Phe Glu Glu Trp Val Met
            435                 440
```

<210> SEQ ID NO 66

<211> LENGTH: 442
<212> TYPE: PRT
<213> ORGANISM: Brassica napus

<400> SEQUENCE: 66

```
Met Ser Pro Ser Ser Ser Ser Phe Val Ser Ile Thr Phe Phe Ser
 1               5                  10                  15

Leu Leu Leu Val Ser Ser Leu Ser Phe Pro Ser Ser Ser Asp Asp
                20                  25                  30

Ile Ser Glu Leu Phe Asp Ala Trp Cys Gln Arg His Gly Lys Thr Tyr
            35                  40                  45

Ala Ser Glu Glu Arg Gln His Arg Ile Glu Ile Phe Arg Asp Asn
        50                  55                  60

His Asp Phe Val Thr Arg His Asn Gly Ile Ala Asn Ser Thr Tyr Ser
 65                  70                  75                  80

Leu Ser Leu Asn Ala Phe Ala Asp Leu Thr His His Glu Phe Lys Ala
                85                  90                  95

Ser Arg Leu Gly Leu Ser Ala Ser Ala Pro Leu Leu Val Ala Lys
                100                 105                 110

Gly Glu Ser Val Glu Asn Val Gly Gly Lys Val Pro Asp Ser Val Asp
                115                 120                 125

Trp Arg Lys Lys Gly Ala Val Thr Asn Val Lys Asp Gln Gly Ser Cys
130                 135                 140

Gly Ala Cys Trp Ser Phe Ser Ala Thr Gly Ala Met Glu Gly Ile Asn
145                 150                 155                 160

Gln Ile Val Thr Gly Asp Leu Ile Ser Leu Ser Glu Gln Glu Leu Ile
                165                 170                 175

Asp Cys Asp Lys Ser Tyr Asn Asp Gly Cys Asn Gly Gly Leu Met Asp
                180                 185                 190

Tyr Ala Phe Gln Phe Val Ile Lys Asn His Gly Ile Asp Thr Glu Lys
                195                 200                 205

Asp Tyr Pro Tyr Gln Glu Arg Asp Gly Thr Cys Lys Lys Asp Lys Leu
        210                 215                 220

Lys Arg Lys Val Val Thr Ile Asp Ser Tyr Ala Gly Val Lys Ser Asn
225                 230                 235                 240

Asp Glu Lys Ala Leu Leu Glu Ala Val Ala Ala Gln Pro Val Ser Val
                245                 250                 255

Gly Ile Cys Gly Ser Glu Arg Ala Phe Gln Leu Tyr Ser Lys Gly Ile
                260                 265                 270

Phe Ser Gly Pro Cys Ser Thr Ser Leu Asp His Ala Val Leu Ile Val
                275                 280                 285

Gly Tyr Gly Ser Gln Asn Gly Val Asp Tyr Trp Ile Val Lys Asn Ser
                290                 295                 300

Trp Gly Lys Ser Trp Gly Met Asp Gly Phe Met His Met Gln Arg Asn
305                 310                 315                 320

Thr Gly Asn Ser Glu Gly Val Cys Gly Ile Asn Met Leu Ala Ser Tyr
                325                 330                 335

Pro Ile Lys Thr His Pro Asn Pro Pro Pro Ser Pro Ser Gly Pro
                340                 345                 350

Thr Lys Cys Asn Leu Phe Thr Tyr Cys Ala Ala Asp Glu Thr Cys Cys
                355                 360                 365

Cys Ala Arg Asn Leu Phe Gly Leu Cys Phe Ser Trp Lys Cys Arg Glu
        370                 375                 380

Leu Glu Ser Ala Val Cys Cys Lys Asp Gly Arg His Cys Cys Pro Arg
```

```
                385                390                395                400
Asp Tyr Pro Val Cys Asp Thr Thr Arg Ser Leu Cys Leu Lys Lys Thr
                    405                410                415
Gly Asn Phe Thr Glu Ile Lys Pro Phe Trp Lys Lys Asn Ala Ser Asn
                    420                425                430
Lys Leu Gly Lys Phe Glu Glu Trp Val Met
            435                440

<210> SEQ ID NO 67
<211> LENGTH: 374
<212> TYPE: PRT
<213> ORGANISM: Brassica napus

<400> SEQUENCE: 67

Met Ala Ser Ser Ala Lys Leu Leu Ser Leu Leu Leu Tyr Val Phe
  1               5                  10                 15
Ile Ser Leu Ala Ser Ser Asp Glu Ser Ile Ile Asn Asp Asn His Leu
                 20                  25                 30
Ile Leu Pro Ser Asp Arg Ser Trp Arg Thr Asp Glu Glu Val Met Ser
             35                  40                  45
Ile Tyr Leu Lys Trp Ser Leu Glu His Gly Lys Ser Asn Ser Asn Ser
 50                  55                  60
Asn Gly Ile Ile Asn Gln Gln Asp Glu Arg Phe Asn Ile Phe Lys Asp
 65                  70                  75                  80
Asn Leu Arg Phe Ile Asp Leu His Asn Glu Asn Asn Lys Asn Ala Thr
                 85                  90                  95
Tyr Lys Leu Gly Leu Thr Ile Phe Ala Asp Leu Thr Asn Asp Glu Tyr
                100                 105                 110
Arg Ser Leu Tyr Leu Gly Ala Arg Thr Glu Pro Val Arg Arg Ile Thr
            115                 120                 125
Lys Ala Lys Asn Val Asn Met Lys Tyr Ser Ala Ala Val Asn Asp Val
            130                 135                 140
Glu Val Pro Glu Thr Val Asp Trp Arg Gln Lys Gly Ala Val Asn Ala
145                 150                 155                 160
Ile Lys Asn Gln Gly Ser Cys Gly Ser Cys Trp Ala Phe Ser Thr Ala
                165                 170                 175
Ala Ala Val Glu Gly Ile Asn Lys Ile Val Thr Gly Glu Leu Ile Ser
                180                 185                 190
Leu Ser Glu Gln Glu Leu Val Asp Cys Asp Lys Ser Tyr Asn Gln Gly
            195                 200                 205
Cys Asn Gly Gly Leu Met Asp Tyr Ala Phe Gln Phe Ile Met Lys Asn
210                 215                 220
Gly Gly Leu Asn Thr Glu Gln Asp Tyr Pro Tyr His Gly Thr Asn Gly
225                 230                 235                 240
Lys Cys Asn Ser Leu Leu Lys Asn Ser Arg Val Val Thr Ile Asp Gly
                245                 250                 255
Tyr Glu Asp Val Pro Ser Lys Asp Glu Thr Ala Leu Lys Arg Ala Val
                260                 265                 270
Ser Tyr Gln Pro Val Ser Val Ala Ile Asp Ala Gly Gly Arg Ala Phe
            275                 280                 285
Gln His Tyr Gln Ser Gly Ile Phe Thr Gly Lys Cys Gly Thr Thr Met
            290                 295                 300
Asp His Ala Val Val Ala Val Gly Tyr Gly Ser Glu Asn Gly Val Asp
305                 310                 315                 320
```

```
Tyr Trp Ile Val Arg Asn Ser Trp Gly Thr Ser Trp Gly Glu Asp Gly
                325                 330                 335

Tyr Ile Arg Met Glu Arg Asn Val Ala Ser Lys Ser Gly Lys Cys Gly
                340                 345                 350

Ile Ala Ile Glu Ala Ser Tyr Pro Val Lys Tyr Ser Pro Asn Pro Val
                355                 360                 365

Arg Gly Thr Ser Ser Val
                370

<210> SEQ ID NO 68
<211> LENGTH: 374
<212> TYPE: PRT
<213> ORGANISM: Brassica napus

<400> SEQUENCE: 68

Met Ala Ser Ser Pro Lys Leu Leu Ser Leu Leu Leu Tyr Val Phe
  1               5                  10                  15

Val Ser Leu Ala Ser Gly Tyr Glu Ser Ile Ile Ser Asp Asn His Leu
                 20                  25                  30

Ser Leu Pro Ser Asp Arg Ser Trp Arg Thr Asp Glu Val Ile Ser
                 35                  40                  45

Ile Tyr Leu Arg Trp Ser Leu Glu His Gly Lys Ser Asn Ser Asn Ser
     50                  55                  60

Asn Gly Ile Ile Asn Gln Gln Asp Glu Arg Phe Asn Ile Phe Lys Asp
 65                  70                  75                  80

Asn Leu Arg Phe Ile Asp Leu His Asn Glu Asn Asn Lys Asn Ala Thr
                 85                  90                  95

Tyr Lys Leu Gly Leu Thr Ile Phe Ala Asp Leu Thr Asn Asp Glu Tyr
                100                 105                 110

Arg Ser Leu Tyr Leu Gly Ala Arg Thr Glu Pro Val Arg Arg Ile Thr
                115                 120                 125

Lys Ala Lys Asn Val Asn Met Lys Tyr Ser Ala Ala Val Asn Asp Val
    130                 135                 140

Glu Val Pro Glu Thr Val Asp Trp Arg Lys Lys Gly Ala Val Asn Ala
145                 150                 155                 160

Ile Lys Asp Gln Gly Thr Cys Gly Ser Cys Trp Ala Phe Ser Thr Ala
                165                 170                 175

Ala Ala Val Glu Gly Ile Asn Lys Ile Val Thr Gly Glu Leu Val Ser
                180                 185                 190

Leu Ser Glu Gln Glu Leu Val Asp Cys Asp Lys Ser Tyr Asn Gln Gly
            195                 200                 205

Cys Asn Gly Gly Leu Met Asp Tyr Ala Phe Gln Phe Ile Met Lys Asn
    210                 215                 220

Gly Gly Leu Asn Thr Glu Lys Asp Tyr Pro Tyr His Gly Thr Asn Gly
225                 230                 235                 240

Lys Cys Asn Ser Leu Leu Lys Asn Ser Arg Val Val Thr Ile Asp Gly
                245                 250                 255

Tyr Glu Asp Val Pro Ser Lys Asp Glu Thr Ala Leu Lys Arg Ala Val
                260                 265                 270

Ser Tyr Gln Pro Val Ser Val Ala Ile Asp Ala Gly Gly Arg Ala Phe
            275                 280                 285

Gln His Tyr Gln Ser Gly Ile Phe Thr Gly Lys Cys Gly Thr Asn Met
    290                 295                 300

Asp His Ala Val Val Ala Val Gly Tyr Gly Ser Glu Asn Gly Val Asp
305                 310                 315                 320
```

```
Tyr Trp Ile Val Arg Asn Ser Trp Gly Thr Arg Trp Glu Asp Gly
                325                 330                 335

Tyr Ile Arg Met Glu Arg Asn Val Ala Ser Lys Ser Gly Lys Cys Gly
            340                 345                 350

Ile Ala Ile Glu Ala Ser Tyr Pro Val Lys Tyr Ser Pro Asn Pro Val
            355                 360                 365

Arg Gly Thr Ser Ser Val
    370

<210> SEQ ID NO 69
<211> LENGTH: 374
<212> TYPE: PRT
<213> ORGANISM: Brassica napus

<400> SEQUENCE: 69

Met Ala Ser Ser Ala Lys Leu Leu Ser Leu Leu Leu Tyr Val Phe
  1               5                  10                  15

Ile Ser Leu Ala Ser Ser Asp Glu Ser Ile Asn Asp Asn His Leu
                20                  25                  30

Ile Leu Pro Ser Asp Arg Ser Trp Arg Thr Asp Glu Glu Val Met Ser
                35                  40                  45

Ile Tyr Leu Lys Trp Ser Leu Glu His Gly Lys Ser Asn Ser Asn Ser
 50                  55                  60

Asn Gly Ile Ile Asn Gln Gln Asp Glu Arg Phe Asn Ile Phe Lys Asp
 65                  70                  75                  80

Asn Leu Arg Phe Ile Asp Leu His Asn Glu Asn Asn Lys Asn Ala Thr
                85                  90                  95

Tyr Lys Leu Gly Leu Thr Ile Phe Ala Asp Leu Thr Asn Asp Glu Tyr
                100                 105                 110

Arg Ser Leu Tyr Leu Gly Ala Arg Thr Glu Pro Val Arg Arg Ile Thr
                115                 120                 125

Lys Ala Lys Asn Val Asn Met Lys Tyr Ser Ala Ala Val Asn Asp Val
                130                 135                 140

Glu Val Pro Glu Thr Val Asp Trp Arg Gln Lys Gly Ala Val Asn Ala
145                 150                 155                 160

Ile Lys Asn Gln Gly Ser Cys Gly Ser Cys Trp Ala Phe Ser Thr Ala
                165                 170                 175

Ala Ala Val Glu Gly Ile Asn Lys Ile Val Thr Gly Glu Leu Ile Ser
                180                 185                 190

Leu Ser Glu Gln Glu Leu Val Asp Cys Asp Lys Ser Tyr Asn Gln Gly
                195                 200                 205

Cys Asn Gly Gly Leu Met Asp Tyr Ala Phe Gln Phe Ile Met Lys Asn
                210                 215                 220

Gly Gly Leu Asn Thr Glu Gln Asp Tyr Pro Tyr His Gly Thr Asn Gly
225                 230                 235                 240

Lys Cys Asn Ser Leu Leu Lys Asn Ser Arg Val Val Thr Ile Asp Gly
                245                 250                 255

Tyr Glu Asp Val Pro Ser Lys Asp Glu Thr Ala Leu Lys Arg Ala Val
                260                 265                 270

Ser Tyr Gln Pro Val Ser Val Ala Ile Asp Ala Gly Gly Arg Ala Phe
                275                 280                 285

Gln His Tyr Gln Ser Gly Ile Phe Thr Gly Lys Cys Gly Thr Thr Met
                290                 295                 300

Asp His Ala Val Val Ala Val Gly Tyr Gly Ser Glu Asn Gly Val Asp
```

```
305                 310                 315                 320
Tyr Trp Ile Val Arg Asn Ser Trp Gly Thr Ser Trp Glu Asp Gly
                325                 330                 335

Tyr Ile Arg Met Glu Arg Asn Val Ala Ser Lys Ser Gly Lys Cys Gly
                340                 345                 350

Ile Ala Ile Glu Ala Ser Tyr Pro Val Lys Tyr Ser Pro Asn Pro Val
                355                 360                 365

Arg Gly Thr Ser Ser Val
                370

<210> SEQ ID NO 70
<211> LENGTH: 374
<212> TYPE: PRT
<213> ORGANISM: Brassica napus

<400> SEQUENCE: 70

Met Ala Ser Ser Thr Lys Leu Ile Ser Leu Leu Leu Tyr Val Val
 1               5                  10                  15

Val Ser Leu Ala Ser Gly Asp Glu Ser Thr Thr Ile Asn Asn His Leu
                20                  25                  30

Asn Leu Pro Ser Asp Gly Ser Trp Arg Thr Asp Glu Val Arg Ser
            35                  40                  45

Ile Tyr Leu Gln Trp Cys Ala Glu His Gly Lys Thr Ser Asn Asn Asn
        50                  55                  60

Gly Ile Val Asn Gln Gln Asp Glu Lys Phe Asn Ile Phe Lys Asp Asn
 65                 70                  75                  80

Leu Arg Phe Ile Asp Leu His Asn Glu Asn Asn Lys Asn Ala Thr Tyr
                85                  90                  95

Lys Leu Gly Leu Thr Ile Phe Ser Asp Leu Thr Asn Asp Glu Tyr Arg
                100                 105                 110

Arg Leu Tyr Leu Gly Ala Arg Thr Glu Ser Val Arg Ile Thr Lys
            115                 120                 125

Ala Lys Asn Val Asn Met Lys Tyr Ser Ala Ala Val Asn Asp Val Glu
        130                 135                 140

Val Pro Glu Thr Val Asp Trp Arg Arg Lys Gly Ala Val Asn Ala Ile
145                 150                 155                 160

Lys Asn Gln Gly Thr Cys Gly Ser Cys Trp Ala Phe Ser Thr Ala Ala
                165                 170                 175

Ala Val Glu Gly Ile Asn Lys Ile Val Thr Gly Glu Leu Ile Ser Leu
                180                 185                 190

Ser Glu Gln Glu Leu Val Asp Cys Asp Arg Ser Tyr Asn Gln Gly Cys
            195                 200                 205

Asn Gly Gly Leu Met Asp Tyr Ala Phe Gln Phe Ile Met Lys Asn Gly
        210                 215                 220

Gly Leu Asn Thr Glu Gln Asp Tyr Pro Tyr Arg Gly Ser Asn Gly Lys
225                 230                 235                 240

Cys Asn Ser Leu Leu Lys Asn Ser Arg Val Val Thr Ile Asp Gly Tyr
                245                 250                 255

Glu Asp Val Pro Thr Glu Asp Glu Thr Ala Leu Lys Arg Ala Val Ser
                260                 265                 270

Tyr Gln Pro Val Ser Val Ala Ile Glu Ala Gly Gly Arg Val Phe Gln
            275                 280                 285

His Tyr Gln Ser Gly Ile Phe Thr Gly Lys Cys Gly Thr Asn Leu Asp
        290                 295                 300
```

```
His Ala Val Ala Val Gly Tyr Gly Ser Glu Asn Gly Ile Asp Tyr
305                 310                 315                 320

Trp Ile Val Arg Asn Ser Trp Gly Thr Arg Trp Glu Asp Gly Tyr
                325                 330                 335

Ile Arg Met Glu Arg Asn Leu Ala Arg Ser Lys Ser Gly Lys Cys Gly
                340                 345                 350

Ile Ala Val Glu Ala Ser Tyr Pro Val Lys Tyr Ser Pro Asn Pro Val
                355                 360                 365

Arg Gly Thr Ser Ser Val
        370

<210> SEQ ID NO 71
<211> LENGTH: 1644
<212> TYPE: DNA
<213> ORGANISM: Brassica napus

<400> SEQUENCE: 71
gatctacttc ggctaaaatt acagtctcaa caactacaca agtagctcag agaatcagca      60
gaaacagttt gctacccaga agaaccctaa ttcaacaggg gagataaaaa aaagtaaaa      120
agagtacact gagagaataa ggatgatcac ctcgagtttt ctgatgaaga agggaaccaa     180
aagtgaagca tttgatgatt gtcttcttcg attgatgagc ttcttcacat ctaaaaaagt     240
atacttttttt ctctctcgat gattgatgat cagatagaag aagaaaaaga taaaccttag    300
atttttttttt gttgttcact cttcacttgg tcttctactt cttcttcttc caccttttgtt  360
tgtctctacc gttttgaatc aagcgagatt atgaaaggac aactcatcat tatcaccatt    420
gatatcttta atcctttatt tatatattta tttacccatt taatagttttt ttatgcttag    480
ttatgtattt agagaaaatta ctttatactg tttagccagg aatacatata tcagttaaac    540
aatagtgacc tgttaattac taaaatttaa taaagtagag atgtcaccga atattgtgac    600
attaataaga agcagttttc aaacctttttt agcctaccta atataacctg atattcaaac   660
ttttgatcta cgaccttatt tcaactctag tagttgtaga tacttacaaa ataaaatgtc   720
atcgatttca agtaaactaa acatgcattt acatgggaca tattctctaa tgttattata     780
ccttctgata aaacaacaat aaatgttctt agaattggaa aaatactatt ttttctaaag    840
agaaaaaggc acgttcgtat ttgctgatta ttatatacag tagtagtaaa aagtagcctt   900
tacttgtcga cagttaggta aagactgaac gccacgccac actatcttct tcttttcaac   960
agtgtgaaga tgtgttttgtt tcttttgtcac tcgttctatt ctatcatcat catcttaggt  1020
cactagccac acttatgttt tttctaaagt atacactgga agattggta aatgtatttg    1080
ataatatata tgtgattaat gatgtagtaa ttctaaaact aaagcatatt tcttggttac   1140
ttactaggta ctactactct ctggtctccg cgtgatctta tatttattat actaattgaa    1200
attaaaaagc atatactaaa aagggttaat gccataaagt cgtaagtagg tccaacaagg    1260
agtggtctta ttaacctaaa aaaggttgaa agtagctttc ttttttgctta caaaagtata   1320
tgctatgttt acatttaaca atgaatttat tgttgaccaa aaaaacaaac aatgattttat  1380
ttagctaaga gtagcatttg aattttgatt gtaatgggcc tagcctgtct ggcccaatca    1440
ttcataaccg ggtctaatca ttaataaaaa gcccttcagc attcaacgct aaacgcttat    1500
tacaaacgct agccgcgcgt tttgtaaacg ttgttgcatc cttactggct aaagtctcct    1560
tattactagg acaaactatc taatccacga cgacgaccaa acaaaagctc ttcttgttttt  1620
ggtttccctg taagaaaaga aatg                                             1644
```

<210> SEQ ID NO 72
<211> LENGTH: 3997
<212> TYPE: DNA
<213> ORGANISM: Brassica napus

<400> SEQUENCE: 72

```
aagcttgatg gggttgtgat gtttgcggat gatagtaaca tgcatagtat ggagtttttc      60
gatgagattc agaacgtgaa gtggttcggt gctgtttccg ttgggatatt agcgcattcg     120
gggaatgcgg aagagatggt tatgtcgatg gataagagaa gagagatgga ggaagaagag     180
agctcttcgt tatcttcgtt accagtacaa ggtcctgcgt gtaacgcgac cgataagctg     240
atcggttggc atgttttcaa tacgttgcca tacgcgggga agagtgcggt ttacatagac     300
gatgtagctg cggttttgcc gcagaagctg gagtggtgtg ggtttgtatt gaactcgagg     360
attctttggg atgaggctga gagtaagccg gagtgggtta aggagtttgg gttgttgaac     420
gagaacgaag gcgtggagag tcctttgtct ctgttgaatg atccttcgat ggttgagcct     480
cttggaagct gtggaagaca ggttctgctt tggtggcttc gtgtcgaagc acgcgctgat     540
agcaagttcc ctcccgggta tatgccttct tttgctctca agatgttaac taattagctc     600
aatgttcaaa ctaggagtta gttagtgatg tttggttctg tttttgttat atgagtgcag     660
atgggtgatt gatcctccgt tagaaatcac agtggcggct aaacgaacgc catggccaga     720
tgttccacct gagccaccta ctaaaaagaa agatcaaatg tcattatccc aaggcaacaa     780
caacgtggtg gtgataccga agcaccagca gcagcagcag caacagcaac gttctagcaa     840
agtgcggaaa ccgaaacgca gaagtaagag aaataaacac gaagctaaac caactgatac     900
gacaacacaa gtttcttctt ccactaaaca tcatcaagaa agaaactgag gaagaagaaa     960
gatcatttct actattttat tatcattcat ttgtttgcca agttttata gagaaatgtc    1020
aagagatcat cttattctcc tccagatacc gcgaatagta agaatcaacg gtgaggaagc    1080
aagaacaaag gcttagattt tatgatgatg gagcccccac agcaaagggg tatcgggtt    1140
tttaggggaa ttgatgatca ttcgtttatt ttcgatatat cttctttttg gtctttataa    1200
gaacttatct gtattagtaa caaagaatta tttgtttcat tgttcttgaa gttgcaaaaa    1260
aaggcttaga aacaaaaact ttgggttgta tagtttcttt tgtaagcata tttctcaatc    1320
catttctgtt ttatccccca attaatccac actatggacc taaaagttca aagcctcaat    1380
ttactcctgc gagttcgttt cacagaaatt aattacactt ttttattatt ttcataagg    1440
aaacaataca tatgtattta tatagtattt tctaaagaaa tattggagat gaagacattg    1500
gaaaagatac cttcgtaaaa aagaattgtg aagaaagtaa atacaaaaca gaatcattct    1560
tttgtgaaag ttgagacaaa gactgaaaac agattcataa ctgaaataat ggaggattgg    1620
gcggttttgt cagaacatca catgtcttct ttaaccactt ttccctcact ctattagatt    1680
tttttcttag tacactgcgg tcatagccta taggtatgta ctttgaccac tataaacagg    1740
attgagttag ggtttcttct aattatggga ttttattacg ttttcaacct ctatttctt    1800
cggattaggt ttatttagat gttttttgct tcatttcttt aactatttag ttttagagag    1860
gaaacacaag atgttaaacc cattagtgaa ccaaaattta agcaggtgac tagagtaaac    1920
caaacatatc taatagtatg gaattttgtc tttactactt aatatgaggt aatcaatccg    1980
gatagaagtg aaattaacga aaatatcct atttatatgt ttacttataa aatcaaattt    2040
atattatgcg attttaaca ttctttggaa cagtattagt tcagttgctt aaacgaaaac    2100
caaacagtcg gtggaactcc catgcttcgt agcttagctg cccatacwaa acgatatcaa    2160
```

-continued

```
aaccaaaccg aattataaaa cagaaacggt cacctttagt tgtaccatgt cagaaacacg    2220
agcgaggcac ttgtgtttct taaaccttat caaaagccac cactccggat tgaaacttgg    2280
ttaaagacaa ctctttgcct cccatttcct ccaatcacct ttttttcttg ttgttaaaat    2340
gtcttcataa agtatgctcg tatgagaaag gatcaaatgc aacggtcagg atggggcacc    2400
gcctcgtgac aagaggatct gccgtgaaac tggaacatca tgtccaccca ttcattctag    2460
attcttctat atgaatcttc aactttaata tatctattaa atatacatgc agagctctgt    2520
acgtatattt attatttata tcatcaacta taaaaaaaaa gaccacgcat aatagaaact    2580
atattcagac tacagttttg aatcataatg taaatatata gaggaataat attcctcata    2640
ttttgataaa atagattatt ttccactcac cagaaagaca gaaccatatt ttctagtggt    2700
cgatatatag aatgtaaata tattgtattt actaaaagct atcattctat atatgtatct    2760
ttaaacaaaa aatttagata ggttttccca tacgtacgta ccttatgaaa cttttcgag     2820 gtagttgcaa ctcttctatt cattgttttt ccttcgtccc atatatatag attattggaa    2880
attgatgtaa cgtagattca gaaattcaca tcacagacat ctatacctat ttatacggct    2940
ctcaaaccat aattgtcaca atgcatgtct gtggatttaa ctttacaact tactaaatac    3000
tccaattaga ttcgacgtaa agaaattaat cacacgaaaa agatgcagct atttcgttaa    3060
aagttgatcc tcaagtgaca tcatgctgct tcgaaatgct gaaaagattt aatgatcttc    3120
atgttcccat gtgttcggaa ttgaacgact ctgatgatat gtggtcggta gccaaaaaaa    3180
acgcggttca aagcgaattg tttgttttgc tatatactat tgacgttata aagtcaaaaa    3240
taaaccgctt acaagatggt tctgaccgct tcaaaaataa acgctctgtg tatatatatt    3300
atcgtctact gtatgcagga tatatggtag ctatttacgt caaatatgag tagatcagcg    3360
ttgatcaaac ataaacgtaa atctctcgtg agtcgataga tgttgatgta aacaacaaac    3420
cacggaaaat aaataactgc aaaaaatata aaagaatgg tgttattatt taacccaaaa    3480
attgtattat catacttaca cgaagaaaat tacgtacatc tacgagataa ttccatgaga    3540
aaagaatagt aaactctttg aattacagac gaatggtttg aaccccgtag atctttgagt    3600
ttgaattgta tttaagagca tgatactacg atgttgtatt ctttttttaga tcagtgaatc    3660 gtagtttttt cctatttacc atccgattgt ccgaataaaa taataattat ctccaaaatt    3720
aataaattta gatttctaaa atcaaacata aatatctagt aattaaaagt gaagatatta    3780
tatatttagt aaacagttgt ccatatttcg gcaaaaaaaa tccatttgaa acgtccacta    3840
tcttgcatgc ccattattac ttttttattat aataccaact tgaaatatta aaataccaa     3900 actttggtta taaatagttt cacattcttg tcccaccaaa aatcaagcca taccaactat    3960
caaaactaga aaccaacaa aacaaacata caatatg                               3997
```

<210> SEQ ID NO 73
<211> LENGTH: 2000
<212> TYPE: DNA
<213> ORGANISM: Brassica napus

<400> SEQUENCE: 73

```
ggatcccaca cataactgta atgtttcaat actcacgtgt aactttgatc atcgaaacct      60
atttagtaaa atccgcattc tggcccaata aaacttataa gtgggctaaa tctcttttgt     120
atgtatctag gattttttata gtactatgtc tccaccgata aaccgaagcg ttacccttt     180 agcttatcaa aaaaaattct gaaactttt attttcacct ctctatatct ccaacgatca     240
```

```
gttatggtac cgtttcacct ctgaaacgat ccgtctcagt atatataatt cctcaaacaa      300
accttgaaac ccatatctct tattaaatta ctcctaaatt gaattgtcgc ggcttttagc      360
caaccttcga agatgtcagc ctccagtgtt gttgttgctt aatcggtcgt tgtccccgcc      420
acctttcttc gcctagaaca tagtacccag gaaaaggtat tgacaatttg actttctatg      480
gaatactatg taccatattt gtttaatcaa tattcaagct atcagttttta atacttcaag      540 cgtatgtttc tctgggcaga attctgagat ccacggttct atcccagttc ttgtgaatca      600
ctaccatcca tcgctacgat aggggtcga ttgtgaaagt tgattgatcg ctttgaagtt       660
gtccgattaa ctaatatgat gtaaactctg ttctgatgag ctaaacggaa aagttatttg      720
gttgctatga ctaacagagg ctgcaaggct tggtacgtct caggcggagc tgaaggacgg      780
tacaactaga gcgcctattg tctggttttt gtcgtgccaa cgtgctatga aacttaagcc      840
ttccttggag aatccagatc acttcgaaac gtcggctgtc attttcaaca ggtaccacca      900
tgatgtaaat ttttttatgt ttgtggtgtg gttcggctca agattgaaac ttttgctgat      960
gaaataatga ttttgtggat gcatgacaat tagatttacg agtctacaaa ctgttcattg      1020
tacattggca gagaaaaaat ggctatgtat ggttcagttg taacaccggt gtggtgcaat      1080
gaggatggac atggtaacca aaggtgtgca taatgttatt gatttcctca gcgatgattc      1140
ccctaacatg gatgtgatcg gaatctctgg tgagtttctt ttgtatgtta ttggttttgat     1200 tttaaaacaa tgtctttttag catagtatca tcttgagact taaaaacttg aaatttattg     1260
gtcagataac ttattctccg acattaataa acctgctgcg gtgaactgca tcgagggaca     1320
tggcagtaat tagaagagag atagggaata aggtgttgaa aacgagtgtg tctggcttgg     1380
tggagctcaa tatactcaag aacctcaccg tctatgttgt tgcaggctct ctaggtcgat     1440
tcaaatctca tgccagcaac atagtgtttg atgtattcat agctacttgc caagatccag     1500
cccaaaacat ggagagctct caaattgatg gaagccatta atagcaatca ccgtaccttc     1560
actatctcca ccatcactga agataccatc atagagaact atggaaaaat cgtctaatta     1620
tacttgggta tatattatag atcagcaaac cgtatttatt gttatcttga tagttgatat     1680
agtatataag taactaaatt ttctgaaatt attagaaaat acataaatat ctccctgcct     1740
attatcacac aacgttctta cgtggggaat gaagatattt aaggtgtaaa attaatttca     1800
ttcatatttc cggcaatatc catttgaacc gtccaccatc ttgcatgccc attactgcat     1860
tttattataa tagaaaagta taccaacttg aaatattaaa actccaagaa tttggttata     1920
aatagctcct ctcagcctcc aacgaaatca agccatatca actatcagaa ctagaacaac     1980
caagccaaac atacaatatg                                                 2000
```

<210> SEQ ID NO 74
<211> LENGTH: 8
<212> TYPE: PRT
<213> ORGANISM: Artificial Sequence
<220> FEATURE:
<221> NAME/KEY: SITE
<222> LOCATION: (8)
<223> OTHER INFORMATION: Xaa is Asn or Glu or Asp
<220> FEATURE:
<223> OTHER INFORMATION: Description of Artificial Sequence: Motif

<400> SEQUENCE: 74

Gly Cys Asn Cys Cys Leu Met Xaa
 1               5

<210> SEQ ID NO 75

```
<211> LENGTH: 507
<212> TYPE: DNA
<213> ORGANISM: Artificial Sequence
<220> FEATURE:
<221> NAME/KEY: misc_feature
<222> LOCATION: (1)..(5), 10, 13, 15, 16, 28, 150, 276, 285, 292, 312,
      337
<223> OTHER INFORMATION: n is uncertain
<220> FEATURE:
<221> NAME/KEY: misc_feature
<222> LOCATION: 355, 357, 447, 477, 495
<223> OTHER INFORMATION: n is uncertain
<220> FEATURE:
<223> OTHER INFORMATION: Description of Artificial Sequence: Consensus

<400> SEQUENCE: 75
nnnnncaacn ggngnntgat ggactatnct tttcaattca tcatgaaaaa cggcggtttg      60
aacaccgagc aagattatcc ttaccgtggt tccaatggca caaaatgcaa ttctttactg     120
aagaattcaa gagttgtaac tattgatggn tacgaagatg ttcctactaa agatgaaacc     180
gccttgaaga gagcagtttc ataccagcct gtgagtgttg ctattgatgc tggtggaaga     240
gctttccaac attaccaatc gggaatcttc actggnaagt gtggnacaaa tntggatcac     300
gcagtggtgg cngttggtta tggttcagag aacggtnttg actattggat tgtangnaac     360
tcttggggta cacgttgggg agaggatggt tacattagga tggagagaaa cgtggcaagg     420
tctaaatccg gtaagtgtgg gattgcnata gaagcctcgt atccggttaa gtacagncca     480
aacccggttc gtggnaccag cagtgtt                                         507

<210> SEQ ID NO 76
<211> LENGTH: 255
<212> TYPE: DNA
<213> ORGANISM: Artificial Sequence
<220> FEATURE:
<221> NAME/KEY: misc_feature
<222> LOCATION: 10..13, 17, 18, 21, 30, 38, 45, 47, 55..58, 60, 67, 68,
      95..97
<223> OTHER INFORMATION: n is uncertain
<220> FEATURE:
<221> NAME/KEY: misc_feature
<222> LOCATION: 117, 125, 141, 142, 146, 147, 153, 155, 170, 173,
      180..182
<223> OTHER INFORMATION: n is uncertain
<220> FEATURE:
<221> NAME/KEY: misc_feature
<222> LOCATION: 185, 186, 196, 213
<223> OTHER INFORMATION: n is uncertain
<220> FEATURE:
<223> OTHER INFORMATION: Description of Artificial Sequence: Consensus

<400> SEQUENCE: 76
tgaagttgtn nnaaaannaa nctcatgcan taatcaantt gggantntta taacnnnnan      60
taatctnnta ttattgtttg tatgtatagt atttnnnaaa aagaaggta tttgatncac      120 catanggatt taatctgtat nnatcnntat gtngntcaaa tatcatttcn ttaaaagaan     180
nnttnntttg gcttgnttat gtattaagag aantataata aaaatgatat atttctctta     240
acagcaaaaa aaaaa                                                     255

<210> SEQ ID NO 77
<211> LENGTH: 206
<212> TYPE: PRT
<213> ORGANISM: Brassica napus

<400> SEQUENCE: 77

Ser Cys Trp Ala Phe Ser Thr Ala Ala Ala Val Glu Gly Ile Asn Lys
 1               5                  10                  15
```

```
Ile Val Thr Gly Glu Leu Val Ser Leu Ser Glu Gln Glu Leu Val Asp
            20                  25                  30

Cys Asp Lys Ser Tyr Asn Gln Gly Cys Asn Gly Gly Leu Met Asp Tyr
            35                  40                  45

Ala Phe Gln Phe Ile Met Lys Asn Gly Gly Leu Asn Thr Glu Lys Asp
            50                  55                  60

Tyr Pro Tyr His Gly Thr Asn Gly Lys Cys Asn Ser Leu Leu Lys Asn
 65              70                  75                       80

Ser Arg Val Val Thr Ile Asp Gly Tyr Glu Asp Val Pro Ser Lys Asp
            85                  90                  95

Glu Thr Ala Leu Lys Arg Ala Val Ser Tyr Gln Pro Val Ser Val Ala
            100                 105                 110

Ile Asp Ala Gly Gly Arg Ala Phe Gln His Tyr Gln Ser Gly Ile Phe
            115                 120                 125

Thr Gly Lys Cys Gly Thr Asn Met Asp His Ala Val Ala Val Gly
            130                 135                 140

Tyr Gly Ser Glu Asn Gly Val Asp Tyr Trp Ile Val Arg Asn Ser Trp
145                 150                 155                 160

Gly Thr Arg Trp Gly Glu Asp Gly Tyr Ile Arg Met Glu Arg Asn Val
                165                 170                 175

Ala Ser Lys Ser Gly Lys Cys Gly Ile Ala Ile Glu Ala Ser Tyr Pro
                180                 185                 190

Val Lys Tyr Ser Pro Asn Pro Val Arg Gly Thr Ser Ser Val
                195                 200                 205

<210> SEQ ID NO 78
<211> LENGTH: 202
<212> TYPE: PRT
<213> ORGANISM: Artificial Sequence
<220> FEATURE:
<221> NAME/KEY: SITE
<222> LOCATION: 40, 41, 43, 44, 49, 61, 133
<223> OTHER INFORMATION: Xaa is uncertain
<220> FEATURE:
<223> OTHER INFORMATION: Description of Artificial Sequence: Consensus

<400> SEQUENCE: 78

Ser Cys Trp Ala Phe Ser Thr Ala Ala Val Glu Gly Ile Asn Lys
 1               5                  10                  15

Ile Val Thr Gly Glu Leu Val Ser Leu Ser Glu Gln Glu Leu Val Asp
            20                  25                  30

Cys Asp Lys Ser Tyr Asn Gln Xaa Xaa Asn Xaa Xaa Leu Met Asp Tyr
            35                  40                  45

Xaa Phe Gln Phe Ile Met Lys Asn Gly Gly Ile Glu Xaa Asp Tyr Pro
 50                  55                  60

Tyr Gln Arg Gly Ser Asn Gly Lys Cys Asn Ser Leu Leu Lys Asn Ser
 65              70                  75                       80

Arg Val Val Thr Ile Asp Gly Tyr Glu Asp Val Pro Ser Lys Asp Glu
            85                  90                  95

Thr Ala Leu Lys Arg Ala Val Ser Tyr Gln Pro Val Ser Val Ala Ile
            100                 105                 110

Asp Ala Gly Gly Arg Ala His Tyr Gln Ser Gly Ile Phe Thr Gly Lys
            115                 120                 125

Cys Gly Thr Asn Xaa Asp His Ala Val Val Ala Val Gly Tyr Gly Ser
            130                 135                 140

Glu Asn Gly Val Asp Tyr Trp Ile Val Arg Asn Ser Trp Gly Thr Arg
```

```
                145                 150                 155                 160
Trp Gly Glu Asp Gly Tyr Ile Arg Met Glu Arg Asn Leu Val Ala Ser
                165                 170                 175

Lys Lys Cys Gly Ile Ala Ile Glu Ala Ser Tyr Pro Val Lys Tyr Ser
                180                 185                 190

Pro Asn Pro Val Arg Gly Thr Ser Ser Val
            195                 200
```

<210> SEQ ID NO 79
<211> LENGTH: 189
<212> TYPE: PRT
<213> ORGANISM: Brassica napus

<400> SEQUENCE: 79

```
Met Ser Ile Tyr Leu Arg Trp Ser Leu Glu His Gly Lys Ser Asn Ser
  1               5                  10                  15

Asn Ser Asn Gly Ile Ile Asn Gln Gln Asp Glu Arg Phe Asn Ile Phe
             20                  25                  30

Lys Asp Asn Leu Arg Phe Ile Asp Leu His Asn Glu Asn Asn Lys Asn
         35                  40                  45

Ala Thr Tyr Lys Leu Gly Leu Thr Ile Phe Ala Asn Leu Thr Asn Asp
     50                  55                  60

Glu Tyr Arg Ser Leu Tyr Leu Gly Ala Arg Thr Glu Pro Val Arg Arg
 65                  70                  75                  80

Ile Thr Lys Ala Lys Asn Val Asn Met Lys Tyr Ser Ala Ala Val Asn
                 85                  90                  95

Val Asp Glu Val Pro Val Thr Val Asp Trp Arg Gln Lys Gly Ala Val
            100                 105                 110

Asn Ala Ile Lys Asp Gln Gly Thr Cys Gly Ser Cys Trp Ala Phe Ser
        115                 120                 125

Thr Ala Ala Ala Val Glu Gly Ile Asn Lys Ile Val Thr Gly Glu Leu
    130                 135                 140

Val Ser Leu Ser Glu Gln Glu Leu Val Asp Cys Asp Lys Ser Tyr Asn
145                 150                 155                 160

Gln Gly Cys Asn Gly Gly Leu Met Asp Tyr Ala Phe Gln Phe Ile Met
                165                 170                 175

Lys Asn Gly Gly Leu Asn Thr Glu Lys Asp Tyr Pro Tyr
            180                 185
```

<210> SEQ ID NO 80
<211> LENGTH: 244
<212> TYPE: PRT
<213> ORGANISM: Artificial Sequence
<220> FEATURE:
<221> NAME/KEY: SITE
<222> LOCATION: 56, 135, 136, 140, 152, 163
<223> OTHER INFORMATION: Xaa is uncertain
<220> FEATURE:
<223> OTHER INFORMATION: Description of Artificial Sequence: Consensus

<400> SEQUENCE: 80

```
Arg Lys Pro Thr Lys Gln Thr Tyr Asn Met Ala Ser Ser Pro Lys Leu
  1               5                  10                  15

Leu Ser Leu Leu Leu Leu Tyr Val Phe Val Ser Leu Ala Ser Gly Tyr
             20                  25                  30

Glu Ser Ile Ile Ser Asp Asn His Leu Ser Leu Pro Ser Asp Arg Ser
         35                  40                  45

Trp Arg Thr Asp Glu Glu Val Xaa Ser Ile Tyr Leu Arg Trp Ser Leu
```

```
                50                  55                  60
Glu His Gly Lys Ser Asn Ser Asn Ser Asn Gly Ile Ile Asn Gln Gln
 65                  70                  75                  80

Asp Glu Arg Phe Asn Ile Phe Lys Asp Asn Leu Arg Phe Ile Asp Leu
                 85                  90                  95

His Asn Glu Asn Asn Lys Asn Ala Thr Tyr Lys Leu Gly Leu Thr Ile
                100                 105                 110

Phe Ala Asp Leu Thr Asn Asp Glu Tyr Arg Ser Leu Tyr Leu Gly Ala
                115                 120                 125

Arg Thr Glu Pro Val Arg Xaa Xaa Thr Lys Ala Xaa Asn Val Asn Met
130                 135                 140

Lys Tyr Ser Ala Ala Val Asn Xaa Val Glu Val Pro Glu Thr Val Asp
145                 150                 155                 160

Trp Arg Xaa Lys Gly Ala Val Asn Ala Ile Lys Asp Gln Gly Thr Cys
                165                 170                 175

Gly Ser Cys Trp Ala Phe Ser Thr Ala Ala Ala Val Glu Gly Ile Asn
                180                 185                 190

Lys Ile Val Thr Gly Glu Leu Val Ser Leu Ser Glu Gln Glu Leu Val
                195                 200                 205

Asp Cys Asp Lys Ser Tyr Asn Gln Gly Cys Asn Gly Gly Leu Met Asp
                210                 215                 220

Tyr Ala Phe Gln Phe Ile Met Lys Asn Gly Gly Leu Asn Thr Glu Lys
225                 230                 235                 240

Asp Tyr Pro Tyr
```

<210> SEQ ID NO 81
<211> LENGTH: 305
<212> TYPE: DNA
<213> ORGANISM: Artificial Sequence
<220> FEATURE:
<221> NAME/KEY: misc_feature
<222> LOCATION: 45, 96, 248
<223> OTHER INFORMATION: n is uncertain
<220> FEATURE:
<223> OTHER INFORMATION: Description of Artificial Sequence: Consensus

<400> SEQUENCE: 81

```
aaactagaaa accaacaaaa caaacataca atatggcttc gtcancgaaa ctcctctctt    60
tacttctctt gtacgtcttc atttcattag cctccngtga tgagtccatc atcaacgaca   120
accatctcat tcttccatct gaccgctcgt ggagaaccga tgaagaagtg atgtccatct   180
acttaaaatg gtccttggag cacgggaaaa gtaacagcaa cagcaacggt attatcaacc   240
aacaaganga aagattcaat attttcaaag acaacctaag attcatcgat ctacacaacg   300
agaac                                                               305
```

<210> SEQ ID NO 82
<211> LENGTH: 1661
<212> TYPE: DNA
<213> ORGANISM: Artificial Sequence
<220> FEATURE:
<221> NAME/KEY: misc_feature
<222> LOCATION: 4..10, 12, 90, 428, 775, 776, 1079..1081, 1134,
      1148..1165
<223> OTHER INFORMATION: n is uncertain
<220> FEATURE:
<221> NAME/KEY: misc_feature
<222> LOCATION: 1172, 1180, 1191..1198, 1213..1226, 1250..1253, 1274,
      1277
<223> OTHER INFORMATION: n is uncertain
<220> FEATURE:

```
<221> NAME/KEY: misc_feature
<222> LOCATION: 1279..1282, 1291..1303, 1322..1325, 1339, 1340,
      1345..1348
<223> OTHER INFORMATION: n is uncertain
<220> FEATURE:
<221> NAME/KEY: misc_feature
<222> LOCATION: 1357..1371, 1391..1410, 1420, 1427..1435, 1448..1453,
      1459..1464
<223> OTHER INFORMATION: n is uncertain
<220> FEATURE:
<221> NAME/KEY: misc_feature
<222> LOCATION: 1487, 1501..1504, 1512, 1513, 1529..1538, 1546..1550,
      1556
<223> OTHER INFORMATION: n is uncertain
<220> FEATURE:
<221> NAME/KEY: misc_feature
<222> LOCATION: 1558..1562, 1564..1566, 1568, 1570, 1574..1579, 1582,
      1583, 1586
<223> OTHER INFORMATION: n is uncertain
<220> FEATURE:
<221> NAME/KEY: misc_feature
<222> LOCATION: 1590..1594, 1615, 1638..1647
<223> OTHER INFORMATION: n is uncertain
<220> FEATURE:
<223> OTHER INFORMATION: Description of Artificial Sequence: Majority

<400> SEQUENCE: 82
caannnnnnn anctagaaaa ccaacaaaac aaacatacaa tatggcttcg tcatcgaaac        60
tcctttcttt acttctctta tacgtcttcn tttcattagc ctccagttat gagtccatta      120
tcagcgacaa ccatctcaat cttccatctg accgctcgtg gagaaccgat gaagaagtga      180
tgtccatcta cttaaaatgg tccttggagc acgggaaaaa taacagcaac agcaacggta      240
ttatcaacca acaagacgaa agattcaata ttttcaaaga caacctaaga ttcatcgatc      300
tacacaacga gaacaacaag aacgctactt acaagcttgg tctaaccata ttcgctgatc      360
tcactaacga tgagtaccgg agtttatacc tcggggcaag aaccgagcct gtccgccgca      420
tcactaangg ccaagaacgt taacatgaaa tactcagccg cagtaaacga cgtggaggtt      480
ccggagacgg ttgactggag acagaaagga gccgttaatg ccattaaaga ccaaggaact      540
tgcggaagtt gttgggcgtt ttcaacagct gcagcagtag aaggtataaa caagatcgta      600
acaggagaac tcatatctct gtccgaacaa gaacttgtcg actgcgacaa atcatacaac      660
caaggctgta acggcggtct aatggattat gcttttcaat tcatcatgaa aaacggcgga      720
ttaaacaccg agaaagacta tccttaccac ggaaccaatg gcaaatgcaa ctctnnttac      780
ttaaaaattc aagagttgtg actatcgatg gatacgaaga tgttcctagt aaagatgaaa      840
ccgcgttgaa gagagcagtt tcgtaccagc ctgtgagtgt tgctattgat gctggtggaa      900
gagctttcca acattaccaa tctggaatct tcactggaaa gtgtggtacg actatggatc      960
acgctgtggt ggcggttggt tatggttcag agaacggtgt tgactattgg attgtacgta     1020
actcttgggg tacaagttgg ggagaggatg gttacattag gatggagaga aacgtggcnn     1080
ngtccaaatc cggtaagtgt gggattgcga ttgaagcctc gtatccggtt aagntacagc     1140
ccaaaccnnn nnnnnnnnnn nnnncggtt cngtggaacn cagcagtgtt nnnnnnnntg     1200
aagttaacaa aannnnnnnn nnnnnnagaa tctcatgcag taatcaaatn nnntgggatt     1260
gttataagtt aaanttnann nnatcttgta nnnnnnnnnn nnnttattgt ttgtatgtat     1320
annnngtatt tcgtaaaann aaaannnntt gattcannnn nnnnnnnnnn nccataggga     1380
tttaatctgt nnnnnnnnnn nnnnnnnnnn ataaatctcn tatgttnnnn nnnnnggtca     1440
antatcannn nnntttcann nnnnttcaaa gaatatttgt ctttggnctt gtttatgtat     1500
nnnntaagag annaatataa taaaactgnn nnnnnnnnat atattnnnnn tctctnannn     1560
```

```
nnannnanan aaannnnnna annaanaaan nnnnaacagc agganacaat aaaaaaaaaa    1620
aaaaaaaaaa aaaaaaannn nnnnnnnaaa aaaaaaaaaa a                        1661
```

<210> SEQ ID NO 83
<211> LENGTH: 467
<212> TYPE: PRT
<213> ORGANISM: Artificial Sequence
<220> FEATURE:
<221> NAME/KEY: SITE
<222> LOCATION: 28, 346, 375..465, 467
<223> OTHER INFORMATION: Xaa is uncertain
<220> FEATURE:
<223> OTHER INFORMATION: Description of Artificial Sequence: Majority

<400> SEQUENCE: 83

```
Met Ala Ser Ser Ala Lys Leu Leu Ser Leu Leu Leu Tyr Val Phe
 1               5                  10                  15

Val Ser Leu Ala Ser Ser Asp Glu Ser Ile Ile Xaa Asp Asn His Leu
             20                  25                  30

Ser Leu Pro Ser Asp Arg Ser Trp Arg Thr Asp Glu Glu Val Ser Ser
         35                  40                  45

Ile Tyr Leu Ala Trp Ser Leu Glu His Gly Lys Ser Asn Ser Asn Ser
 50                  55                  60

Asn Gly Ile Ile Asn Gln Gln Asp Glu Arg Phe Asn Ile Phe Lys Asp
 65                  70                  75                  80

Asn Leu Arg Phe Ile Asp Leu His Asn Glu Asn Asn Lys Asn Ala Thr
                 85                  90                  95

Tyr Lys Leu Gly Leu Thr Ile Phe Ala Asp Leu Thr Asn Asp Glu Tyr
            100                 105                 110

Arg Ser Leu Tyr Leu Gly Ala Arg Thr Glu Pro Val Arg Arg Ile Thr
        115                 120                 125

Lys Ala Lys Asn Val Asn Met Lys Tyr Ser Ala Ala Val Asn Asp Val
130                 135                 140

Glu Val Pro Glu Thr Val Asp Trp Arg Gln Lys Gly Ala Val Asn Ala
145                 150                 155                 160

Ile Lys Asp Gln Gly Ser Cys Gly Ser Cys Trp Ala Phe Ser Thr Ala
                165                 170                 175

Ala Ala Val Glu Gly Ile Asn Lys Ile Val Thr Gly Glu Leu Ile Ser
            180                 185                 190

Leu Ser Glu Gln Glu Leu Val Asp Cys Asp Lys Ser Tyr Asn Gln Gly
        195                 200                 205

Cys Asn Gly Gly Leu Met Asp Tyr Ala Phe Gln Phe Ile Met Lys Asn
210                 215                 220

Gly Gly Leu Asn Thr Glu Lys Asp Tyr Pro Tyr His Gly Thr Asn Gly
225                 230                 235                 240

Lys Cys Asn Ser Leu Leu Lys Asn Ser Arg Val Val Thr Ile Asp Gly
                245                 250                 255

Tyr Glu Asp Val Pro Ser Lys Asp Glu Thr Ala Leu Lys Arg Ala Val
            260                 265                 270

Ser Tyr Gln Pro Val Ser Val Ala Ile Asp Ala Gly Gly Arg Ala Phe
        275                 280                 285

Gln His Tyr Gln Ser Gly Ile Phe Thr Gly Lys Cys Gly Thr Asn Met
290                 295                 300

Asp His Ala Val Val Ala Val Gly Tyr Gly Ser Glu Asn Gly Val Asp
305                 310                 315                 320
```

```
Tyr Trp Ile Val Arg Asn Ser Trp Gly Thr Ser Trp Gly Glu Asp Gly
                325                 330                 335

Tyr Ile Arg Met Glu Arg Asn Val Ala Xaa Ser Lys Ser Gly Lys Cys
            340                 345                 350

Gly Ile Ala Ile Glu Ala Ser Tyr Pro Val Lys Tyr Ser Pro Asn Pro
                355                 360                 365

Val Arg Gly Thr Ser Ser Xaa Xaa Xaa Xaa Xaa Xaa Xaa Xaa Xaa Xaa
        370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
                420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
        450                 455                 460

Xaa Val Xaa
465

<210> SEQ ID NO 84
<211> LENGTH: 328
<212> TYPE: PRT
<213> ORGANISM: Brassica napus

<400> SEQUENCE: 84

Met Ser Ile Tyr Leu Arg Trp Ser Leu Glu His Gly Lys Ser Asn Ser
  1               5                  10                  15

Asn Ser Asn Gly Ile Ile Asn Gln Gln Asp Glu Arg Phe Asn Ile Phe
                 20                  25                  30

Lys Asp Asn Leu Arg Phe Ile Asp Leu His Asn Glu Asn Asn Lys Asn
             35                  40                  45

Ala Thr Tyr Lys Leu Gly Leu Thr Ile Phe Ala Asn Leu Thr Asn Asp
         50                  55                  60

Glu Tyr Arg Ser Leu Tyr Leu Gly Ala Arg Thr Glu Pro Val Arg Arg
 65                  70                  75                  80

Ile Thr Lys Ala Lys Asn Val Asn Met Lys Tyr Ser Ala Ala Val Asn
                 85                  90                  95

Val Asp Glu Val Pro Val Thr Val Asp Trp Arg Gln Lys Gly Ala Val
            100                 105                 110

Asn Ala Ile Lys Asp Gln Gly Thr Cys Gly Ser Cys Trp Ala Phe Ser
        115                 120                 125

Thr Ala Ala Val Glu Gly Ile Asn Lys Ile Val Thr Gly Glu Leu
130                 135                 140

Val Ser Leu Ser Glu Gln Glu Leu Val Asp Cys Asp Lys Ser Tyr Asn
145                 150                 155                 160

Gln Gly Cys Asn Gly Gly Leu Met Asp Tyr Ala Phe Gln Phe Ile Met
                165                 170                 175

Lys Asn Gly Gly Leu Asn Thr Glu Lys Asp Tyr Pro Tyr His Gly Thr
            180                 185                 190

Asn Gly Lys Cys Asn Ser Leu Leu Lys Asn Ser Arg Val Val Thr Ile
        195                 200                 205

Asp Gly Tyr Glu Asp Val Pro Ser Lys Asp Glu Thr Ala Leu Lys Arg
    210                 215                 220
```

```
Ala Val Ser Tyr Gln Pro Val Ser Val Ala Ile Asp Ala Gly Gly Arg
225                 230                 235                 240

Ala Phe Gln His Tyr Gln Ser Gly Ile Phe Thr Gly Lys Cys Gly Thr
            245                 250                 255

Asn Met Asp His Ala Val Val Ala Val Gly Tyr Gly Ser Glu Asn Gly
        260                 265                 270

Val Asp Tyr Trp Ile Val Arg Asn Ser Trp Thr Arg Trp Gly Glu
    275                 280                 285

Asp Gly Tyr Ile Arg Met Glu Arg Asn Val Ala Ser Lys Ser Gly Lys
    290                 295                 300

Cys Gly Ile Ala Ile Glu Ala Ser Tyr Pro Val Lys Tyr Ser Pro Asn
305                 310                 315                 320

Pro Val Arg Gly Thr Ser Ser Val
                325
```

```
<210> SEQ ID NO 85
<211> LENGTH: 137
<212> TYPE: DNA
<213> ORGANISM: Brassica napus

<400> SEQUENCE: 85
tgatgtccat ctacttaaga tggtccttgg agcacgggaa aagtaacagc aacagcaacg      60
gtattatcaa ccaacaagac gaaagattca ataatttcaa agacaaccta agattcatcg     120
atctacacaa ccagaac                                                    137

<210> SEQ ID NO 86
<211> LENGTH: 1102
<212> TYPE: DNA
<213> ORGANISM: Brassica napus

<400> SEQUENCE: 86
tgatgtccat ctacttaaga tggtccttgg agcacgggaa aagtaacagc aacagcaacg      60
gtattatcaa ccaacaagac gaaagattca ataatttcaa agacaaccta agattcatcg     120
atctacacaa cgagaacaac aagaacgcta cttacaagct tggtctaacc atattcgcta    180
atctcactaa cgatcactac cggagtttat acctcggggc aagaaccgag cctgtccgcc    240
gcatcactaa ggccaagaac gttaacatga atactcagc cgcactaaac gacgtggagg     300
ttccggtgac ggttgactgg agacagaaag gagccgttaa tgccattaaa gaccaaggaa    360
cttgcggaag ttgttgggcg ttttcaacag ctgcagcagt agaaggtata acaagatcg     420
taacaggaga actcgtatct tgtccgaaca agaacttgt cgactgcgac aaatcgtaca    480
accaaggctg taacggcggt ctaatggatt atgcttttca attcataatg aaaaacggcg     540
gattaaacac cgagaaagac tatccttacc acggaaccaa tggcaaatgc aactctttac    600
ttaagaattc aagagttgta actatcgatg gatacgaaga tgttcctagt aaagatgaaa    660
ccgcgttgaa gagagcagtt tcataccagc ctgtgagtgt tgctattgat gctggtggaa    720
gagcttttcca acattaccaa tctggaatct tcactggaaa gtgtggtacg aatatggatc     780
acgctgtggt ggcggttggt tatgggtcag agaacggcgt tgactattgg attgtacgta    840
actcttgggg tacacgttgg ggagaggatg gttacattag gatggagaga aacgtggcgt    900
ctaaatccgg taagtgtggg attgcgatag aagcctcgta tccggttaag tacagcccaa    960
acccggttcg tggaaccagc agtgtttgaa gttaacaaaa agaatctcat gcagtaatca   1020
aattgggatt gttataagtt aaattaatct tgtattattg tttgtatgta tagtattcgg    1080
```

-continued

```
aaaaaaaatg attcaccata gg                                            1102

<210> SEQ ID NO 87
<211> LENGTH: 13
<212> TYPE: DNA
<213> ORGANISM: Artificial Sequence
<220> FEATURE:
<223> OTHER INFORMATION: Description of Artificial Sequence:consensus

<400> SEQUENCE: 87
cattaataaa aag                                                        13

<210> SEQ ID NO 88
<211> LENGTH: 13
<212> TYPE: DNA
<213> ORGANISM: Artificial Sequence
<220> FEATURE:
<223> OTHER INFORMATION: Description of Artificial Sequence:consensus

<400> SEQUENCE: 88
tggttataaa tag                                                        13

<210> SEQ ID NO 89
<211> LENGTH: 20
<212> TYPE: PRT
<213> ORGANISM: Artificial Sequence
<220> FEATURE:
<223> OTHER INFORMATION: Description of Artificial Sequence:motif
<220> FEATURE:
<221> NAME/KEY: SITE
<222> LOCATION: (2)..(4)
<223> OTHER INFORMATION: variable amino acid
<220> FEATURE:
<221> NAME/KEY: SITE
<222> LOCATION: (6)..(8)
<223> OTHER INFORMATION: variable amino acid
<220> FEATURE:
<221> NAME/KEY: SITE
<222> LOCATION: (10)..(11)
<223> OTHER INFORMATION: variable amino acid
<220> FEATURE:
<221> NAME/KEY: SITE
<222> LOCATION: (13)..(15)
<223> OTHER INFORMATION: variable amino acid
<220> FEATURE:
<221> NAME/KEY: SITE
<222> LOCATION: (17)..(19)
<223> OTHER INFORMATION: variable amino acid

<400> SEQUENCE: 89

Glu Xaa Xaa Xaa Arg Xaa Xaa Xaa Phe Xaa Xaa Asn Xaa Xaa Xaa Ile
 1               5                  10                  15

Xaa Xaa Xaa Asn
            20
```